United States Patent
Stasi et al.

(10) Patent No.: US 9,493,438 B2
(45) Date of Patent: Nov. 15, 2016

(54) 4,4-DIFLUORO-PIPERIDINE-COMPOUNDS

(71) Applicant: ROTTAPHARM BIOTECH S.R.L., Monza (IT)

(72) Inventors: Luigi Piero Stasi, Monza (IT); Lucio Rovati, Monza (IT); Roberto Artusi, Rho (IT); Clara Bovino, Gessate (IT); Fabrizio Colace, Monza (IT); Stefano Mandelli, Casatenovo (IT)

(73) Assignee: Rottapharm S.R.L., Monza (IT)

( * ) Notice: Subject to any disclaimer, the term of this patent is extended or adjusted under 35 U.S.C. 154(b) by 0 days.

(21) Appl. No.: 14/381,815

(22) PCT Filed: Feb. 28, 2013

(86) PCT No.: PCT/EP2013/054017
§ 371 (c)(1),
(2) Date: Aug. 28, 2014

(87) PCT Pub. No.: WO2013/127913
PCT Pub. Date: Sep. 6, 2013

(65) Prior Publication Data
US 2015/0051226 A1 Feb. 19, 2015

(30) Foreign Application Priority Data
Mar. 1, 2012 (IT) .............. MI2012A0322

(51) Int. Cl.
*C07D 417/14* (2006.01)
*C07D 401/12* (2006.01)
*C07D 401/14* (2006.01)

(52) U.S. Cl.
CPC ........... *C07D 401/14* (2013.01); *C07D 401/12* (2013.01); *C07D 417/14* (2013.01)

(58) Field of Classification Search
CPC  C07D 401/12; C07D 401/14; C07D 417/06; C07D 417/14
USPC .......... 514/252.2, 256, 275, 236.5, 311, 314, 514/318, 320, 321, 326, 365; 544/130, 238, 544/295, 296; 546/167, 169, 194, 196, 198, 546/209; 548/181
See application file for complete search history.

(56) References Cited

U.S. PATENT DOCUMENTS

2014/0364432 A1* 12/2014 Kamenecka et al. ...... 514/236.5

FOREIGN PATENT DOCUMENTS

| WO | 0196302 A1 | 12/2001 |
| WO | 2009016560 | 2/2009 |
| WO | 2009040730 A2 | 4/2009 |
| WO | 2011006960 | 1/2011 |
| WO | WO2013119639 | * 8/2013 |

OTHER PUBLICATIONS

International Search Report dated Jun. 25, 2013 corresponding to International Patent Application No. PCT/EP2013/054017; 3 pages.
Written Opinion dated Jun. 25, 2013 corresponding to International Patent Application No. PCT/EP2013/054017; 4 pages.
International Preliminary Report on Patentability dated Sep. 2, 2014 corresponding to PCT/EP2013/054017; 5 pages.
Hara et al; "Genetic Ablation of Orexin Neurons in Mice Results in Narcolepsy, Hypophagia, and Obesity"; Neuron vol. 30; May 2001;pp. 345-354.
Kane et al; "Nicotine Up-Regulates Expression of Orexin and its Receptors in Rat Brain"; Endocrinology, vol. 141, No. 10; Mar. 2000; pp. 1-7.
Kane et al; "Hypothalamic Orexin-A Binding Sites are Downregulated by Chronic Nicotine Treatment in the Art"; Elsevier; Nov. 3, 2000; pp. 1-4.
Kang et al; Amyloid-β Dynamics are Regulated by Orexin and the Sleep-Wake Cycle; Science 326, 1005 (2009); Nov. 3, 2014; pp. 1-4.
Lawrence et al; "The Orexin System Regulates Alcohol-Seeking In Rats"; British Journal of Pharmacology; Jun. 5, 2006; pp. 1-8.
Mignot et al; "Complex HLA-DR and -DQ Interactions Confer Risk of Narcolepsy-Cataplexy in Three Ethnic Groups"; The American Society of Humane Genetics, Nov. 27, 2000; pp. 689-699.
Buckner et al; "Then DNA-Repair Gene MBMT and the Clinical Response of Gliomas to Alkylating Agent"; The New England Journal of Medicine, vol. .344, No. 9; Mar. 1, 2001; pp. 1-8.
Nakamura et al; "Orexin-induced Hyperlocomotion and Stereotypy are Mediated by the Dopaminergic System"; Elsevier; Jun. 9, 2000; pp. 1-7.

(Continued)

*Primary Examiner* — Celia Chang
(74) *Attorney, Agent, or Firm* — Ohlandt, Greeley, Ruggiero & Perle, LLP

(57) ABSTRACT

The invention, in a first aspect relates to compounds of formula (I)

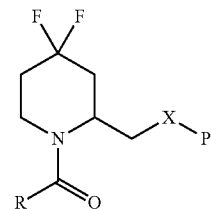

or a pharmaceutically acceptable salt thereof, wherein
R is a 6-membered aromatic ring, or a 5- or 6-membered heteroaromatic ring comprising 1 to 3 heteroatoms selected from S, O and N, or a 6-membered benzocondensed heteroaromatic ring containing N as heteroatom, optionally each of said rings being substituted with one or two substituents selected from the group consisting of (C1-C3)alkyl, (C3-C5)cycloalkyloxy, (C1-C3)alkylcarbonyl, cyano, trifluoromethyl, dimethylamino, or phenyl which optionally is substituted with one or more halogen atoms, or a 5- or 6-membered heterocycle containing from one to three nitrogen atoms;
X is O or N;
P is pyridyl, pyrimidyl, pyrazyl, or pyridazyl, each being optionally substituted with one or more substituents selected from the group consisting of (C1-C3)alkyl, halogen, trifluoromethyl, and cyano, and use thereof as pharmaceuticals.

24 Claims, No Drawings

(56) References Cited

OTHER PUBLICATIONS

Malherbe et al; "Biochemical and Electorphysiological Characterization of Almorexant, a Dual Orexin 1 Receptor ($OX_1$)/Orexin 2 Receptor ($OX_2$) Antagonist: Comparison with Selective $OX_1$ and $OX_2$ Antagonists"; The American Society for Pharmacology and Experimental Therapeutics; Jun. 17, 2009; pp. 1-14.

Piper et al; "The novel brain neuropeptide, orexin-A, modulates the sleep-wake cycle of rats"; European Journal of Neuroscience, vol. 12; Oct. 12, 1999; pp. 726-730.

Richards et al; "Inhibition of orexin-1/hypocretin-1 receptors inhibits yohimbine-induced reinstatement of ethanol and sucrose seeking in Long-Evans rats"; Psychopharmacology; May 10, 2008; pp. 109-117.

Takeshi Sakurai; "Orexins and orexin receptors: implication in feeding behavior"; Elsevier; Jul. 30, 1999; pp. 1-6.

Schneider et al; "Orexigenic Peptides and Alcohol Intake: Differentia Effects of Orexin, Galanin, and "; Alcoholism: clinical and Experimental Research, vol. 31, No. 11; Nov. 2007; pp. 1-8.

Takeshi Sakurai; "The neural circuit of orexin (hypocretin): maintaining sleep and wakefulness"; Neuroscience, vol. 8; Mar. 2007; pp. 1-11.

Anthony N. van den Pol; "Hypothalamic Hypocretin (Orexin): Robust Innervation of the Spinal Cord"; The Journal of Neuroscience; Apr. 15, 1999; pp. 3171-3182.

Samson et al; "Cardiovascular regulatory actions of the hypocretins in brain"; Elsevier; Mar. 1999; pp. 1-6.

Brisbare-Roch et al; "Promotion of sleep by targeting the orexin system in rats,dogs and humans"; Nature Medicine; Jan. 28, 2007; pp. 1-6.

Ninrow et al; "Orexin receptor antagonism prevents transcriptional and behavioral plasticity resulting from stimulant axposure"; Elsevier; Jul. 3, 2009; pp. 1-10.

Peyron et al; "Neurons Containing Hypocretin (Orexin) Project to Multiple Neuronal Systems"; The Journal of Neuroscience; Dec. 1, 1998; pp. 1-20.

Dayas et al; "Stimuli Linked to Ethanol Availability Activate Hypothalamic CART and Orexin Neurons in a Reinstatement Model of Relapse"; Society of Biological Psychiatry; Feb. 3, 2007; pp. 1-6.

Dugovic et al; "Blockade of Orexin-1 Receptors Attenuates Orexin-2 Receptor Antagonism-Induced Sleep Promotion in the Rat"; The Journal of Pharmacology and Experimental Therapeutics, vol. 330, No. 1; Apr. 6, 2009; pp. 1-10.

Aston-Jones et al; "Role of lateral hypothalamic orexin neurons in reward processing and addiction"; Elsevier; Jun. 12, 2008; pp. 1-10.

Georgescu et al; "Involvement of the Lateral Hypothalamic Peptide Orexin in Morphine Dependence and Withdrawal"; The Journal of Neuroscience; Apr. 15, 2003; pp. 3106-3111.

Hamlin et al; "The Neural Correlates and Role of D1 Dopamine Receptors in Renewal of Extinguished Alcohol-Seeking"; Neuroscience; Jan. 2007; pp. 525-536.

Lin et al; The Sleep Disorder Canine Narcolepsy is Caused by a Mutation in the Hypocretin (Orexin) Receptor 2 Gene; Cell, vol. 98; Aug. 6, 1999; pp. 365-376.

Peyron et al; "A Mutation in a Case of Early Onset Narcolepsy and a Generalized Absence of Hypocretion Peptides in Human Narcoleptic Brains"; Nature Medicine, vol. 6, No. 9; Sep. 2000; pp. 1-7.

Shirasaka et al; "Sympatheic and Cardiovascular Actions of Orexins in Conscious Rats"; The American Physiological Society; Sep. 28, 1999; p. 1-6.

Sakurai et al; "Orexins and Orexin Receptors: A Family of Hypothalamic Neuropeptides and G Protein-Coupled Receptors that Regulate Feeding Behavior"; Cell, vol. 92; Feb. 20, 1998; pp. 573-585.

Takahashi et al; "Stimulation of Gastric Acid Secretion by Centrally Administered Orexin-A in Conscious Rats"; Biochemical and Biophysical Research Communications; Dec. 3, 1998; pp. 623-627.

Yamanaka et al; "Orexins Activate Histaminergic Neurons via the Orexin 2 Receptor"; Biochemical and Biophysical Research Communications; Dec. 21, 2001; pp. 1237-1245.

Chen et al; "Pressor Effects of Orexins Injected Intracisternally and to Rostral Ventrolateral Medulla of Anesthetized Rats"; American Journal of Physiology; Sep. 30, 1999; pp. 1-6.

Chemelli et al; Narcolepsy in Orexin Knockout Mice: Molecular Genetics of Sleep Regulation; Cell, vol. 98; Aug. 20, 1999; pp. 437-451.

Kirchgessner et al; "Orexin Synthesis and Response in the Gut"; Neuron, vol. 24; Dec. 1999; pp. 1-11.

\* cited by examiner

4,4-DIFLUORO-PIPERIDINE-COMPOUNDS

FIELD OF THE INVENTION

The invention relates to novel 4,4-difluoro piperidine derivatives and their use as pharmaceuticals.

The invention also concerns a process for the preparation of those compounds, pharmaceutical compositions containing one or more compounds of formula (I) and their use as antagonists of the Orexin receptors.

BACKGROUND OF THE INVENTION

Orexin (or hypocretin) signaling is mediated by two receptors and two peptide agonists. The two orexin peptides (orexin A and orexin B) herein after referred to as orexins, bind to two high affinity receptors, termed Orexin-1 and Orexin-2 receptors. The Orexin-1 receptor is selective in favor of orexin A, while the Orexin-2 receptor binds both orexins with similar affinities. The orexins, are cleavage products of the same gene, prepro orexin. In the central nervous system neurons expressing prepro-orexin, the precursor from which orexin is produced, are found in the perifornical nucleus, the dorsal hypothalamus and the lateral hypothalamus (C. Peyron et al., J. Neurosci., 1998, 18(23), 9996-10015). Orexinergic cells in these nuclei project to many areas of the brain, extending rostrally to the olfactory bulbs and caudally to the spinal cord (van den Pol, A. N. et al., J. Neuroscience., 1999, 19(8), 3171-3182).

The broad CNS distribution of orexin projections and neurons expressing orexin receptors is suggestive of orexin involvement in a number of physiological functions including; feeding, drinking, arousal, stress, reward, metabolism and reproduction (T. Sakurai, Nature Reviews Neuroscience, 2007, 8(3), 171-181). The targeted necrosis of cells expressing prepro-orexin suggests the most physiologically important roles of the orexins are likely to be effects on arousal, feeding and metabolism (J. Hara et al., Neuron, 2001, 30, 345-354). A prominent orexin neuronal projection via the vagus nerve probably mediates central orexin effects on cardiac parameters (W. K. Samson et al., Brain Res., 1999, 831, 248-253; T. Shirasaka et al., Am. J. Physiol., 1999, 277, R1780-R1785; C.-T. Chen et al., Am. J. Physiol., 2000, 278, R692-R697), gastric acid secretion and gastric motility (A. L. Kirchgessner and M.-T. Liu, Neuron, 1999, 24, 941-951; N. Takahashi et al., Biochem. Biophys. Res. Commun., 1999, 254, 623-627). Several lines of evidence indicate that the orexin system is an important modulator of arousal. Rodents administered orexins intracerebroventricularly spend more time awake (Piper et al., J. Neurosci. 2000, 12, 726-730). Orexin-mediated effects on arousal have been linked to orexin neuronal projections to histaminergic neurons in the tuberomammillary nucleus (TMN) (Yamanaka et al., Biochem. Biophys. Res. Comm. 2002, 290, 1237-1245). TMN neurons express the orexin-2 receptor primarily, and the orexin-1 receptor to a lesser extent. Rodents whose prepro orexin gene has been knocked out, or whose orexigenic neurons have been lesioned, display altered sleep/wake cycles similar to narcolepsy (Chemelli et al., Cell 1999, 98, 437-451; Hara et al., 2001, supra). Dog models of narcolepsy have been shown to have mutant or nonfunctional orexin-2 receptors (Lin et al., Cell 1999, 98, 365-376). Human narcolepsy appears to be linked to deficient orexin signaling, likely related to immune ablation of orexinergic neurons in the lateral hypothalamus (Mignot et al., Am. J. Hum. Genet. 2001, 68: 686-699; Minot & Thorsby, New England J. Med. 2001, 344, 692), or, in rare cases, to mutations in the orexin-2 gene (Peyron et al., Nature Med. 2000, 6, 991-997). The disclosure that rats, dogs and humans treated with the dual orexin-1/2 receptor antagonist, ACT-078573 (Brisbare-Roch et al., Nature Medicine, 2007, 13, 150-155) exhibited decreased alertness together with characteristic clinical and EEG (electroencephalographic) signs of sleep provides evidence to support a role for the orexin system in the regulation of arousal, sleep and wake states. EEG data indicates that orexin-2 may be important in the modulation of sleep/wake (P. Malherbe et al., Molecular Pharmacology (2009) 76(3):618-31; C. Dugovic et al., J. Pharmacol. Exp. Then, 2009, 330(1), 142-151). Disorders of the sleep-wake cycle are therefore likely targets for orexin receptor antagonist therapy. Examples of such disorders include sleep-wake transition disorders, insomnia, restless legs syndrome, jet-lag, disturbed sleep, and sleep disorders secondary to neurological disorders (e.g., manias, depressions, manic depression, schizophrenia, and pain syndromes (e.g., fibromyalgia, neuropathic pain). The orexin system also interacts with brain dopamine systems. Intracerebroventricular injections of orexins in mice increase locomotor activity, grooming and stereotypy; these behavioral effects are reversed by administration of D2 dopamine receptor antagonists (Nakamura et al., Brain Research, 873 (1), 181-7). Therefore, orexinmodulators may be useful to treat various neurological disorders; e.g., agonists or up-regulators to treat catatonia, antagonists or down-regulators to treat Parkinson's disease, Tourette's syndrome, anxiety, delerium and dementias.

Recent evidence indicates a role for orexin in the pathogenesis of Alzheimers disease (Kang et al, Science Express, 2009, 1-10). Brain interstitial fluid levels of amyloid-beta were demonstrated to fluctuate diurnally in both humans and rodents with sleep deprivation in rodents leading to significant increases in brain interstitial fluid levels of amyloid-beta. Infusion of a dual orexin antagonist in rodents suppressed interstitial levels of amyloid-beta and abolished the natural diurnal variation of amyloid-beta. The reduction of interstitial fluid amyloid-beta levels is correlated with reduced amyloid plaque formation, a hallmark of Alzheimer's disease, and consequently the regulation of sleep time could potentially inhibit amyloid-beta aggregation and slow the progression of Alzheimer's disease. Orexin neurons project to many regions of the brain associated with reward function (T. Sakurai, supra) and research, focusing on animal models of drug intake, reward, and reinstatement, has expanded the link between the orexin system and addiction. A comprehensive set of data suggest that drugs of abuse activate the orexin system, which in turn enhances drug reward or drug seeking (G. Aston-Jones et al., Neuropharmacology, 2009, 56 (Suppl 1) 112-121. Thus interactions between nicotine (J. K. Kane et al., Endocrinology, 2000, 141 (10), 3623-3629; J. K. Kane et al., Neurosci. Lett, 2001, 298(1), 1-4), morphine (D. Georgescu, et al., J. Neurosci., 2003, 23(8), 3106-3111) and amphetamine (C. J. Winrow et al., Neuropharmacology, 2010, 58(1), 185-94) and the orexin system have been demonstrated. Additional studies from a number of laboratories have demonstrated an important relationship between the Orexin system and ethanol consumption. As examples, ethanol consumption in an alcohol-preferring strain of rat was shown to up regulate Orexin mRNA in the lateral hypothalamus and that an Orexin-1 receptor antagonist reduced operant responding for ethanol (Lawrence, et. al., Br. J. Pharmacol., 2006, 148, 752-759). Treatment with an orexin-1 antagonist has also been shown to decrease operant responding for ethanol (Richards, et. al., Psychopharmacology, 2008, 199 (1), 109-117). Other studies have demonstrated increased Fos activation of orexin neurons following contextual reinstatement to ethanol seeking (Dayas, et. al., Biol. Psychiatry, 2008, 63 (2), 152-157 and Hamlin, et. al., Neuroscience, 2007, 146, 525-536). Studies have also shown increased ethanol consumption following Orexin infusion into the paraventricular nucleus of the hypothalamus or in the lateral hypothalamus (Schneider, et. al., Alcohol. Clin. Exp. Res., 2007, 37(11), 1858-1865). These studies provide evidence that modulation of the Orexin system effects alcohol preference and therefore Orexin receptor antagonists are likely to be useful for the treatment of alcoholism.

Orexins and their receptors have been found in both the myenteric and submucosal plexus of the enteric nervous system, where orexins have been shown to increase motility in vitro (Kirchgessner & Liu, Neuron 1999, 24, 941-951 and to stimulate gastric acid secretion in vitro (Takahashi et al., Biochem. Biophys. Res. Comm. 1999, 254, 623-627). Orexin mediated effects on the gut may be driven by a projection via the vagus nerve (van den Pol. 1999, supra), as vagotomy or atropine prevent the effect of an intracerebroventricular injection of orexin on gastric acid secretion (Takahashi et al., 1999, supra). Orexin receptor antagonists or other down-regulators of orexin receptor-mediated systems are therefore potential treatments for ulcers, irritable bowel syndrome, diarrhea and gastroesophageal reflux. Body weight may also be affected by orexin-mediated regulation of appetite and metabolism (T. Sakurai et al., Cell, 1998, 92(4), 573-585; T. Sakurai, Reg. Pept, 1999, 85(1), 25-30). Some effects of orexin on metabolism and appetite may be mediated in the gut, where, as mentioned, orexins alter gastric motility and gastric acid secretion. Orexin receptor antagonists therefore are likely to be useful in treatment of overweight or obesity and conditions related to overweight or obesity, such as insulin resistance, type II diabetes, hyperlipidemia, gallstones, angina, hypertension, breathlessness, tachycardia, infertility, sleep apnea, back and joint pain, varicose veins and osteoarthritis. Conversely, orexin receptor agonists are likely to be useful in treatment of underweight and related conditions such as hypotension, bradycardia, amenorrhea and related infertility, and eating disorders such as anorexia and bulimia. Intracerebroventricularly administered orexins have been shown to increase mean arterial pressure and heart rate in freely moving (awake) animals (Samson et al., Brain Res. 1999, 831, 248-253; Shirasaka et al., Am. J. Physiol. 1999, 277, R1780-R1785) and in urethane-anesthetized animals (Chen et al., Am. J. Physiol. 2000, 278, R692-R697), with similar results. Orexin receptor agonists may therefore be candidates for treatment of hypotension, bradycardia and heart failure related thereto, while orexin receptor antagonists may be useful for treatment of hypertension, tachycardia and other arrhythmias, angina pectoris and acute heart failure. From the foregoing discussion, it can be seen that the identification of orexin receptor antagonists will be of great advantage in the development of therapeutic agents for the treatment of a wide variety of disorders that are mediated through these receptor systems.

In the international patent application WO2009/016560 trans-3-aza-biciclo[3.1.0]exane derivatives have been disclosed as a series of orexin antagonists.

Novel pyrrolidine and piperidine derivatives have been disclosed in WO2009/040730, spiro amino selective orexin-1 antagonists were disclosed in the international patent application WO2011/006960.

There remains a need, however, for potent orexin antagonists with desirable pharmaceutical properties.

One of the objects of the present invention is to provide 4,4-difluoro piperidine compounds with antagonist activity at the orexin receptors.

SUMMARY OF THE INVENTION

The inventors of the present application have discovered novel compounds that are selective antagonists of the orexin-1 receptors and pharmaceutical compositions which are useful for the treatment or alleviation of orexins mediated diseases.

According to a first general aspect, the present invention thus provides a compound of formula (I) or a pharmaceutically acceptable salt thereof:

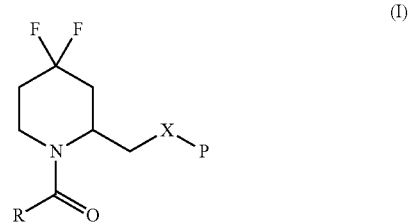

wherein
X is O or N;
R is a 6-membered aromatic ring, or a 5- or 6-membered heteroaromatic ring comprising 1 to 3 heteroatoms selected from S, O and N, or a 6-membered benzocondensed heteroaromatic ring containing N as heteroatom, optionally each of said rings being substituted with one or two substituents selected from the group consisting of $(C_1-C_3)$alkyl, $(C_3-C_5)$cycloalkyloxy, $(C_1-C_3)$alkylcarbonyl, cyano, trifluoromethyl, dimethylamino, or phenyl which optionally is substituted with one or more halogen atoms, or a 5- or 6-membered heterocycle containing from one to three nitrogen atoms;
P is pyridyl, pyrimidyl, pyrazyl, or pyridazyl, each of them independently being optionally substituted with one or more substituents preferably selected from the group consisting of $(C_1-C_3)$alkyl, halogen, trifluoromethyl, and cyano.

In certain embodiments R is 6-membered aromatic ring, or a 5- or 6-membered heteroaromatic ring, each of said rings being substituted with one or two substituents selected from the group consisting of $(C_1-C_3)$alkyl, $(C_3-C_5)$cycloalkyloxy, $(C_1-C_3)$alkylcarbonyl, cyano, trifluoromethyl, dimethylamino, or phenyl which optionally is substituted with one or more halogen atoms, or a 5- or 6-membered heterocycle containing from one to three nitrogen atoms.

In certain embodiments of the present invention, R is a 6-membered aromatic ring, typically phenyl, optionally substituted as defined above.

In certain embodiments of the invention R is 5-membered heteroaromatic ring containing S and/or N as heteroatom, such as 1,3 thiazole, optionally substituted as defined above.

In certain embodiments of the invention R is a 6-membered heteroaromatic ring containing N as heteroatom, such as pyrimidine or pyridine, each optionally substituted as above.

In certain embodiments R is a 6-membered benzocondensed heteroaromatic ring containing N as heteroatom such as isoquinoline, quinoline, or piperidine.

In certain embodiments P is pyridyl, pyrimidyl, pyrazyl, or pyridazyl, each of these heteroaromatic rings being optionally substituted with one or more substituents selected from the group consisting of ($C_1$-$C_3$)alkyl, halogen, trifluoromethyl, and cyano.

In this invention compounds of Formula (I) may typically exist as R and S enantiomers and as racemic mixture. This invention includes in its scope of protection all the possible isomers and racemic mixtures. Wherever should be present further symmetry centres, this invention includes all the possible diastereoisomers and relative mixtures as well.

In a second aspect the difluoro-amino compound of Formula (I), wherein X is N is provided.

In accordance with this second aspect, a subset of compounds of Formula (Ia) is provided:

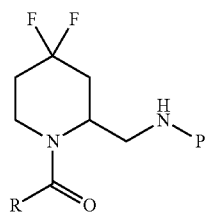

(Ia)

wherein R, P are as defined above.

In a third aspect difluoro-amino compound of Formula (I), wherein X is O is provided.

In accordance with this aspect of the invention, a subset of compounds of Formula (Ib) is provided:

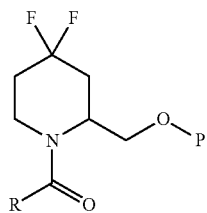

(Ib)

wherein R, P are as defined above.

In a fourth aspect the invention concerns pharmaceutical compositions comprising a compound of formula (I) or (Ia), (Ib) and a pharmaceutically acceptable carrier.

In a fifth aspect the invention concerns a compound of Formula (I) as a medicament, in particular it concerns its use for the treatment of pathologies where an antagonist of the orexin receptors is needed, such as the treatment of obesity, sleep disorders, compulsive disorders, drug dependency, schizophrenia.

In an additional aspect the present invention provides a method of treatment of pathologies where an antagonist of the orexin receptors is needed, in particular the treatment of obesity, sleep disorders, compulsive disorders, drug dependency or schizophrenia comprising the administration of a compound of Formula (I) or of the subsets of Formula (Ia) or (Ib) in a therapeutically effective amount with a pharmaceutically acceptable carrier and/or an excipient.

In accordance with additional aspects of the present invention, a process for the preparation of the compounds (I), or subset (Ia), (Ib) is provided as described hereinafter.

DETAILED DESCRIPTION OF THE INVENTION

The invention thus concerns, in a first aspect, a difluoro-amino compound of Formula (I):

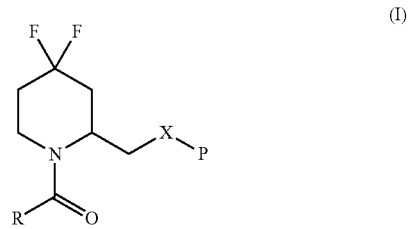

(I)

wherein
X is O or N;
R is
  i) a 6-membered aromatic ring, or
  ii) a 5- or 6-membered heteroaromatic ring comprising 1 to 3 heteroatoms selected from S, O and N, or
  iii) a 6-membered benzocondensed heteroaromatic ring containing N as heteroatom,
wherein optionally each of said rings i) or ii) is substituted with
  one or two substituents selected from the group consisting of ($C_1$-$C_3$)alkyl, ($C_3$-$C_5$)cycloalkyloxy, ($C_1$-$C_3$)alkylcarbonyl, cyano, trifluoromethyl, dimethylamino, or phenyl optionally substituted with one or more halogen atoms, or
  a 5- or 6-membered heterocycle comprising from one to three nitrogen atoms as heteroatom;
P is pyridyl, pyrimidyl, pyrazyl, or pyridazyl, each of such rings being optionally substituted with one or more substituents selected from the group consisting of ($C_1$-$C_3$)alkyl, halogen, trifluoromethyl, and cyano.

Any of these groups may be attached to the rest of the molecule at any suitable position.

In certain embodiments of the present invention, R is a 6-membered aromatic ring, typically phenyl, such phenyl being optionally substituted as defined above.

In certain embodiments R is a 5-membered heteroaromatic ring containing S and/or N as heteroatom, such as 1,3 thiazole, such ring being optionally substituted as above.

In certain embodiments R is a 6-membered heteroaromatic ring containing N as heteroatom such as pyrimidine or pyridine, each ring being optionally substituted as above.

In certain embodiments the 6-membered heteroaromatic ring containing N as heteroatom is pyrimidine substituted in the 2 position with a substituent as defined above.

In certain embodiments R is a 6-membered benzocondensed heteroaromatic ring containing N as heteroatom such as isoquinoline, quinoline, piperidine, such ring being optionally substituted as above.

In certain embodiments P is selected from 5-(chloro)pyridin-2yl; 5-(trifluoromethyl)pyridin-2-yl; 3-fluoro-5-(trifluoromethyl)pyridin-2-yl; 5-(trifluoromethyl)pyrazin-2-yl.

The term "halogen" as used herein refers to a fluorine, chlorine, bromine or iodine atom. In certain embodiments the halogen is chlorine or fluorine.

The term "$C_1$-$C_3$ alkyl" as used herein refers to a linear or branched saturated hydrocarbon group containing of 1 to 3 carbon atoms. Examples of such groups include methyl, ethyl, n-propyl, isopropyl.

It will be understood that, as used herein, references to the compounds of Formula (I) are meant to include the subsets of compounds of Formulae (Ia) and (Ib), as described hereinafter, where appropriate.

In a second aspect of the invention, a subset of compounds of Formula (Ia), wherein X is N, is provided. This is a difluoro-amino compound of Formula (Ia):

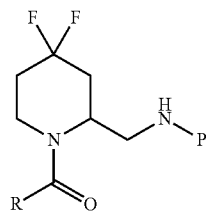

wherein R and P are as defined above (formula I).

In certain embodiments R is phenyl optionally substituted with a group selected from cyclopropyl($C_1$-$C_3$)alkyloxy, triazolyl, pyrimidyl, phenyl. In these embodiments, typically, the phenyl may be substituted in position 2.

In certain embodiments R is a 5-membered heteroaromatic ring, containing 1 to 3 heteroatoms selected from S and N, optionally substituted as defined above.

In certain embodiments R is a thiazole ring, preferably a thiazole ring substituted with at least one substituent selected from the group consisting of methyl, phenyl, and phenyl which typically may be substituted with one or more halogens. In certain embodiments R is a 6-membered heteroaromatic ring containing N as heteroatom, such as pyrimidine or pyridine optionally substituted with substituents as defined above.

In certain embodiments the 6-membered heteroaromatic ring containing N as heteroatom is pyrimidine substituted in the 2 position, as defined above, for example with a group selected from (C1-C3)alkyloxy, trifluoromethyl, halogen, triazolyl, pyrimidyl, phenyl.

In certain embodiments R is a pyridyl ring, optionally substituted as above.

In certain embodiments R is a pyridyl ring substituted with a group selected from ($C_1$-$C_3$)alkyloxy, trifluoromethyl, halogen, triazolyl, pyrimidyl, phenyl.

In certain embodiments R is a 6-membered benzocondensed heteroaromatic ring containing N as heteroatom such as isoquinoline, quinolone, or piperidine.

In certain embodiments P is a pyridyl ring, optionally substituted with one of the substituents defined above.

In certain embodiments P is a pyridyl ring substituted with one or more substituents selected from the group consisting of trifluoromethyl, methyl and halogen.

Any of the above groups may be attached to the rest of the molecule at any suitable position.

In certain embodiments of this second aspect of the invention the compounds of the subset of Formula Ia are selected from the group consisting of:
(RS)(2-(((5-chloropyridin-2-yl)amino)methyl)-4,4-difluoropiperidin-1-yl)(2-methyl-5-phenylthiazol-4-yl)methanone
(2-(((5-chloropyridin-2-yl)amino)methyl)-4,4-difluoropiperidin-1-yl)(2-methyl-5-phenylthiazol-4-yl)methanone (enantiomer A)
(2-(((5-chloropyridin-2-yl)amino)methyl)-4,4-difluoropiperidin-1-yl)(5-methyl-2-(2H-1,2,3-triazol-2-yl)phenyl)methanone (enantiomer A)
(2-(((4,6-dimethylpyrimidin-2-yl)amino)methyl)-4,4-difluoropiperidin-1-yl)(5-methyl-2-(2H-1,2,3-triazol-2-yl)phenyl)methanone (enantiomer A)
(RS)(4,4-difluoro-2-(((5-(trifluoromethyl)pyridin-2-yl)amino)methyl)piperidin-1-yl)(5-methyl-2-(2H-1,2,3-triazol-2-yl)phenyl)methanone
(RS)(2-(((5-chloropyridin-2-yl)amino)methyl)-4,4-difluoropiperidin-1-yl)(5-methyl-2-(pyrimidin-2-yl)phenyl)methanone
(2-(((5-chloropyridin-2-yl)amino)methyl)-4,4-difluoropiperidin-1-yl)(5-methyl-2-(pyrimidin-2-yl)phenyl)methanone (enantiomer A)
(2-(((5-chloropyridin-2-yl)amino)methyl)-4,4-difluoropiperidin-1-yl)(6-methyl-3-(2H-1,2,3-triazol-2-yl)pyridin-2-yl)methanone (enantiomer A)
(2-(((5-chloropyridin-2-yl)amino)methyl)-4,4-difluoropiperidin-1-yl)(6-methyl-3-(2H-1,2,3-triazol-2-yl)pyridin-2-yl)methanone (enantiomer B)
(RS)(2-(((5-chloropyridin-2-yl)amino)methyl)-4,4-difluoropiperidin-1-yl)(2-ethoxyphenyl)methanone
(RS)(2-(((5-chloropyridin-2-yl)amino)methyl)-4,4-difluoropiperidin-1-yl)(2,5-dimethoxyphenyl)methanone
(RS)(2-(((5-chloropyridin-2-yl)amino)methy)-4,4-difluoropiperidin-1-yl)(2-(cyclopropylmethoxy)phenyl)methanone
(RS)(2-(((5-chloropyridin-2-yl)amino)methy)-4,4-difluoropiperidin-1-yl)(2-(cyclopentyloxy)phenyl)methanone
(RS)(2-(((5-chloropyridin-2-yl)amino)methyl)-4,4-difluoropiperidin-1-yl)(6-methyl-3-(pyrimidin-2-yl)pyridin-2-yl)methanone
(RS)(2-(((5-chloropyridin-2-yl)amino)methyl)-4,4-difluoropiperidin-1-yl)(5-methyl-2-(pyrimidin-2-yl)pyridin-3-yl)methanone
(2-(((5-chloropyridin-2-yl)amino)methyl)-4,4-difluoropiperidin-1-yl)(6-methyl-3-(pyrimidin-2-yl)pyridin-2-yl)methanone (enantiomer A)
(2-(((5-chloropyridin-2-yl)amino)methyl)-4,4-difluoropiperidin-1-yl)(6-methyl-3-(pyrimidin-2-yl)pyridin-2-yl)methanone (enantiomer B)
(RS)(2-(((5-chloropyridin-2-yl)amino)methyl)-4,4-difluoropiperidin-1-yl)methanone
(RS)(5-chloro-2-(pyridine-2-yl)phenyl)(2-(((5-chloropyridin-2-yl)amino)methyl)-4,4-difluoropiperidin-1-yl)methanone
(4,4-difluoro-2-(((5-(trifluoromethyl)pyridin-2-yl)amino)methyl)piperidin-1-yl)(6-methyl-3-(pyrimidin-2-yl)pyridin-2-yl)methanone (enantiomer A)
(RS)(2-(benzyloxy)phenyl)(2-(((5-chloropyridin-2-yl)amino)methyl)-4,4-difluoropiperidin-1-yl)methanone
(RS)(2-(((5-chloropyridin-2-yl)amino)methyl)-4,4-difluoropiperidin-1-yl)(isoquinolin-1-yl)methanone
(2-(((5-chloropyridin-2-yl)amino)methyl)-4,4-difluoropiperidin-1-yl)(isoquinolin-1-yl)methanone (enantiomer A)
(2-(((5-chloropyridin-2-yl)amino)methyl)-4,4-difluoropiperidin-1-yl)(isoquinolin-1-yl)methanone (enantiomer B)
(RS)(2-(((5-chloropyridin-2-yl)amino)methyl)-4,4-difluoropiperidin-1-yl)(quinolin-8-yl)methanone
(2-(((5-chloropyridin-2-yl)amino)methyl)-4,4-difluoropiperidin-1-yl)(quinolin-8-yl)methanone (enantiomer A)
(RS)3-(2-(((5-chloropyridin-2-yl)amino)methyl)-4,4-difluoropiperidine-1-carbonyl)-4-(pyrimidin-2-yl)benzonitrile
(RS)(2-(((5-chloropyridin-2-yl)amino)methy)-4,4-difluoropiperidin-1-yl)(3-(pyrimidin-2-yl)pyridine-4-yl)methanone
(RS)6-(((4,4-difluoro-1-(6-methyl-3-(pyrimidin-2-yl)picolinoyl)piperidin-2-yl)methyl)amino)nicotinonitrile (RS)(4,4-difluoro-2-(((5-(trifluoromethyl)pyridin-2yl)amino)methyl)piperidin-1-yl)(5-fluoro-2-(2-methylpyrimidin-5-yl)phenyl)methanone (RS)(4,4-difluoro-2-(((3-fluoro-5-(trifluoromethyl)pyridin-2-yl)amino)methyl)piperidin-1-yl)(6-methyl-3-(pyrimidin-2-yl)pyridin-2-yl)methanone (RS)(4,4-difluoro-2-(((3-fluoro-5-(trifluoromethyl)pyridin-2-yl)amino)methyl)piperidin-1-yl)(isoquinolin-1-yl)methanone (RS)(4,4-difluoro-2-(((5-(trifluoromethyl)pyridin-2-yl)amino)methyl)piperidin-1-yl)(isoquinolin-1-yl)methanone (RS)(4,4-difluoro-2-(((5-(trifluoromethyl)pyridin-2-yl)amino)methyl)piperidin-1-yl)(quinolin-4-yl)methanone (RS)(4,4-difluoro-2-(((5-(trifluoromethyl)pyridin-2-yl)amino)methyl)piperidin-1-yl)(6-methyl-3-phenylpyridin-2-yl)methanone (RS)(4,4-difluoro-2-(((5-(trifluoromethyl)pyridin-2-yl)amino)methyl)piperidin-1-yl)(3-(pyrimidin-2-yl)-6-(trifluoromethyl)pyridin-2-yl)methanone (4,4-difluoro-2-(((5-(trifluoromethyl)pyridin-2-yl)amino)methyl)piperidin-1-yl)(isoquinolin-1-yl)methanone (enantiomer A)

(RS)(4,4-difluoro-2-(((5-(trifluoromethyl)pyrazin-2-yl)amino)methyl)piperidin-1-yl)(6-methyl-3-(pyrimidin-2-yl)pyridin-2-yl)methanone (RS)(4,4-difluoro-2-(((5-(trifluoromethyl)pyrazin-2-yl)amino)methyl)piperidin-1-yl)(6-methyl-3-phenylpyridin-2-yl)methanone (RS)(4,4-difluoro-2-(((3-fluoro-5-(trifluoromethyl)pyridin-2-yl)amino)methyl)piperidin-1-yl)(6-methyl-3-phenylpyridin-2-yl)methanone, and/or (RS)(4,4-difluoro-2-(((5-(trifluoromethyl)pyridin-2-yl)amino)methyl)piperidin-1-yl)(3-phenylpyridin-2-yl)methanone In accordance with the third aspect of the present invention, a subset of compounds of Formula (Ib), wherein X is O, is provided.

This is a difluoro-amino compound of Formula (Ib):

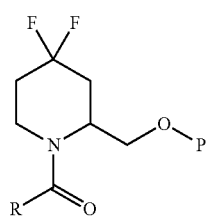

Ib wherein R and P are as defined above for compounds of formula (I).

In certain embodiments R is phenyl, optionally substituted with a group selected from cyclopropyl, $(C_1-C_3)$ alkyloxy, triazolyl, pyrimidyl, phenyl. Typically, in these embodiments the phenyl may be substituted in position 2.

In certain embodiments R is a 5-membered heteroaromatic ring containing S and/or N as heteroatoms, optionally substituted as defined above (formula I).

In certain embodiments R is a thiazole ring, such as a thiazole ring substituted with at least one substituent selected from the group consisting of methyl, phenyl, or phenyl which typically is substituted with one or more halogens.

In certain embodiments R is a 6-membered heteroaromatic ring containing N as heteroatom such as pyrimidine, pyridine, each rings optionally being substituted as defined above (formula I).

In certain embodiments the 6-membered heteroaromatic ring is pyrimidine substituted, preferably in the 2 position, with one or more substituents as defined above.

In certain embodiments R is a pyridyl ring.

In certain embodiments R is a pyridyl ring substituted with a group selected from $(C_1-C_3)$alkyloxy, trifluoromethyl, halogen, triazolyl, pyrimidyl, phenyl.

In certain embodiments R is a 6-membered benzocondensed heteroaromatic ring containing N as heteroatom preferably selected from isoquinoline, piperidine and quinoline.

In certain embodiments the 6-membered benzocondensed heteroaromatic ring containing N as heteroatom is isoquinoline substituted in 1 position or quinoline substituted in 4- or 8 positions, wherein the substituents are defined as above.

In certain embodiments P is a pyridyl ring. In certain embodiment such pyridyl ring is substituted with one or more substituents as defined above, for example, selected from the group consisting of trifluoromethyl, methyl, pyrimidinyl, and halogen.

Any of the above groups may be attached to the rest of the molecule at any suitable position.

In certain embodiments of this third aspect of the invention, the compounds of Formula (Ib) are selected from the group consisting of:

(RS)(4,4-difluoro-2-(((5-(trifluoromethyl)pyridin-2-yl)oxy)methyl)piperidin-1-yl)(6-methyl-3-(pyrimidin-2-yl)pyridin-2-yl)methanone, (4,4-difluoro-2-(((5-(trifluoromethyl)pyridin-2-yl)oxy)methyl)piperidin-1-yl)(6-methyl-3-(pyrimidin-2-yl)pyridin-2-yl)methanone (enantiomer A).

It will be understood that, as used herein, references to the compounds of Formula (I) (Ia) (Ib) are meant to also include the pharmaceutically acceptable salts or derivatives thereof.

Furthermore, the compound of the formula (I) (Ia), (Ib) may form an acid addition salt or a salt with a base, depending on the kind of the substituents, and these salts are included in the present invention, as long as they are pharmaceutically acceptable salts.

The terms "the compound of the invention" and "the compounds of the present invention" and "the compounds of Formula (I)" refer to each of the compounds of Formulae (I), (Ia), (Ib), and are meant to include their pharmaceutically acceptable salts, hydrates, solvates, and crystalline forms and also any suitable forms as illustrated hereinafter.

As used herein, the term "salt" refers to any salt of a compound according to the present invention prepared from an inorganic or organic acid or base, quaternary ammonium salts and internally formed salts. Physiologically or pharmaceutically acceptable salts are particularly suitable for medical applications because of their greater aqueous solubility relative to the parent compounds. Such salts must clearly have a physiologically acceptable anion or cation. Suitably physiologically or pharmaceutically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects.

Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

The compounds (I), (Ia), (Ib) of the invention may be in crystalline forms. In certain embodiments, the crystalline forms of the compounds (I) (Ia), (Ib) are polymorphs. Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers or in one or more tautomeric forms. Accordingly, in certain embodiments, the compound of the Formulae (I) (Ia), (Ib) may exist in the form of other tautomers or geometrical isomers in some cases, depending on the kinds of the substituents. In the present specification, the compound may be described in only one form of such isomers, but the present invention includes such isomers, isolated forms of the isomers, or a mixture thereof. Furthermore, the compound of the Formulae (I) (Ia) (Ib) may have asymmetric carbon atoms or axial asymmetries in some cases, and correspondingly, it may exist in the form of optical isomers such as an (R)-form, an (S)-form, and the like. The present invention includes within its scope all such isomers, including racemates, enantiomers and mixtures thereof.

In particular, within the scope of the present invention are included all stereoisomeric forms, including enantiomers, diastereoisomers, and mixtures thereof, including racemates and the general reference to the compounds of formulae (I), (Ia), (Ib), include all the stereoisomeric forms, unless otherwise indicated.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

According to another aspect of the present invention a process for the preparation of the compounds of Formula (I) is provided.

In certain embodiments a process for the preparation of a compound of Formula (Ia) is provided, said process comprising the following steps represented in the synthetic scheme below:

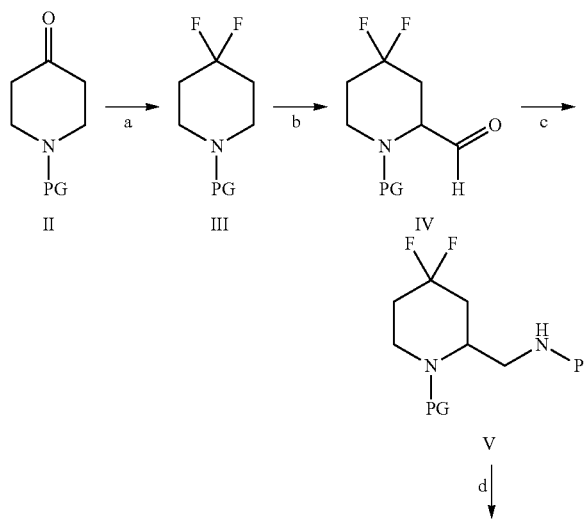

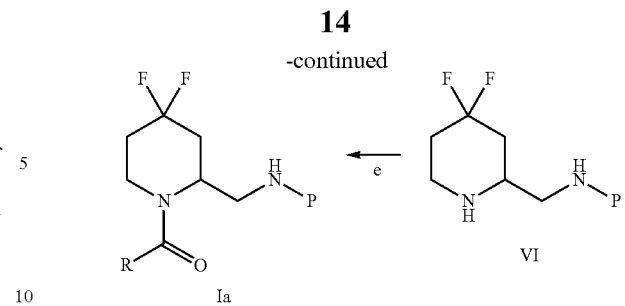

a) reacting a compound of Formula (II), where PG is preferably the BOC group, with a fluorinating agent to obtain a compound of Formula (II);

b) reacting a compound of Formula (III) with strong bases and dimethylformamide, thus obtaining a compound of Formula (IV);

c) adding an amine of Formula P—NH$_2$, where P is selected from the group consisting of pyridyl, pyrimidyl, pyrazyl, pyridazyl, quinolyl, isoquinolyl, being such P optionally substituted with one or more substituents selected from the group consisting of (C$_1$-C$_3$)alkyl, halogen, trifluoromethyl, cyano, in the presence of a reducing agent to obtain a compound of Formula (V);

d) cleaving the protecting group (PG), preferably the BOC group, from the compound of Formula (V) to obtain a compound of Formula (VI);

e) reacting a compound of Formula (VI) with RCOOH in the presence of coupling reagents or with the corresponding acyl chlorides RCOCl in the presence of a base, where R is selected from a 5- or 6-membered aromatic ring and a 5- or 6-membered heteroaromatic ring containing 1 to 3 heteroatoms selected from S, O e N, such ring being substituted with one or two substituents selected from the group consisting of (C$_1$-C$_3$)alkyl, (C$_3$-C$_5$)cycloalkoxy, (C$_1$-C$_3$)alkyl-carbonyl, cyano, trifluoromethyl, phenyl optionally substituted with one or more halogen atoms, a 5- or 6-membered heterocycle containing at least one nitrogen atom.

In further embodiments, the invention concerns a process for the preparation of a compound of Formula (Ia) which comprises the following steps represented in the scheme below:

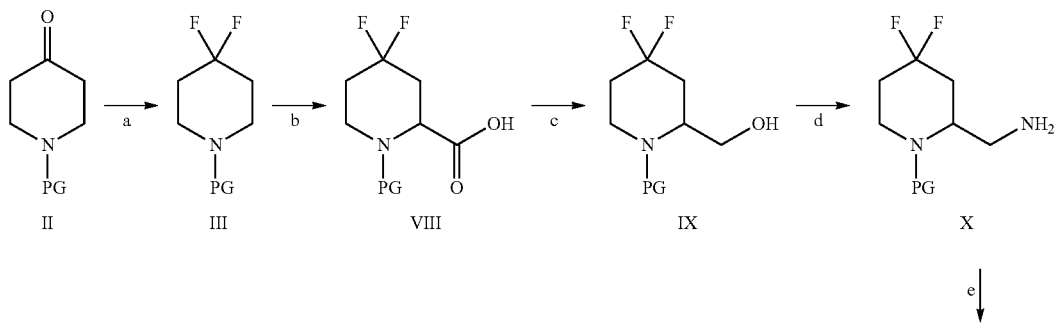

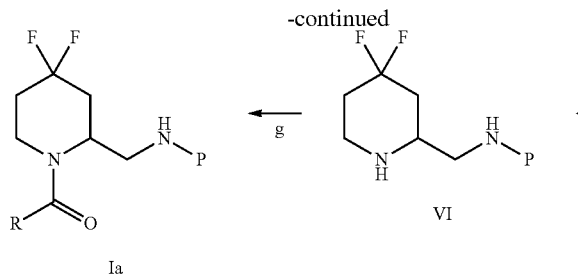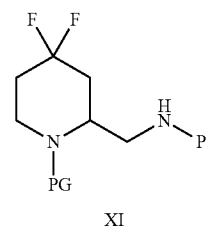

a) reacting a compound of Formula (II), where PG is preferably the BOC group, with a fluorinating agent to obtain a compound of Formula (III);
b) reacting a compound of Formula (II) with strong bases and $CO_2$, thus obtaining a compound of Formula (VIII);
c) reacting a compound of formula (VIII) with a reducing agent to obtain a compound of Formula (IX);
d) reacting a compound of formula (IX) with phtalimide and hydrazine to obtain a compound of formula (X)
e) reacting a compound of formula (X) with P—Cl or P—F where P is selected from the group consisting of pyridyl, pyrimidyl, pyrazyl, pyridazyl, quinolyl, isoquinolyl, being such P optionally substituted with one or more substituents selected from the group consisting of $(C_1-C_3)$alkyl, halogen, trifluoromethyl, cyano, in the presence of a base to obtain a compound of formula (XI)
f) cleaving the protecting group (PG), where PG is preferably the BOC group, from the compound of Formula (XI) to obtain a compound of Formula (VI);
g) reacting a compound of Formula (VI) with RCOOH in the presence of coupling reagents or with the corresponding acyl chlorides RCOCl in the presence of a base, where R is selected from a 5- or 6-membered aromatic ring and a 5- or 6-membered heteroaromatic ring containing 1 to 3 heteroatoms selected from S, O e N, such ring being substituted with one or two substituents selected from the group consisting of $(C_1-C_3)$alkyl, $(C_3-C_5)$cycloalkoxy, $(C_1-C_3)$alkylcarbonyl, cyano, trifluoromethyl, phenyl optionally substituted with one or more halogen atoms, a 5- or 6-membered heterocycle containing at least one nitrogen atom.

In a further embodiment, the invention concerns a process for the preparation of a compound of Formula (Ib) which comprises the following steps represented in the scheme below:

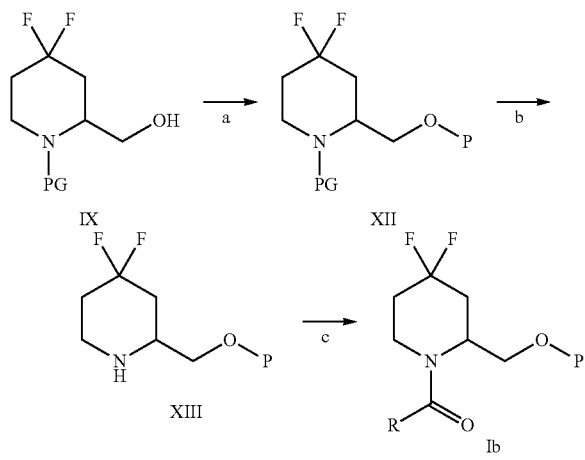

a) reacting a compound of formula (IX) with P—Cl or P—F where P is selected from the group consisting of pyridyl, pyrimidyl, pyrazyl, pyridazyl, quinolyl, isoquinolyl, quinoxalyl, being such P optionally substituted with one or more substituents selected from the group consisting of $(C_1-C_3)$ alkyl, halogen, trifluoromethyl, cyano, in the presence of a base to obtain compound of formula (XII);
b) cleaving the protecting group (PG) where PG typically is the BOC group from the compound of Formula (XII) to obtain a compound of Formula (XIII);
c) reacting a compound of Formula (XIII) with RCOOH in the presence of coupling reagents or with the corresponding acyl chlorides RCOCl in the presence of a base, where R is selected from a 5- or 6-membered aromatic ring and a 5- or 6-membered heteroaromatic ring containing 1 to 3 heteroatoms selected from S, O e N, such ring being substituted with one or two substituents selected from the group consisting of $(C_1-C_3)$alkyl, $(C_3-C_5)$cycloalkoxy, $(C_1-C_3)$alkylcarbonyl, cyano, trifluoromethyl, phenyl optionally substituted with one or more halogen atoms, a 5- or 6-membered heterocycle containing at least one nitrogen atom.

The compounds of formula (I) (Ia) (Ib) or their pharmaceutically acceptable salts can be used as medicaments, in particular as antagonists of the Orexin receptors.

In accordance with a fourth aspect of the invention, pharmaceutical compositions comprising a compound of formula (I) (Ia), (Ib) and a pharmaceutically acceptable carrier and/or excipient are provided.

In certain embodiments the compounds of formula (I) are used in combination with a pharmaceutically acceptable carrier and, optionally, with suitable excipients, to obtain pharmaceutical compositions. The term "pharmaceutically acceptable carrier" means solvents, carrier agents, diluting agents and the like which are usually used in the administration of pharmaceutical compounds.

In certain embodiments, the pharmaceutical compositions of the invention are administered by parenteral, oral, buccal, sublingual, nasal, rectal, topical or transdermal administration.

In certain embodiments, the pharmaceutical compositions of the invention may be in solid or liquid form.

The pharmaceutical compositions in solid form may contain suitable excipients such as fillers, lubricants, binding agents, wetting agents, disintegrants, colorants and flavouring agents and mixtures thereof. For example the tablets may contain pre-gelatinised starch, microcrystalline cellulose, sodium glycolate starch, talc, lactose, magnesium stearate, sucrose, stearic acid, mannitol.

The pharmaceutical compositions in liquid form, typically may be provided as solutions, suspensions, emulsion, syrups, elixir. Typically, the compositions in liquid form may contain suspending agents, emulsifying agents, carriers, preservatives and colorants, flavouring agents.

Compositions of this invention suitable for the oral administration will be conveniently discrete units such as tablets, capsules, cachet, powders or pellets, or as liquid suspension.

The tablets can contain also suitable excipients routinely used in pharmaceutical field such as pre-gelatinised starch, microcrystalline cellulose, sodium glycolate starch, talc, lactose, magnesium stearate, sucrose, stearic acid, mannitol. Compositions for parenteral administration typically include sterile preparations. Compositions for topical administration may typically be formulated as creams, pastes, oils, ointments, emulsions, foams, gels, drops, spray solutions and transdermal patches.

In accordance with certain embodiments, the present invention provides for a pharmaceutical composition comprising a compound of formula (I) or (Ia), (Ib) in association with an additional active ingredient and a pharmaceutically acceptable excipient.

Said additional active ingredients may be an additional compound of formula (I) or a different chemical entity having similar or different activity.

The compounds of the present invention may be administered in combination with other compounds which are known in the art to be useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, GABA agonists, 5HT-2 antagonists including 5HT-2A antagonists and 5HT-2A/2C antagonists, histamine antagonists including histamine R3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium chalmel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, dorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation. In another embodiment, the subject compound may be employed in combination with other compounds which are known in the art, either administered separately or in the same pharmaceutical compositions, include, but are not limited to: (a) insulin sensitizers including (i) PPARy antagonists such as glitazones (e.g. ciglitazone; darglitazone; englitazone; isaglitazone (MCC-555); pioglitazone; rosiglitazone; troglitazone; tularik; BRL49653; CLX-0921; 5-BTZD), GW-0207, LG-100641, and LY-300512, and the like; (ii) biguanides such as metfonnin and phenfonnin; (b) insulin or insulin mimetics, such as biota, LP-IOO, novarapid, insulin detemir, insulin lispro, insulin glargine, insulin zinc suspension (lente and ultralente); Lys-Pro insulin, GLP-I (73-7) (insulintropin); and GLP-I (7-36)-NH2); (c) sulfonylureas, such as acetohexamide; chlorpropamide; diabinese; glibenclamide; glipizide; glyburide; glimepiride; gliclazide; glipentide; gliquidone; glisolamide; tolazamide; and tolbutamide; (d) a-glucosidase inhibitors, such as acarbose, adiposine; camiglibose; emiglitate; miglitol; voglibose; pradimicinQ; salbostatin; CKD-711; MDL-25,637; MDL-73,945; and MOR 14, and the like; (e) cholesterol lowering agents such as (i) HMG-CoA reductase inhibitors (atorvastatin, itavastatin, fluvastatin, lovastatin, pravastatin, rivastatin, rosuvastatin, simvastatin, and other statins), (H) bile acid 25 absorbers/sequestrants, such as cholestyramine, colestipol, dialkylaminoalkyl derivatives of a cross-linked dextran; Colestid®; LoCholest®, and the like, (ii) nicotinyl alcohol, nicotinic acid or a salt thereof, (iii) proliferator-activater receptor a agonists such as fenofibric acid derivatives (gemfibrozil, clofibrate, fenofibrate and benzafibrate), (iv) inhibitors of cholesterol absorption such as stanol esters, beta-sitosterol, sterol glycosides such as tiqueside; and azetidinones such as ezetimibe, and the like, and acyl CoA:cholesterol acyltransferase (ACAT inhibitors such as avasimibe, and melinamide, (v) anti-oxidants, such as probucol, (vi) vitamin E, and (vii) thyromimetics; (f) PPARa agonists such as biclofibrate, benzafibrate, ciprofibrate, clofibrate, etofibrate, fenofibrate, and gemfibrozi; and other fibric acid derivatives, such as Atromid®, Lopid® and Tricor®, and the like, and PPARa agonists as described in WO 97/36579 by Glaxo; (g) PPARS agonists; (h) PPAR a/S agonists, such as muraglitazar, and the compounds disclosed in U.S. Pat. No. 6,414,002; and (i) anti-obesity agents, such as (1) growth hormone secretagogues, growth hormone secretagogue receptor agonists/antagonists, such as NN703, hexarelin, MK-0677, SM-130686, CP-424,391, L-692,429, and L-I 63,255; (2a) protein tyrosine phosphatase-IB (PTP-IB) inhibitors; 130686, CP-424,391, L-692,429, and L-I63, 255; (2b) protein tyrosine phosphatase-IB (PTP-IB) inhibitors; (3) cannabinoid receptor ligands, such as cannabinoid CB 1 receptor antagonists or 5 inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentennine, and sibutramine; (5) adrenoreceptor agonists, such as AD9677/TAK677 (DainipponTakeda), CL-316,243, SB 418790, BRL-37344, L-796568, BMS-196085, BRL-35135A, CGPI2177A, BTA-243, 10 Trecadrine, ZenecaD7114, SR 59119A; (6) pancreatic lipase inhibitors, such as orlistat (Xenical®), Triton WR1339, RHC80267, lipstatin, tetrahydrolipstatin, teasaponin, diethylumbelliferyl phosphate; (7) neuropeptide Y 1 antagonists, such as BIBP3226, J-115814, BIBO 3304, LY-357897, CP-671906, GI-264879A; (8) neuropeptide Y5 antagonists, such as GW-569180A, GW-594884A, GW-587081X, GW-548118X, FR226928, PR 240662, FR252384, 1229U91, GI-264879A, CGP71683A, LY-377897, PD-160170, SR-120562A, SR-120819A and JCF-104; (9) melanin-concentrating hormone (MCR) receptor antagonists; (10) melanin-concentrating hormone 1 receptor (MCRIR) antagonists, such as T-226296 (Takeda); (11) melanin-concentrating hormone 2 receptor (MCH2R) agonist/antagonists; (13) serotonin reuptake inhibitors such as fluoxetine, paroxetine, and sertraline; (14) melanocortin agonists, such as Melanotan II; (15) other Mc4r (melanocortin 4 receptor) agonists, such as CHIR86036 (Chiron), ME-I0142, and ME-10145 (Melacure), CHIR86036 (Chiron); PT-141, and PT-14 (Palatin); (16) 5HT-2 agonists; (17) 5HT2C (serotonin receptor 2C) agonists, such as BVT933, DPCA37215, WAY161503, R-I065; (18) galanin antagonists; (19) CCK25 agonists: (20) CCK-A (cholecystokinin-A) agonists, such as AR-R 15849, GI 181771, JMV-180, A-71378, A-71623 and SR14613; (22) corticotropin-releasing hormone agonists; (23) histamine receptor-3 (H3) modulators; (24) histamine receptor-3 (H3) antagonists/inverse agonists, such as hioperamide, 3-(1H-imidazol-4-yl)propy 1N-(4-pentenyl)carbamate, clobenpropit, iodophenpropit, imoproxifan, GT2394 (Gliatech), and O-[3-(1H-imidazol-4-yl)propanol]-carbamates; (25) J3-hydroxy steroid dehydrogenase-I inhibitors (p-HSD-1); 26) PDE (phosphodiesterase) inhibitors, such as theophylline, pentoxifylline, zaprinast, sildenafil, amrinone, milrinone, cilostamide, rolipram, and cilomilast; (27) phosphodiesterase-3B (PDE3B) inhibitors; (28) NE (norepinephrine) transport inhibitors, such as GW 320659, despiramine, talsupram, and nomifensine; (29) ghrelin receptor antagonists; (30) leptin, including recombinant human leptin (PEG-OB, Hoffman La Roche) and recombinant methionyl human leptin (Amgen); (31) leptin derivatives; (32) BRS3 (bombesin receptor subtype 3) agonists such as [D-Phe6, betaAlall, Phe13, Nle14]Bn(6-14) and [D-Phe6,Phe13]Bn (6-13)propylamide, and those compounds disclosed in Pept. Sci. 2002 August; 8(8): 461-75); (33) CNTF (Ciliary neurotrophic factors), such as 01-181771 (GlaxoSmithKline), SR146131 (Sanofi Synthelabo), butabindide, PDI70,292, and PD 149164 (Pfizer); (34) CNTF derivatives, such as axokine (Regeneron); (35) monoamine reuptake inhibitors, such as sibutramine; (36) UCP-I (uncoupling protein-I), 2, or 3 activators, such as phytanic acid, 4-[(E)-2-(5,6,7,8-tetrahydro-S,5,8,8-tetramethyl 1-2-napthalenyl)-1-propenyl]benzoic acid (TTNPB), retinoic acid; (37) thyroid hormone p. agonists, such as KB-2611 (KaroBioBMS); (38) F AS (fatty acid synthase) inhibitors, such as Cerulenin and C75; (39) 10 DOAT 1 (diacylglycerol acyltransferase 1) inhibitors; (40) DGA T2 (diacylglycerol acyltransferase 2) inhibitors; (41) ACC2 (acetyl-CoA carboxylase-2) inhibitors; (42) glucocorticoid antagonists; (43) acyl-estrogens, such as oleoyl-estrone, disclosed in del MarGrasa, M. et al., Obesity Research, 9:202-9 (2001); (44) dipeptidyl peptidase IV (DP-IV) inhibitors, such as isoleucine thiazolidide, valine pyrrolidide, NVP-DPP728, LAF237, MK-431, 15 P93/01, TSL 225, TMC-2AJ2B/2C, FE 999011, P93101K364, VIP 0177, SDZ 274-444; (46) dicarboxylate transporter inhibitors; (47) glucose transporter inhibitors; (48) phosphate transporter inhibitors; (49) Metfonnin (Glucophage®); and (50) Topiramate (Topimax®); and (50) peptide YY, PYY 3-36, peptide YY analogs, derivatives, and fragments such as BIM-43073D, BIM-43004C (Olitvak, D. A. et al., Dig. Dis. Sci. 44(3):643-48 (1999>>; (51) Neuropeptide Y2 (NPY2) receptor agonists such NPY3-36, N acetyl [Leu(28, 31)]NPY 24-36, TASP-V, and cyclo-(28/32)-Ac-[Lys28-Glu32]-(25-36)-pNPY; (52) Neuropeptide Y4 (NPY4) agonists such as pancreatic peptide (PP), and other Y4 agonists such as 1229U91; (54) cyclooxygenase-2 inhibitors such as etoricoxib, celecoxib, valdecoxib, parecoxib, lumiracoxib, BMS347070, tiracoxib or JTE522, ABT963, CS502 and GW406381, and pharmaceutically acceptable salts thereof; (55) Neuropeptide YI (NPYI) antagonists such as BIBP3226, J-115814, BIBO 3304, LY-357897, CP-671906, GI-264879A; (56) Opioid antagonists such as nalmefene (Revex®), 3-methoxynaltrexone, naloxone, naltrexone; (57) 1113 HSD-I (II-beta hydroxy steroid dehydrogenase type 1) inhibitor such as BVT 3498, BVT 2733; (58) aminorex; (59) amphechloral; (60) amphetamine; (61) benzphetamine; (62) chlorphentermine; (63) clobenzorex; (64) cloforex; (65) clominorex; (66) clortermine; (67) cyclexedrine; (68) dextroamphetamine; (69) diphemethoxidine, (70) N-ethylamphetamine; (71) fenbutrazate; (72) fenisorex; (73) fenproporex; (74) fludorex; (75) fluminorex; (76) furfurylmethylamphetamine; (77) levamfetamine; (78) levophacetoperane; (79) mefenorex; (80) metamfepramone; (81) methamphetamine; (82) norpseudoephedrine; (83) pentorex; (84) phendimetrazine; (85) 35 phenmetrazine; (86) picilorex; (87) phytopharm 57; and (88) zonisamide.

In another embodiment, the subject compound may be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotrophin releasing factor (CRF) antagonists, a-adrenoreceptor antagonists, neurokinin-I receptor antagonists, atypical anti-depressants, benzodiazepines, 5-HT1A agonists or antagonists, especially 5-HT1A partial agonists, and corticotropin releasing factor (CRF) antagonists.

Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide; venlafaxine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts thereof.

In another embodiment, the subject compound may be employed in combination with anti-Alzheimer's agents; beta-secretase inhibitors; gamma-secretase inhibitors; growth hormone secretagogues; recombinant growth hormone; HMG-CoA reductase inhibitors; NSAID's including ibuprofen; vitamin E; anti-amyloid antibodies; CB-I receptor antagonists or CB-I receptor inverse agonists; antibiotics such as doxycycline and rifampin; N-methyl-Daspartate (NMDA) receptor antagonists, such as memantine; cholinesterase inhibitors such asgalantamine, rivastigmine, donepezil, and tacrine; growth hormone secretagogues such as ibutamoren, ibutamoren mesylate, and capromorelin; histamine H3 antagonists; AMP A agonists; PDE IV inhibitors; GABAA inverse agonists; or neuronal nicotinic agonists.

In another embodiment, the subject compound may be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amitriptyline, amobarbital, amoxapine, bentazepam, benzoctamine, brotizolam, bupropion, busprione, butabarbital, butalbital, capuride, carbocloral, chloral betaine, chloral hydrate, chiordiazepoxide, clomipramine, clonazepam, cloperidone, clorazepate, clorethate, dozapine, cyprazepam, desipramine, dexclamol, diazepam, dichloralphenazone, divalproex, diphenhydramine, doxepin, estazolam, ethchlorvynol, etomidate, fenobam, flunitrazepam, flurazepam, fluvoxamine, fluoxetine, fosazepam, glutethimide, halazepam, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, reclazepam, roletamide, secobarbital, sertraline, suproclone, temazepam, thioridazine, tracazolate, tranylcypromaine, trazodone, triazolam, trepipam, tricetamide, triclofos, trifluoperazine, trimetozine, trimipramine, uldazepam, venlafaxine, zaleplon, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

Lisuride and pramipexol are commonly used in a non-salt form. In another embodiment, the subject compound may be employed in combination with acetophenazine, alentemol, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, risperidone, sulpiride, tetrabenazine, trihexyphenidyl, thioridazine or thiothixene.

In another embodiment, the subject compound may be employed in combination with a compound of the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol.

An example of a diphenylbutylpiperidine is pimozide.

An example of an indolone is molindolone. Other neuroleptic agents include loxapine, sulpiride and risperidone.

It will be appreciated that the neuroleptic agents when used in combination with The subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form.

In another embodiment, the subject compound may be employed in combination with an anoretic agent such as aminorex, amphechloral, amphetamine, benzphetamine, chlorphentermine, clobenzorex, cloforex, clominorex, clortermine, cyclexedrine, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, norpseudoephedrine, pentorex, phendimetrazine, phenmetrazine, phentennine, phenylpropanolamine, picilorex and sibutramine; selective serotonin reuptake inhibitor (SSRI); halogenated amphetamine derivatives, including chlorphentennine, cloforex, clortennine, dexfenfluramine, fenfluramine, picilorex and sibutramine; and pharmaceutically acceptble salts thereof. In another embodiment, the subject compound may be employed in combination with an opiate agonist, a lipoxygenase inhibitor, such as an inhibitor of 5-lipoxygenase, a cyclooxygenase inhibitor, such as a cyclooxygenase-2 inhibitor, an interleukin inhibitor, such as an interleukin-I inhibitor, an NMDA antagonist, an inhibitor of nitric oxide or an inhibitor of the synthesis of nitric oxide, a non-steroidal antiinflammatory agent, or a cytokine-suppressing antiinflammatory agent, for example with a compound such as acetaminophen, asprin, codiene, fentanyl, ibuprofen, indomethacin, ketorolac, morphine, naproxen, phenacetin, piroxicam, a steroidal analgesic, sufentanyl, sunlindac, tenidap, and the like. Similarly, the subject compound may be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedrine, or levo-desoxy-ephedrine; an antiitussive such as codeine, hydrocodone, caramiphen, carbetapentane, or dextramethorphan; a diuretic; and a sedating or non-sedating antihistamine. The production of the pharmaceutical compositions can be effected in a manner which will be familiar to any person skilled in the art (see for example Remington, The Science and Practice of Pharmacy, 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

In accordance with a fifth aspect the present invention provides for the use of the compound of Formula (I), (Ia), (Ib) as a medicament. In certain aspects, the present invention also relates to a method for the prevention or treatment of a disease or disorder mentioned herein comprising administering to a subject a pharmaceutically effective amount of a compound of formula (I) (Ia) (Ib).

In treatment methods according to the invention, an effective amount of a compound of formula (I) or pharmaceutical composition containing the same according to the invention is administered to a subject suffering from or diagnosed as having such disease, disorder or condition.

An "effective amount" means an amount or dose sufficient to generally bring about the desired therapeutic or prophylactic benefit in patients in need of such treatment for the designated disease, disorder or condition. Effective amounts or doses of the compounds of the present invention may be ascertained by routine methods such as modelling, dose escalation studies or clinical trials, and by taking into consideration routine factors, e.g., the mode or route of administration or drug delivery, the pharmacokinetics of the compound, the severity and course of the disease, disorder, or condition, the subject's previous or ongoing therapy, the subject's health status and response to drugs, and the judgment of the treating physician. An example of a dose is in the range of from about 0.001 to about 200 mg of compound per kg of subject's body weight per day, preferably about 0.05 to 100 mg/kg/day, or about 1 to 35 mg/kg/day, in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms. For avoidance of any doubt, if compounds are described as useful for the prevention or treatment of certain diseases, such compounds are likewise suitable for use in the preparation of a medicament for the prevention or treatment of said diseases.

It is to be understood that reference to a treatment includes both treatment of established symptoms and prophylactic treatment, unless explicitly stated otherwise.

The compounds according to formula (I) (Ia) (Ib) are useful for the prevention or treatment of diseases related to the orexin system.

Such diseases related to the orexin system include all types of sleep disorders, of stress-related syndromes, of addictions (especially psychoactive substance use, abuse, seeking and reinstatement), of cognitive dysfunctions in the healthy population and in psychiatric and neurologic disorders, of eating or drinking disorders.

In certain embodiments, such diseases related to the orexin system may be selected from the group consisting of sleep disorders that comprises all types of insomnias, narcolepsy and other disorders of excessive sleepiness, sleep-related dystonias, restless leg syndrome, sleep apneas, jet-lag syndrome, shift-work syndrome, delayed or advanced sleep phase syndrome or insomnias related to psychiatric disorders (notably all types of insomnias, especially primary insomnia).

In certain embodiments, such diseases related to the orexin system may be selected from the group consisting of cognitive dysfunctions that comprise deficits in all types of attention, learning and memory functions occurring transiently or chronically in the normal, healthy, young, adult or aging population, and also occurring transiently or chronically in psychiatric, neurologic, cardiovascular and immune disorders.

In certain embodiments, such diseases related to the orexin system may be selected from the group consisting of eating disorders that comprise metabolic dysfunction; dysregulated appetite control; compulsive obesities; emeto-bulimia or anorexia nervosa.

In certain embodiments, such diseases related to the orexin system may be selected from the group consisting of all types of addictions (especially psychoactive substance use, abuse, seeking and reinstatement) that comprise all types of psychological or physical addictions and their related tolerance and dependence components.

Eating disorders may be defined as comprising metabolic dysfunction; dysregulated appetite control; compulsive obesities; emeto-bulimia or anorexia nervosa.

Pathologically modified food intake may result from disturbed appetite (attraction or aversion for food); altered energy balance (intake vs. expenditure); disturbed perception of food quality (high fat or carbohydrates, high palatability); disturbed food availability (unrestricted diet or deprivation) or disrupted water balance. Drinking disorders include polydipsias in psychiatric disorders and all other types of excessive fluid intake.

Sleep disorders include all types of parasomnias, insomnias, narcolepsy and other disorders of excessive sleepiness, sleep-related dystonias; restless leg syndrome; sleep apneas; jet-lag syndrome; shift-work syndrome, delayed or advanced sleep phase syndrome or insomnias related to psychiatric disorders. Insomnias are defined as comprising sleep disorders associated with aging; intermittent treatment of chronic insomnia; situational transient insomnia (new environment, noise) or short-term insomnia due to stress; grief; pain or illness. Insomnia also include stress-related syndromes including post-traumatic stress disorders as well as other types and subtypes of anxiety disorders such as generalized anxiety, obsessive compulsive disorder, panic attacks and all types of phobic anxiety and avoidance.

Addictions may be defined as addiction to one or more rewarding stimuli, notably to one rewarding stimulus. Such rewarding stimuli may be of either natural or synthetic origin. Psychoactive substance use, abuse, seeking and reinstatement are defined as all types of psychological or physical addictions and their related tolerance and dependence components.

Cognitive dysfunctions include deficits in all types of attention, learning and memory functions occurring transiently or chronically in the normal, healthy, young, adult or aging population, and also occurring transiently or chronically in psychiatric, neurologic, cardiovascular and immune disorders. Besides, any characteristics described in this invention for the compounds of formula (I) (whether for the compounds themselves, salts thereof, compositions containing the compounds or salts thereof, uses of the compounds or salts thereof, etc.) apply mutatis mutandis to compounds of formula (Ia) and (Ib).

The invention will be now detailed by means of the following examples relating to the preparation of some embodiments of the compounds (I) of the invention and to the evaluation of their activity against Orexin-1 ($OX_1$) receptor and Orexin-2 ($OX_2$) receptor.

In the procedure that follows, after the starting materials, reference to a description is typically provided. The starting material may not necessarily have been prepared from the description referred to. The stereochemistry of the Examples has been assigned on the assumption that the absolute configuration centers are retained.

Reagents used in the following examples were commercially available from various suppliers (for example Sigma-Aldrich, Acros or Apollo scientific) and used without further purifications. Solvents were used in dry form. Reactions in anhydrous environment were run under a positive pressure of dry $N_2$.

Microwave reactions were run on a Biotage Initiator 2.5 instrument.

Proton Nuclear Magnetic Resonance (1H NMR) spectra were recorded on Bruker Avance 400 MHz instrument. Chemical shifts are reported in ppm (δ) using the residual solvent line as internal standard. Splitting patterns are designated as: s, singlet; d, doublet; t, triplet; q, quartet; m, multiplet; b, broad signal.

Mass spectra (MS) were run on a Ion Trap Thermo LCQ classic spectrometer, operating in positive ES(+) and negative ES(−) ionization mode.

UPLC spectra were performed on a Waters Acquity UPLC-SQD instrument using an Acquity UPLC-BEH C18 column (1.7 μM, 50×2.1 mm).

Purifications by means of preparative chiral HPLC were performed using a Shimadzu Preparative Liquid Chromatograph LC-8A apparatus and a UV detector SPD-20A. The cromatographic methods were the following:

A: Column: DAICEL IC 5 μM (250×4.6 mm) mobile phase 80% Heptane+0.1% DEA 20% 2-propanol; flow rate of 0.5 ml/min; UV 254 nm.

B: Column: DAICEL AD-H 5 μM (250×4.6 mm) mobile phase 60% Heptane+0.1% DEA 40% ethanol; flow rate of 0.5 ml/min; UV 254 nm.

C: Column: DAICEL IC 5 μM (250×4.6 mm) mobile phase 70% Heptane+0.1% DEA 30% ethanol; flow rate of 0.5 ml/min; UV 254 nm.

D: Column DAICEL AD-H 5 μM (250×4.6 mm) mobile phase 60% Heptane+0.1% DEA 40% 2-propanol; flow rate of 0.5 ml/min; UV 254 nm.

E: Column: DAICEL IC 5 μM (250×4.6 mm) mobile phase 70% Heptane+0.1% DEA 30% 2-propanol; flow rate of 0.5 ml/min; UV 254 nm.

F: Column DAICEL AD-H 5 μM (250×4.6 mm) mobile phase 80% Heptane+0.1% DEA 20% 2-propanol; flow rate of 0.5 ml/min; UV 254 nm.

G: Column: DAICEL IC 5 μM (250×4.6 mm) mobile phase 60% Heptane+0.1% DEA 40% 2-propanol; flow rate of 0.5 ml/min; UV 254 nm.

H: Column DAICEL AD-H 5 μM (250×4.6 mm) mobile phase 70% Heptane+0.1% DEA 30% 2-propanol; flow rate of 0.5 ml/min; UV 254 nm.

I: Column Regis WELK 01(SS) 5 μM (250×4.6 mm) mobile phase 80% Heptane+0.1% DEA 20% 2-propanol; flow rate of 0.5 ml/min; UV 254 nm.

L: Column DAICEL AD-H 5 μM (250×4.6 mm) mobile phase 80% Heptane+0.1% DEA 20% Ethanol; flow rate of 0.5 ml/min; UV 254 nm.

M: Column DAICEL AD-H 5 μM (250×4.6 mm) mobile phase 90% Heptane+0.1% DEA 10% 2-propanol; flow rate of 0.5 ml/min; UV 254 nm.

Flash silica gel chromatography was performed on Biotage automatic flash chromatography systems (Sp1 and Isolera systems) using Biotage silica cartridges.

Thin layer chromatography was carried out using Merck TLC plates Kieselgel 60F-254, visualized with UV light, aqueous permanganate solution, iodine vapours.

The following abbreviations are used herein: DEAD: diethylazodicarboxylate; DIPEA: N,N-diisopropylethylamine; HOBT: hydroxybenzotriazole hydrate; Boc: terbutyloxycarbonyl; DCM: dichloromethane; TFA: trifluoroacetic acid; DAST: (diethylamino)sulfur trifluoride; TMEDA: N,N,N',N'-Tetramethylethylenediamine; DMF: dimethylformamide; NMP: N-methyl pyrrolidinone; THF: tetrahydrofuran; EDCl: N-(3-Dimethylaminopropyl)-N'-ethylcarbodiimide; HBTU: O-(Benzotriazol-1-yl)-N,N,N',N'-tetramethyluronium hexafluorophosphate; RT: room temperature; dppf: 1,1'-Bis(diphenylphosphino)ferrocene.

Example 1

Preparation of Intermediate 1: tert-butyl 4,4-difluoropiperidine-1-carboxylate

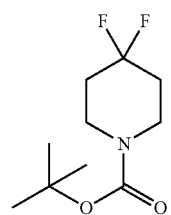

To a solution of tert-butyl 4-oxopiperidine-1-carboxylate (10 g; 0.05 mol) in dry DCM (80 ml) at −40° C., DAST (3 eq) was added, then 4 hours at −20° C. Mixture was allowed to reach RT then poured in satd. NaHCO3 aq. solution and extracted with DCM (3×70 ml), washed with water and dried. Yield 95% light yellow oil.

1HNMR (CDCl3) δ ppm=3.52-3.58 (m, 4H), 1.87-2.0 (m, 4H), 1.49 (br. s, 9H).

Example 2

Preparation of Intermediate 2: (±) 1-(tert-butoxycarbonyl)-4,4-difluoropiperidine-2-carboxylic acid

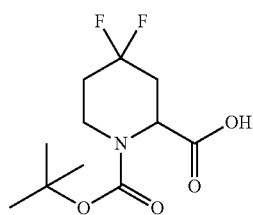 [SMILES: CC(C)(C)OC(=O)N1CCC(F)(F)CC1C(=O)O]

Intermediate 1 (2 g, 9.04 mmol) was dissolved in dry Et2O (100 ml), the solution cooled to −78° C. and TMEDA (2.45 ml; 16.3 mmol) was added. secBuLi (1.4M in cyclohexane; 11.6 ml; 16.3 mmol) was dropped in 30'; after 90' at −78° C. the reaction was warmed to −40° C., maintained at this temperature for 30' then cooled at −78° C. CO2 was bubbled for 10', reaction was allowed to reach RT (in about 1 h). A saturated aqueous solution of NH4Cl (100 ml) was slowly added, then reaction washed with Et2O (50 ml), the pH of aqueous phase was adjusted to 5 and extracted with ethyl acetate (3×40 ml), dried (Na2SO4) and evaporated to obtain a cream white solid (1.6 g).

MS (ESI) m/z: 264 [M−H]−.

1HNMR (CDCl3) δ ppm=8.33 (br.s., 1H), 4.98-5.15 (m, 1H), 4.10-4.25 (m, 1H), 3.25-3.40 (m, 1H), 2.65-2.80 (m, 1H), 2.02-2.25 (m, 2H), 1.80-1.98 (m, 1H), 1.49 (br.s., 9H).

Example 3

Preparation of Intermediate 3: (±) tert-butyl 4,4-difluoro-2-(hydroxymethyl)piperidine-1-carboxylate

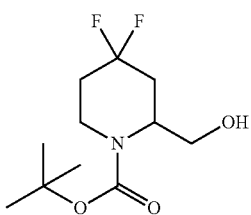 [SMILES: CC(C)(C)OC(=O)N1CCC(F)(F)CC1CO]

The solution of intermediate 2 (3.5 g; 13.19 mmol) in dry THF (100 ml) was cooled to 0° C., then BH3 (THF complex, 1M in THF; 26.4 ml; 26.4 mmol) was dropped in 30'. After 3 h at 0° C. and 3 h at RT the reaction was slowly poured in MeOH (100 ml) and evaporated. Crude was dissolved in MeOH and evaporated again to obtain a colourless oil (3.21 g).

MS (ESI) m/z: 252 [M+H]+.

1HNMR (CDCl3) δ ppm=4.40-4.48 (m, 1H), 4.05-4.10 (m, 1H), 3.75-3.80 (m, 1H), 3.65-3.69 (m, 1H), 3.10-3.19 (m, 1H), 1.80-2.16 (m, 5H), 1.49 (br.s., 9H).

Example 4

Preparation of Intermediate 4: (±) tert-butyl 4,4-difluoro-2-formylpiperidine-1-carboxylate

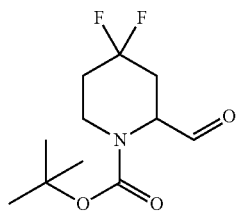 [SMILES: CC(C)(C)OC(=O)N1CCC(F)(F)CC1C=O]

Intermediate 1 (6 g, 0.27 mol) was dissolved in dry Et2O (250 ml), the solution cooled to −78° C. and TMEDA (7.5 ml; 0.486 mol) was added. secBuLi (1.4M in cyclohexane; 36 ml; 0.486 mol) was dropped in 30'; after 90' at −78° C. the reaction was warmed to −40° C., maintained at this temperature for 30' then cooled at −78° C. DMF (4.2 ml; 0.54 mol) was added, reaction was allowed to reach RT (in about 1 h). A saturated aqueous solution of NH4Cl (100 ml) was slowly added, then reaction was extracted with Et2O (3×75 ml), the organic solvent was dried (Na2SO4) and evaporated to obtain a crude (yellow oil) that was used directly in the next step (Example 7).

1HNMR (CDCl3) δ ppm=9.59 (s, 1H), 4.60-4.80 (m, 1H), 3.95-4.45 (m, 1H), 3.10-3.45 (m, 1H), 2.57-2.70 (m, 1H), 1.80-2.27 (m, 3H), 1.50 (br. s, 9H).

Example 5

Preparation of Intermediate 5: (±) tert-butyl 2-((1,3-dioxoisoindolin-2-yl)methyl)-4,4-difluoropiperidine-1-carboxylate

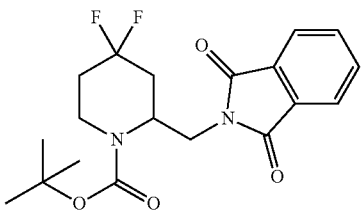 [SMILES: CC(C)(C)OC(=O)N1CCC(F)(F)CC1CN1C(=O)c2ccccc2C1=O]

Intermediate 3 (3.2 g; 12.7 mmol), phthalimide (3 g; 20.78 mmol) and PPh3 (5.3 g; 20.78 mmol) were dissolved in dry THF under N2 atmosphere. The resultant solution was cooled at 0° C. then DEAD (40% in toluene; 8.8 ml; 20.78 mmol) was added dropwise. The mixture was stirred at 0° C. for 30 min, then at RT overnight. H2O was added (5 ml) and then the solvent was evaporated under reduced atmosphere. The residue was taken up with AcOEt (50 ml) and the solution was washed with H2O and brine (2×100 ml). The organic layers were dried with Na2SO4, filtrated and evaporated; crude was purified on silica gel (Cyclohexane/AcOEt=9/1). Yield 2.83 g white solid.

1HNMR (CDCl3) δ ppm=7.91-7.82 (m, 2H), 7.73 (br. s., 2H), 4.87 (br. s., 1H), 4.35-4.05 (m, 2H), 3.58-3.48 (m, 1H), 3.45 (br. s., 1H), 2.22-1.78 (m, 4H), 1.09 (br. s., 9H).

Example 6

Preparation of Intermediate 6: (±) tert-butyl 2-(aminomethyl-4,4-difluoropiperidine-1-carboxylate

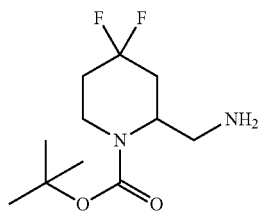 [SMILES: CC(C)(C)OC(=O)N1CCC(F)(F)CC1CN]

Intermediate 5 (2.8 g; 7.36 mmol) was dissolved in ethanol (50 ml), hydrazine hydrate (1.8 ml; 36.8 mmol) was added. After 48 h at RT the reaction was filtered, the white solid washed with ethanol; solvent was evaporated, residue treated with Et2O/isopropanol 1/1 (20 ml), filtered and evaporated to give 1.24 g of the title compound as yellow oil.

1HNMR (CDCl3) δ ppm=4.37-4.42 (m, 1H), 4.18-4.25 (m, 1H), 2.85-3.10 (m, 2H), 2.72-2.79 (m, 1H), 2.10-2.22 (m, 1H), 1.75-2.08 (m, 3H), 1.49 (br. s., 9H).

Example 7

Preparation of Intermediate 7: (±) tert-butyl 2-(((5-chloropyridin-2-yl)amino)methyl)-4,4-difluoropiperidine-1-carboxylate

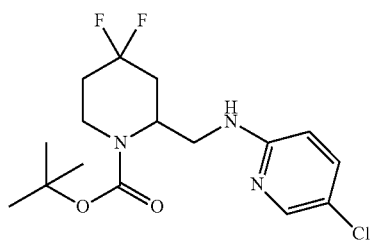 [SMILES: CC(C)(C)OC(=O)N1CCC(F)(F)CC1CNc1ccc(Cl)cn1]

Crude (±) tert-butyl 4,4-difluoro-2-formylpiperidine-1-carboxylate (Intermediate 4; 0.27 mol) was dissolved in dichloroethane (50 ml), then acetic acid (5 eq) and -amino 5 chloropyridine (3.4 g, 0.27 mol) were added. After 1.5 hours at room temperature NaBH(OAc)3 (9 g, 0.43 mol) was added and the reaction was maintained under stirring at room temperature for 18 hours. The reaction was poured in aqueous NaHCO3 and extracted with DCM. The organic layers were combined, dried (Na2SO4) and concentrated under vacuum; the crude was purified by silica gel column chromatography (DCM to DCM/ethyl acetate=95/5) to obtain 1.43 g of intermediate 7 as light yellow solid.

MS (ESI) m/z: 262 [M+H]+.

1HNMR (CDCl3) δ ppm=8.04 (d, J=2.8 Hz, 1H), 7.35 (dd, J=8.8 and 2.8 Hz, 1H), 6.35 (d, J=8.8 Hz, 1H), 4.71-4.77 (m, 2H), 4.18-4.21 (m, 1H), 3.69-3.72 (m, 1H), 3.34-3.37 (m, 1H), 3.08-3.12 (m, 1H), 1.90-2.17 (m, 4H), 1.40 (b.s, 9H).

Example 8

Preparation of Intermediate 8: (±)tert-butyl 4,4-difluoro-2-(((5-(trifluoromethyl)pyridin-2-yl)amino)methyl)piperidine-1-carboxylate

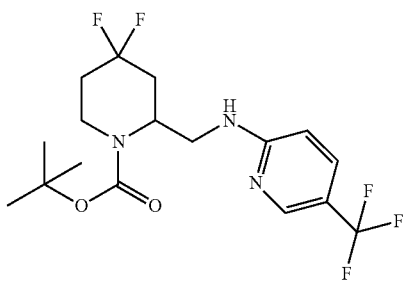 [SMILES: CC(C)(C)OC(=O)N1CCC(F)(F)CC1CNc1ccc(C(F)(F)F)cn1]

A mixture of intermediate 6 (32 mg; 0.128 mmol), 2-chloro-5-(trifluoromethyl)-pyridine (23 mg; 0.128 mmol) and potassium carbonate (35 mg; 0.255 mmol) in dry DMF (2 ml) was stirred under nitrogen for 10 minutes. The reaction was performed with microwave oven: 2 cycles at 100° C. for 5 min; 1 cycle at 120° C. for 20 min; 2 cycles at 120° C. for 40 min.

DMF was evaporated under reduced pressure, then the residue was taken up in NaHCO3 (sat. solution; 15 ml) and extracted with AcOEt (3×15 ml). The organic layers were collected, washed in with water, dried with Na2SO4 anhydrous (20 g) and filtrated. Then the solvent was evaporated under reduced pressure. Crude was purified by silica gel column (cyclohexane 100% to cyclohexane/AcOEt 90:10). Yield 19 mg (light yellow solid).

MS (ESI) m/z: 396 [M+H]+.

1HNMR (CDCl3) δ ppm=8.36 (s, 1H), 7.57 (dd, J=2.2, 8.6 Hz, 1H), 6.42 (d, J=8.8 Hz, 1H), 5.07 (br. s., 1H), 4.80 (td, J=5.3, 10.4 Hz, 1H), 4.19 (br. s., 1H), 3.82 (br. s., 1H), 3.43 (br. s., 1H), 3.13 (t, J=13.2 Hz, 1H), 2.23-1.81 (m, 4H), 1.39 (s, 9H).

Example 9

Preparation of Intermediate 9: (±)tert-butyl 4,4-difluoro-2-(((3-fluoro-5-(trifluoromethylpyridin-2-yl)amino)methyl)piperidine-1-carboxylate

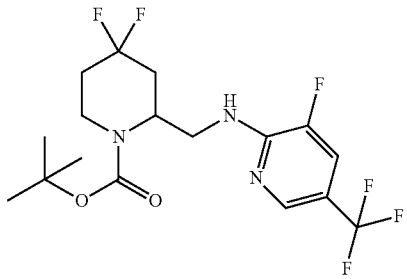 [SMILES: CC(C)(C)OC(=O)N1CCC(F)(F)CC1CNc1ncc(C(F)(F)F)cc1F]

A mixture of intermediate 6 (140 mg; 0.565 mmol), 2,3-difluoro-5-(trifluoromethyl)-pyridine (103 mg; 0.565 mmol) and potassium carbonate (156 mg; 1.123 mmol) in dry DMF (2 ml) was stirred under nitrogen for 10 minutes. The reaction was performed with microwave oven: 1 cycle at 80° C. for 10 min; 1 cycle at 80° C. for 5 min.

DMF was evaporated under reduced pressure, then the residue was taken up in NaHCO3 (sat. solution; 10 ml) and extracted with AcOEt (3×15 ml). The organic layers were collected, washed in with water, dried with Na2SO4 anhydrous and filtrated, then the solvent was evaporated under reduced pressure. Crude was purified by silica gel column (cyclohexane 100% to cyclohexane/AcOEt 90:10). Yield 115 mg (light yellow solid).

MS (ESI) m/z: 414 [M+H]+.

1HNMR (CDCl3) δ ppm=8.18 (s, 1H), 7.32 (dd, J=1.7, 11.0 Hz, 1H), 5.32 (s, 1H), 4.84 (br. s., 1H), 4.21 (br. s., 1H), 3.99 (br. s., 1H), 3.52 (d, J=14.2 Hz, 1H), 3.17 (t, J=13.2 Hz, 1H), 2.24-2.01 (m, 3H). 2.01-1.81 (m, 1H), 1.42-1.33 (m, 9H).

Example 10

Preparation of Intermediate 10: (±)tert-butyl 2-(((4,6-dimethylpyrimidin-2-yl)amino)methyl)-4,4-difluoropiperidine-1-carboxylate

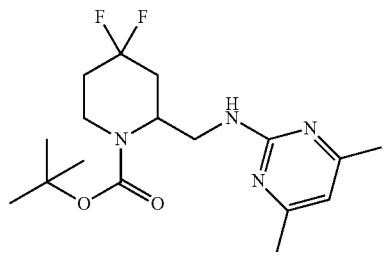 [SMILES: Cc1cc(C)nc(NCC2CC(F)(F)CCN2C(=O)OC(C)(C)C)n1]

A mixture of intermediate 6 (60 mg; 0.24 mmol), 2-chloro-4,6-dimethylpyrimidine (55 mg; 0.38 mmol) and DIPEA (90 µl; 0.50 mmol) in isopropanol (1.5 ml) was stirred under nitrogen for 10 minutes. The reaction was performed with microwave oven: 2 cycles at 120° C. for 30 min; 1 cycle at 160° C. for 30 min; 2 cycles at 180° C. for 30 min.

Crude was poured in water (10 ml) and extracted with DCM (3×15 ml). The organic layers were collected, washed in with water, dried with Na2SO4 anhydrous (20 g) and filtrated. Then the solvent was evaporated under reduced pressure. Crude was purified with silica gel column (DCM 100% to DCM/AcOEt 70:30). Yield 17 mg (light yellow solid).

MS (ESI) m/z: 357 [M+H]+.

1HNMR (CDCl3) δ ppm=6.32 (s, 1H), 4.75-4.76 (m, 1H), 4.18-4.21 (m, 1H), 3.85-3.86 (m, 1H), 3.45-3.48 (m, 1H), 3.10-3.22 (m, 1H), 2.29 (s, 6H), 1.36 (s, 9H).

Example 11

Preparation of Intermediate 11: (±) tert-butyl 2-(((5-cyanopyridin-2-yl)amino)methyl)-4,4-difluoropiperidine-1-carboxylate

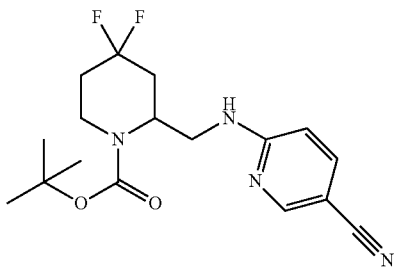 [SMILES: CC(C)(C)OC(=O)N1CCC(F)(F)CC1CNc1ccc(C#N)cn1]

A mixture of intermediate 6 (100 mg; 0.4 mmol), 6-chloronicotinonitrile (83 mg; 0.60 mmol) and potassium carbonate (195 mg; 1.40 mmol) in dry DMF was stirred under nitrogen for 10 minutes. The reaction was performed with microwave oven: 1 cycle at 140° C. for 15 min; 1 cycle at 150° C. for 20 min. DMF was evaporated under reduced pressure, then the residue was taken up in NaHCO3 (sat. solution; 15 ml) and extracted with AcOEt (3×15 ml). The organic layers were collected, washed in with water, dried with Na2SO4 anhydrous (20 g) and filtrated. Solvent was evaporated under reduced pressure to obtain a crude that was purified with silica gel column (DCM 100% to DCM/AcOEt 90:10) and utilized in example 18.

Example 12

Preparation of Intermediate 12: tert-butyl 4,4-difluoro-2-(((5-(trifluoromethyl)pyrazin-2-yl)amino)methyl)piperidine-1-carboxylate

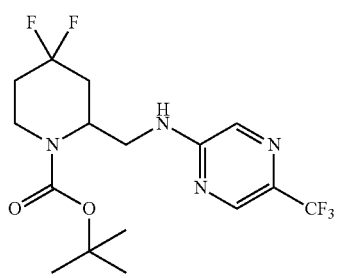 [SMILES: CC(C)(C)OC(=O)N1CCC(F)(F)CC1CNc1cnc(C(F)(F)F)cn1]

A mixture of intermediate 6, 2-chloro-5-(trifluoromethyl)-pyrazine and potassium carbonate in NMP was stirred under nitrogen for 10 minutes. The reaction was subjected to microwaves: 1 cycle at 120° C. for 15 min.

NaHCO3 (sat. solution; 20 mL) was added and the solution was extracted with AcOEt (3×20 mL). The organic layers were collected, washed in with water, dried with Na2SO4 anhydrous and filtrated. Then the solvent was evaporated under reduced pressure and the crude purified by column chromatography eluting with cyclohexane/AcOEt 95:5 to obtain 44.6 mg of the desired compound (brown solid; 40%).

MS (ESI) m/z: 397 [M+H]+.

1H NMR (CDCl3) δ=8.34 (s, 1H), 7.90 (s, 1H), 5.44 (br. s., 1H), 4.82 (br. s., 1H), 4.27-4.09 (m, 1H), 3.98 (br. s., 1H), 3.44 (br. s., 1H), 3.16 (t, J=13.4 Hz, 1H), 2.22-2.02 (m, 3H), 2.01-1.80 (m, 1H), 1.38 (s, 9H).

Example 13

Preparation of Intermediate 13: (±) tert-butyl 4,4-difluoro-2-(((5-(trifluoromethyl)pyridine-2-yl)oxy)methyl)piperidine-1-carboxylate

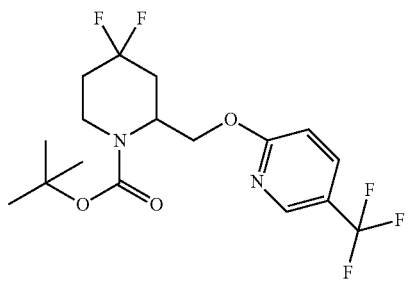 [SMILES: CC(C)(C)OC(=O)N1CCC(F)(F)CC1COc1ccc(C(F)(F)F)cn1]

A mixture of intermediate 3 (70 mg; 0.28 mmol), NaH 60%(14 mg: 0.36 mmol) and 2-chloro-5-(trifluoromethyl)-pyridine (66 mg; 0.36 mmol) in dry DMF (0.5 ml) was stirred at RT for 5 hours. Reaction was poured in water (20 ml) and extracted with DCM (3×20 ml). The organic layers were collected, washed in with water, dried with Na2SO4 anhydrous (20 g) and filtrated. Solvent was evaporated under reduced pressure to obtain the title compound which was utilized as such in example 19.

Example 14

Preparation of Intermediate 14: (±) 5-chloro-N-((4,4-difluoropiperidin-2-yl)methyl)pyridin-2-amine

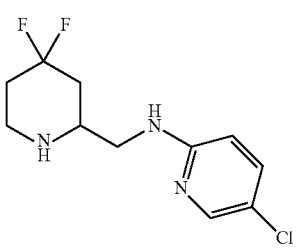 [SMILES: FC1(F)CCNC(CNc2ccc(Cl)cn2)C1]

Intermediate 7 (1.23 g; 3.4 mmol) dissolved in dry DCM (10 ml) was cooled to 0° C.; TFA (2 ml) was added. After 3 hours at RT solvents were evaporated and residue was treated with NaOH 2N (30 ml) and extracted with DCM (3×50 ml). Organic solvent was dried (Na2SO4) and evaporated to give intermediate 14 as a light yellow oil (yield 95%).

MS (ESI) m/z: 262 [M+H]+.

1HNMR (CDCl3) δ ppm=9.28 (s, 1H), 8.20-8.25 (m, 2H), 6.67-6.70 (dd, J 4, 1 Hz, 1H), 3.64-3.66 (m, 1H), 3.22-3.28 (m, 1H), 2.94-3.01 (m, 1H), 1.79-2.08 (m, 3H).

Example 15

Preparation of Intermediate 15: (±)N-((4,4-difluoropiperidin-2-yl)methyl)-5-(trifluoromethyl)pyridine-2-amine

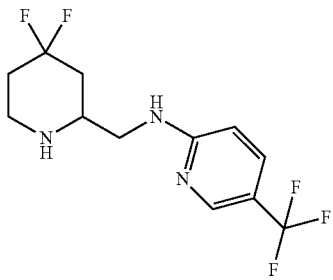 [SMILES: FC1(F)CCNC(CNc2ccc(C(F)(F)F)cn2)C1]

Intermediate 8 (200 mg; 0.5 mmol) dissolved in dry DCM (1 ml) was cooled to 0° C.; TFA (500 µl) was added. After 3 hours at RT solvents were evaporated and residue was treated with NaOH 2N (10 ml) and extracted with DCM (3×10 ml). Organic solvent was dried (Na2SO4) and evaporated to give intermediate 15 as a light yellow oil (yield 90%).

MS (ESI) m/z: 296 [M+H]+.

1HNMR (CDCl3) δ ppm=8.36 (s, 1H), 7.60 (dd, J=2.0, 8.8 Hz, 1H), 6.47 (d, J=8.8 Hz, 1H), 5.17 (br. s., 1H), 3.52 (td, J=4.8, 13.8 Hz, 1H), 3.39 (td, J=6.8, 13.7 Hz, 1H), 3.22-3.14 (m, 1H), 3.10 (dt, J=3.9, 7.6 Hz, 1H), 2.91-2.82 (m, 1H), 2.20-2.03 (m, 2H), 1.91-1.73 (m, 1H), 1.71-1.57 (m, 1H).

Example 16

Preparation of Intermediate 16: (±)N-((4,4-difluoropiperidin-2-yl)methy)-3-fluoro-5-(trifluoromethyl)pyridine-2-amine

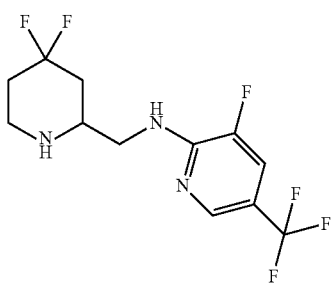 [SMILES: Fc1cc(C(F)(F)F)cnc1NCC1CC(F)(F)CCN1]

Intermediate 9 (113 mg, 0.273 mmol) was dissolved in a mixture of TFA/DCM 3/1 (2 ml) and stirred at RT for 1 hour. MeOH (2 ml) was added then the reaction mixture was loaded on SCX cartridge (2 g) eluting with methanol then NH3 2M in methanol. Intermediate 16 was obtained as light yellow solid (73 mg).

MS (ESI) m/z: 314 [M+H]+.

1HNMR (CDCl3) δ ppm=8.19 (s, 1H), 7.34 (dd, J=2.0, 10.8 Hz, 1H), 5.36 (br. s., 1H), 3.65 (td, J=4.9, 13.7 Hz, 1H), 3.54 (td, J=6.7, 13.6 Hz, 1H), 3.23-3.08 (m, 2H), 2.87 (dt, J=2.9, 12.7 Hz, 1H), 2.21-2.02 (m, 2H), 1.92-1.73 (m, 1H), 1.71-1.57 (m, 1H).

Example 17

Preparation of Intermediate 17: (±)N-((4,4-difluoropiperidin-2-yl)methyl)-4,6-dimethylpyrimidin-2-amine

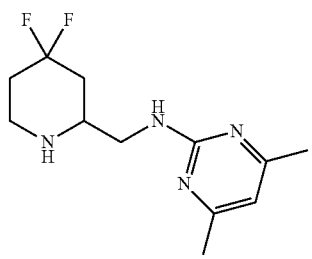 [SMILES: Cc1cc(C)nc(NCC2CC(F)(F)CCN2)n1]

Intermediate 10 (17 mg; 0.047 mmol) dissolved in dry DCM (0.5 ml) was cooled to 0° C.; TFA (400 µl) was added. After 2 hours at RT solvents were evaporated and residue was purified on SCX cartridge (MeOH then NH3 2N in MeOH). Intermediate 17 was obtained as light yellow solid (11 mg).

MS (ESI) m/z: 257 [M+H]+.

Example 18

Preparation of Intermediate 18: (±) 6-(((4,4-difluoropiperidin-2-yl)methyl)amino)nicotinonitrile

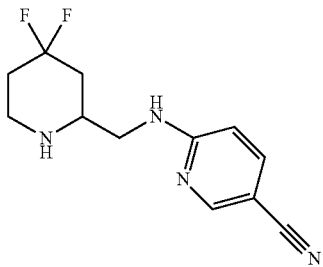 [SMILES: N#Cc1ccc(NCC2CC(F)(F)CCN2)nc1]

Intermediate 11 (20 mg; 0.085 mmol) dissolved in dry DCM (0.5 ml) was cooled to 0'C; TFA (400 µl) was added. After 3 hours at RT solvents were evaporated and residue was treated with NaOH 2N (10 ml) and extracted with DCM (3×10 ml). Organic solvent was dried (Na2SO4) and evaporated to give a crude that was purified on silica gel column (DCM 100% to DCM-MeOH=95/5). Intermediate 18 was obtained as light yellow solid (10 mg).

MS (ESI) m/z: 253 [M+H]+.

Example 19

Preparation of Intermediate 19: (±) 2-((4,4-difluoropiperidin-2-yl)methoxy)-5-(trifluoromethyl)pyridine

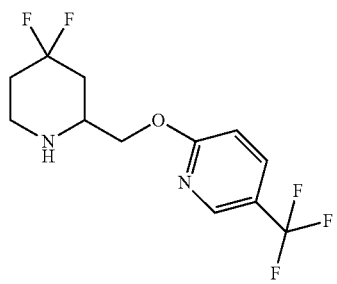 [SMILES: FC1(F)CCNC(COc2ccc(C(F)(F)F)cn2)C1]

Intermediate 13 (50 mg; 0.126 mmol) dissolved in dry DCM (2 ml) was cooled to 0° C.; TFA (1 ml) was added. After 3 hours at RT solvents were evaporated and residue was treated with NaOH 2N (20 ml) and extracted with DCM (3×15 ml). Organic solvent was dried (Na2SO4) and evaporated to give a crude that was purified on silica gel column (DCM-AcOEt=80/20). Intermediate 19 was obtained as light yellow solid (30 mg).

MS (ESI) m/z: 297 [M+H]+.

Example 20

Preparation of Intermediate 20: (±)N-((4,4-difluoropiperidin-2-yl)methyl)-5-(trifluoromethyl)pyrazin-2-amine

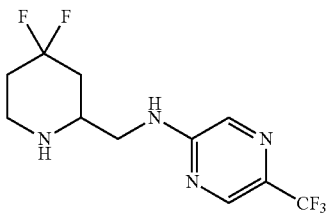 [SMILES: FC1(F)CCNC(CNc2cnc(C(F)(F)F)cn2)C1]

Intermediate 12 was dissolved in a solution of trifluoroacetic acid and DCM 3:1 and the mixture was stirred at Rt for 30 min. MeOH was added (1 ml) and the reaction mixture loaded on SCX 1 g; Eluent MeOH then Ammonia (2M in MeOH); the desired compound was obtained as brown solid. (yield 95.5%, 30 mg).

MS (ESI) m/z: 297 [M+H]+.

1HNMR (CDCl3) δ ppm=8.34 (s, 1H), 7.90 (s, 1H), 5.44 (br. s., 1H), 4.82 (br. s., 1H), 4.14-4.17 (m, 1H), 3.98 (br. s., 1H), 3.44 (br. s., 1H), 3.16 (t, J=13.4 Hz, 1H), 2.22-2.02 (m, 3H), 2.01-1.80 (m, 1H), 1.38 (s, 9H).

Example 21

Preparation of Intermediate 21: methyl 2-bromo-5-nitrobenzoate

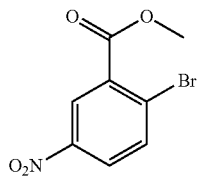

2-bromo-5-nitrobenzoic acid (4 g, 0.016 mol) was dissolved in MeOH (20 ml) and sulphuric acid (1 ml) was added. The reaction was refluxed for 3 h then cooled at RT. Water (20 ml) was added and the solid was filtered, dissolved in DCM and washed with saturated aqueous solution of NaHCO3. The organic solvent was dried (Na2SO4) and evaporated. Intermediate 21 was obtained as white solid (2.83 g).

MS (ESI) m/z: 231 [M+H]+.
1HNMR (CDCl3) δ ppm=8.67 (d, 1H), 8.18 (dd, 1H), 7.90 (d, 1H), 4.02 (s, 3H).

Example 22

Preparation of Intermediate 22: methyl 2-phenyl-5-nitrobenzoate

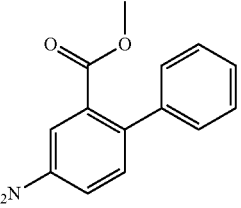

Intermediate 19 (1.56 g; 6 mmol), phenylboronic acid (0.81 g; 6.6 mmol), Na2CO3 (0.95 g; 9 mmol), and Pd(PPh3)4 (0.035 g; 0.03 mmol) were dissolved in DME (6.5 ml) and water (4 ml). The reaction was refluxed for 4 h then cooled to RT. The mixture was poured into water and extracted with ethyl acetate (3×25 ml); the organic solvent was dried with Na2SO4, filtrated and evaporated. Intermediate 20 was obtained as light yellow oil (1.6 g).

MS (ESI) m/z: 265 [M+H]+.
1HNMR (CDCl3) δ ppm=8.71 (d, 1H), 8.39 (dd, 1H), 7.59 (d, 1H), 7.47 (m, 3H), 7.35 (m, 2H), 3.74 (s, 3H).

Example 23

Preparation of Intermediate 23: methyl 2-phenyl-5-aminobenzoate

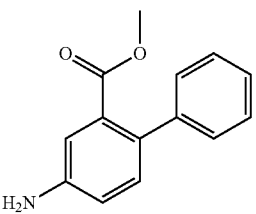 [SMILES: COC(=O)c1cc([N+](=O)[O-])ccc1-c1ccccc1]

Intermediate 21 (1.6 g; 6 mmol) was suspended in MeOH (40 ml) then Pd/C (10%, 0.128 g, 0.12 mmol) was added. The mixture was saturated with H2 for 2 h at 1.5 bar then was filtrated and evaporated. Crude was purified on silica gel (DCM/MeOH=95/5) to obtain 1.15 g of the title compound.

MS (ESI) m/z: 228 [M+H]+.

Example 24

Preparation of Intermediate 24: methyl N,N-di-methyl-2-phenyl-5-aminobenzoate

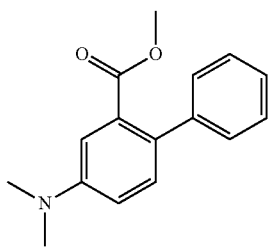 [SMILES: COC(=O)c1cc(N(C)C)ccc1-c1ccccc1]

Intermediate 23 (570 mg; 2.5 mmol), HCHO (35% in water, 5.85 ml; 25 mmol), AcOH (0.84 ml) and NaBH(OAc)3 (0.88 g; 4.15 mmol) were dissolved in dry DCM (35 ml) under N2 atmosphere. The resultant solution was stirred for 2 h at RT then further NaBH(OAc)3 (0.88 g; 4.15 mmol) was added. The mixture was stirred at RT overnight, then H2O was added (35 ml) followed by Na2CO3 until pH=8. The organic solvent was dried with Na2SO4, filtrated and evaporated; the crude that was purified on silica gel column (Cyclohexane/AcOEt=1/1) to obtain 90 mg of the title compound.

MS (ESI) m/z: 257 [M+H]+.

Example 25

Preparation of Intermediate 25: N,N-di-methyl-2-phenyl-5-aminobenzoic acid

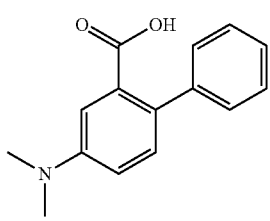 [SMILES: CN(C)c1ccc(-c2ccccc2)c(C(=O)O)c1]

Intermediate 24 (90 mg; 0.35 mmol) was dissolved in MeOH (5 ml) and aqueous NaOH (2N, 2 ml, 4 mmol) was added. The resultant solution was stirred for 48 h at RT then HCl (1N, 4 ml) was added followed by MeOH (35 ml). The precipitate was filtered and the filtrate was evaporated to obtain 70 mg of the title compound.

MS (ESI) m/z: 243 [M+H]+.

1HNMR (DMSO-d6) δ ppm=7.45 (m, 1H), 7.37 (m, 2H), 7.29 (m, 3H), 7.15 (m, 2H), 3.00 (s, 6H).

Example 26

Preparation of Intermediate 26: methyl 2-bromo-5-chlorobenzoate

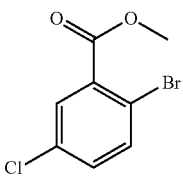

2-bromo-5-chlorobenzoic acid (4 g, 0.016 mol) was dissolved in MeOH (20 ml) and sulphuric acid (1 ml) was added. The reaction was refluxed for 3 h then cooled at RT. Water (20 ml) was added and the solid was filtered, dissolved in DCM and washed with saturated aqueous solution of NaHCO3. The organic solvent was dried (Na2SO4) and evaporated to obtain 4.17 g of the title compound as oil.

1HNMR (CDCl3) δ ppm=7.81 (d, 1H), 7.61 (d, 1H), 7.33 (dd, 1H), 3.96 (s, 3H).

Example 27

Preparation of Intermediate 27: methyl 5-chloro-2-(pyrimidin-2-yl)benzoate

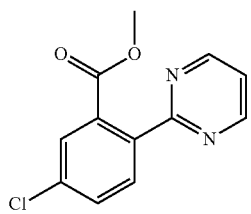 [SMILES: COC(=O)c1cc(Cl)ccc1-c1ncccn1]

Intermediate 26 (2 g, 8 mmol) was dissolved dry DMF (15 ml), then CsF (16 mmol), CuI (1.6 mmol), [Ph3P]4Pd (0.8 mmol) and pyrimidine-2-tributylstannane (12 mmol; prepared according to Eur. J. Org. Chem. 2003, 1711-1721) were added. The mixture was warmed at 130° C. for 10 minutes (microwave), then poured in aqueous saturated solution of NH4Cl and extracted with AcOEt (3×50 ml). The organic layers were combined, dried (Na2SO4) and concentrated under vacuum; crude product was purified by silica gel column chromatography (DCM to DCM/MeOH 9/1) to give 1.5 g of the title compound as white solid.

MS (ESI) m/z: 249 [M+H]+.

1HNMR (CDCl3) δ ppm=8.82 (d, 2H), 8.07 (d, 1H), 7.71 (d, 1H), 7.57 (dd, 1H), 7.27 (t, 1H), 3.80 (s, 3H).

Example 28

Preparation of Intermediate 28: 5-chloro-2-(pyrimidin-2-yl)benzoic acid

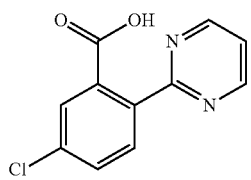 [SMILES: O=C(O)c1cc(Cl)ccc1-c1ncccn1]

Intermediate 27 (300 mg; 1.2 mmol) was dissolved in MeOH (5 ml) and aqueous NaOH (2N, 2 ml, 4 mmol) was added. The resultant solution was stirred overnight at RT then solvents were evaporated. HCl (1N, 4 ml) was added to the residue, the precipitate was collected and washed with water. 280 mg of the title compound were obtained as white solid.

MS (ESI) m/z: 235 [M+H]+.

1HNMR (CDCl3) δ ppm=8.91 (d, 2H), 8.26 (d, 1H), 8.17 (d, 1H), 7.63 (dd, 1H), 7.41 (t, 1H).

Example 29

Preparation of Intermediate 29: methyl 5-cyano-2-(pyrimidin-2-yl)benzoate

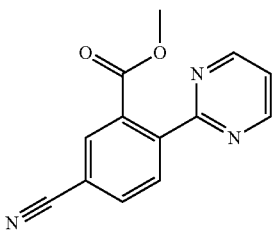 [SMILES: COC(=O)c1cc(C#N)ccc1-c1ncccn1]

Intermediate 27 (250 mg; 1 mmol), K3Fe(CN)6 (92 mg; 0.25 mmol), Pd(OAc)2 (0.45 mg; 0.002 mmol), dppf (1.12 mg; 0.002 mmol) and Na2CO3 (106 mg; 1 mmol) were dissolved in dry NMP (1 ml) under N2 atmosphere. The resultant solution was heated for 1 h at 180° C. in the microwave oven then further Pd(OAc)2 (0.45 mg; 0.002 mmol) and dppf (1.12 mg; 0.002 mmol) were added. The mixture was heated for 2 h at 170° C. in the microwave oven, then H2O was added (35 ml) and the product extracted with DCM (2×50 ml). The organics were dried, filtrated and evaporated; crude was purified on silica gel (Cyclohexane/AcOEt=1/1) to obtain 80 mg of the title compound as light yellow oil.

MS (ESI) m/z: 240 [M+H]+.

1HNMR (CDCl3) δ ppm=8.87 (d, 2H), 8.23 (d, 1H), 8.02 (d, 1H), 7.87 (dd, 1H), 7.33 (t, 1H), 3.82 (s, 3H).

Example 30

Preparation of Intermediate 30: 5-cyano-2-(pyrimidin-2-yl)benzoic acid

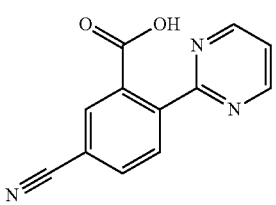 [SMILES: N#Cc1ccc(-c2ncccn2)c(C(=O)O)c1]

Intermediate 29 (80 mg; 0.33 mmol) was dissolved in THF (2 ml), MeOH (2 ml), water (1 ml) and LiOH.H2O (28 mg; 0.66 mmol) were added. The mixture was stirred for 2 h at RT then evaporated. HCl (1N, 4 ml) was added to the residue and the product extracted with AcOEt (2×5 ml). The organic solvent was dried, filtrated and evaporated to obtain 43 mg of the title compound as white cream solid.

MS (ESI) m/z: 226 [M+H]+.

1HNMR (CDCl3) δ ppm=8.94 (d, 2H), 8.37 (d, 1H), 8.35 (d, 1H), 7.93 (dd, 1H), 7.45 (t, 1H).

Example 31

Preparation of Intermediate 31: methyl 6-methyl-3-phenylpicolinate

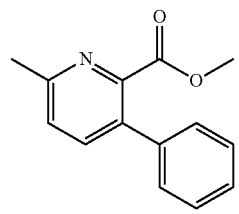 [SMILES: COC(=O)c1nc(C)ccc1-c1ccccc1]

To a suspension of methyl-3-iodo-6-methylpyridine-2-carboxylate (1 g, 3.6 mmol; prepared according to WO2010063663), Phenyl Boronic Acid (440 mg, 3.6 mmol) and Pd Tetrakistriphenylphospine (417 mg; 0.36 mmol) in dry Toluene (12 ml) was added K2CO3 1M aq solution (3.6 ml, 3.6 mmol). The mixture was heated in microwave oven for 5 min at 120° C. (procedure was repeated for 4 times). To promote the reaction were added further Tetrakistriphenylphospine palladium (208.5 mg; 0.18 mmol)) and Phenyl Boronic Acid (220 mg, 0.18 mmol). The mixture was subject to 2 cycles of microwave heating at 140° C. for 10 min. The reaction mixture was diluted with AcOEt (10 ml) and water (10 ml). The organic layer was separated, washed with brine, dried with Na2SO4 and filtrated. The solvent was evaporated under reduced pressure, crude was purified on silica gel (Cyclohexane to Cyclohexane/AcOEt 9:1) to obtain 506 mg of the title compound as yellow oil.

MS (ESI) m/z: 228 [M+H]+.

1HNMR (CDCl3) δ ppm=7.67 (d, J=7.8 Hz, 1H), 7.47-7.33 (m, 6H), 3.77 (s, 3H), 2.68 (s, 3H).

Example 32

Preparation of Intermediate 32: 6-methyl-3-phenylpicolinic acid

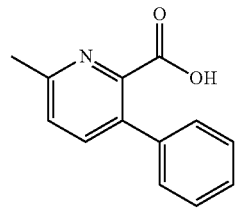 [SMILES: Cc1ccc(-c2ccccc2)c(C(=O)O)n1]

To a solution of intermediate 31 (505 mg; 2.22 mmol) in 1,4-dioxane-water (3/1; 12 ml) LiOH.H2O (140 mg; 3.33 mmol) was added, then the solution was heated at 70° C. for 1 hour.

Solvents were evaporate under reduced pressure, residue taken up with 5 ml of brine, the resultant solution acidified to pH 2 with HCl 1N and extracted with AcOEt (4×20 ml).

The organic layers were collected, dried with Na2SO4 and evaporated to obtain 480 mg of the title compound as white solid.

MS (ESI) m/z: 214 [M+H]+.

1HNMR (DMSO-d6) δ ppm=13.21 (br. s., 1H), 7.76 (d, J=7.8 Hz, 1H), 7.48-7.35 (m, 6H), 2.53 (s, 3H).

Example 33

Preparation of Intermediate 33: 3-chloro-6-(trifluoromethyl)picolinic acid

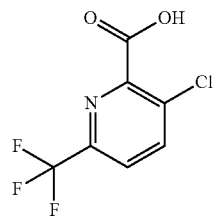 [SMILES: O=C(O)c1nc(C(F)(F)F)ccc1Cl]

Prepared from 5-chloro-2-(trifluoromethyl)pyridine (1.81 g, 10 mmol) as described in Tetrahedron 60 (2004) 11869-11874. Yield 2.2 g oil (98%)

Example 34

Preparation of Intermediate 34: methyl 3-chloro-6-(trifluoromethyl)picolinate

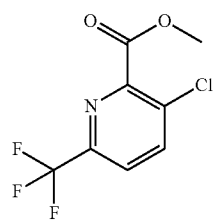

Intermediate 33 (2.2 g; 10 mmol) was dissolved in MeOH (8 ml) and DCM (22 ml). The solution was cooled to 0° C. then trimethylsilyl-diazomethane (2N, 8 ml, 16 mmol) was added and the mixture was stirred 10 minutes at 0° C. The solvent was evaporated. Crude was purified on silica gel (Cyclohexane/AcOEt=8/2). Yield 1.6 g.

NMR(CDCl3) δ ppm=8.02 (d, 1H), 7.77 (d, 1H), 4.05 (s, 3H).

Example 35

Preparation of Intermediate 35: methyl 3-(pyrimidin-2-yl)-6-(trifluoromethyl)picolinate

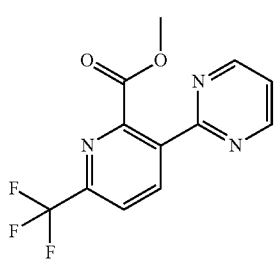 [SMILES: COC(=O)c1nc(C(F)(F)F)ccc1-c1ncccn1]

Intermediate 34 (1.6 g, 6.7 mmol) was dissolved dry DMF (10 ml), then CsF (2.05 g; 13.5 mmol), CuI (260 mg; 1.35 mmol), [Ph3P]4Pd (774 mg; 0.67 mmol) and pyrimidine-2-tributylstannane (3 g; 8 mmol; prepared according to Eur. J. Org. Chem. 2003, 1711-1721) were added. The mixture was warmed at 130° C. for 10 minutes (microwave), then poured in water and extracted with AcOEt (3×50 ml). The organic layers were combined, dried (Na2SO4) and concentrated under vacuum; crude product was purified by silica gel column chromatography (DCM to DCM/MeOH 95/5) to give 0.6 g of the title compound as white solid.

MS (ESI) m/z: 284 [M+H]+.

Example 36

Preparation of Intermediate 36: 3-(pyrimidin-2-yl)-6-(trifluoromethyl)picolinic acid

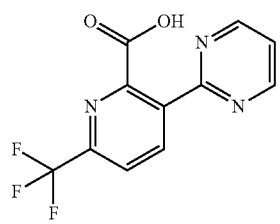 [SMILES: O=C(O)c1nc(C(F)(F)F)ccc1-c1ncccn1]

Intermediate 34 (600 mg; 2.12 mmol) was dissolved in THF (8 ml), MeOH (8 ml) and water (4 ml) and LiOH.H2O (223 mg; 5.3 mmol) was added. The mixture was stirred for 1 h at rt then was evaporated. The residue was dissolved in water (10 ml), washed twice with i-Pr20 (5 ml), acidified with HCl (4N, 4 ml) and extracted with AcOEt (5 ml) twice. The organics were dried, filtrated and evaporated. Yield 430 mg MS (ESI) m/z: 292 [M+Na]+.

NMR (DMSO-d6) δ ppm=13.64 (br.s, 1H), 8.99 (d, 2H), 8.77 (d, 1H), 8.19 (d, 1H), 7.61 (t, 1H).

Example 37

Preparation of Intermediate 37

(RS)(4,4-difluoro-2-(((5-(trifluoromethyl)pyridin-2-yl)amino)methyl)piperidin-1-yl)(3-iodo-6-methyl-pyridin-2-yl)methanone

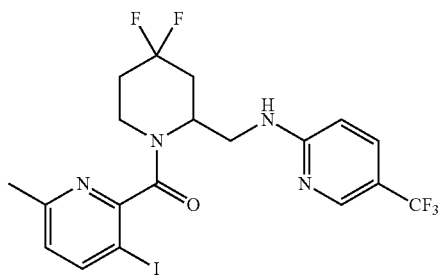 [SMILES: Cc1ccc(I)c(C(=O)N2CCC(F)(F)CC2CNc2ccc(C(F)(F)F)cn2)n1]

A suspension of 3 iodo-6-methyl picolinic acid (98.1 mg, 0.37 mmol; prepared according to WO2010063663), N-methyl morpholine (111 μl; 1.02 mmol) and 2-chloro-4,6-dimethoxy-1,3,5-triazine (89.2 mg; 0.51 mmol) dissolved in dry 1,4-dioxane (3 ml) and dry DMF (1 ml) was stirred at 25° C. for 0.5 hours, then intermediate 14 (100 mg; 0.34 mmol) dissolved in 1,4-dioxane (2 ml) was added. After 45 minutes at 80° C. solvents were evaporated and residue was dissolved in EtOAc, washed with HCl 0.1N, NaOH 1N and brine. The crude was purified by silica gel column chromatography (DCM to AcOEt); yield 150 mg, white solid.

MS (ESI) m/z: 541 [M+H]+.

Example 38

Preparation of Intermediate 38: (RS)(3-bromo-6-methylpyridin-2-yl)(4,4-difluoro-2-(((5-(trifluoromethyl)pyridine-2-yl)amino)methyl)piperidin-1-yl)methanone

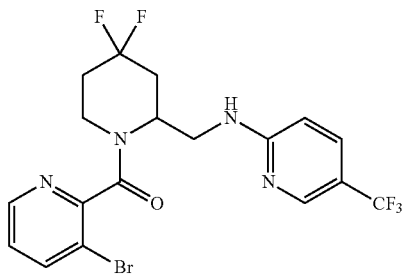 [SMILES: O=C(c1ncccc1Br)N1CCC(F)(F)CC1CNc1ccc(C(F)(F)F)cn1]

A suspension of 3 bromo picolinic acid (45 mg, 0.22 mmol), N-methyl morpholine (77 µl; 0.7 mmol) and 2-chloro-4,6-dimethoxy-1,3,5-triazine (61 mg; 0.35 mmol) dissolved in dry 1,4-dioxane (2 ml) was stirred at 25° C. for 0.5 hours, then intermediate 14 (60 mg; 0.2 mmol) dissolved in 1,4-dioxane (1 ml) was added. After 45 minutes at 80° C. solvents were evaporated and residue was dissolved in EtOAc, washed with sat. NH4Cl, NaOH 1N and brine. The crude was purified by silica gel column chromatography (DCM to AcOEt); yield 87.5 mg, white solid.

1HNMR (CD3COCD3) δ ppm 8.08-8.34 (m, 2H), 7.59-7.63 (m, 1H), 7.06-7.12 (m, 1H), 6.70-7.80 (m, 1H), 6.51-6.69 (m, 1H), 4.80-5.34 (m, 1H), 4.18-4.30 (m, 1H), 3.93-4.01 (m, 1H), 3.36-3.57 (m, 1H), 3.31-3.42 (m, 1H), 3.16-3.26 (m, 1H), 2.45 (s, 3H), 1.97-2.43 (m, 4H, under the solvent peak).

MS (ESI) m/z: 481[M+H]+.

Example 39

Preparation of Intermediate 39: (3-(benzyloxy)-6-methylpyridin-2-yl)methanol

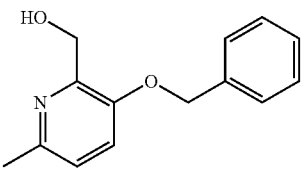 [SMILES: Cc1ccc(OCc2ccccc2)c(CO)n1]

2-(hydroxymethyl)-6-methylpyridin-3-ol (100 mg; 0.120 mmol); K2CO3 (497 mg; 3.59 mmol) and (bromomethyl)benzene (246 mg; 1.44 mmol) were stirred in DMF (1 ml) at RT for 18 h; solvent was evaporated, residue was dissolved in HCl 0.1N (20 ml) and washed with ethyl acetate (3×10 ml); aqueous phase was treated with Na2CO3 to pH 9 and extracted with acetate (3×10 ml). Organics were washed with brine, dried and evaporated to give 110 mg of the title compound (yellow solid).

MS (ESI) m/z: 230 [M+H]+.

1HNMR (CDCl3) δ ppm=7.34-7.41 (m, 5H), 7.12 (d, J=8 Hz, 1H), 7.02 (d, J=8 Hz, 1H), 5.12 (s, 2H), 4.80 (s, 2H), 4.51 (br. s. 1H), 2.53 (s, 3H).

Example 40

Preparation of Intermediate 40: 3-(benzyloxy)-6-methylpicolinic acid

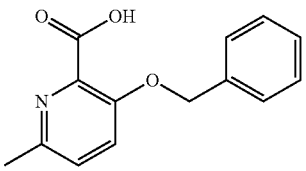 [SMILES: Cc1ccc(OCc2ccccc2)c(C(=O)O)n1]

To a solution of intermediate 39 (110 mg; 0.48 mmol) in acetonitrile (3 ml) TEMPO (11.3 mg; 0.072 mmol) and NaH2PO4 (0.64M in water; 2.06 ml) are added. The solution is warmed at 35° C. then NaOCl2 (235 mg in 1 ml of water; 2.6 mmol) and NaOCl (128 µl in 1 ml of water) are added simultaneously. After 2 h NaOH 2N is added to pH 8, then the mixture was poured in ice and an aqueous solution of Na2S2O3, stirred for 30 min, then extracted with DCM (3×20 ml); organics were washed with water, dried and evaporated. Yield 105 mg, light yellow solid.

MS (ESI) m/z: 244 [M+H]+.

1HNMR (CDCl3) δ ppm=7.51-7.53 (m, 2H), 7.39-7.42 (m, 3H), 7.33-7.36 (m, 2H), 5.32 (s, 2H), 2.56 (s, 3H).

Preparation of Compounds According to Certain Embodiments of the Invention

Examples 41-90

Preparation of Compounds 1-49

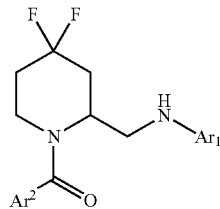

Carboxylic acids Ar2-COOH were commercially available or prepared according to U.S. Pat. No. 3,282,927 for compounds 1-2, WO2008147518 (compounds 3-7, 30), WO2010063663 (compounds 8, 9, 14-17, 20, 28, 29, 31, 32, 42), example 23 (compound 18), example 26 (compound 19), example 28 (compound 27), example 30 (compounds 36-38, 43-45).

Coupling general procedure 1

Ar2-COOH (1.1eq;), HOBT (1.1 eq) and EDCl.HCl (1.6eq) dissolved in dichloromethane (20 ml/mmol) were stirred at 25° C. for 0.5-2 hours, then intermediates 12-17

(1eq.) dissolved in dichloromethane were added. After 18 hours the mixture was poured in an aqueous saturated solution of NaHCO3 and extracted with dichloromethane. The crude was purified by silica gel column chromatography (DCM to DCM/MeOH=9/1)

Coupling General Procedure 2

Ar2-COOH (1.1eq) and HBTU (1.1 eq) dissolved in dichloromethane (20 ml/mmol) were stirred at 25° C. for 0.5-2 hours, then intermediates 12-17 (1eq.) and DIPEA (2 eq.) dissolved in dichloromethane were added. After 18 hours the mixture was poured in an aqueous saturated solution of NaHCO3 and extracted with dichloromethane. The crude was purified by silica gel column chromatography (DCM to DCM/MeOH=9/1)

Coupling General Procedure 3

Ar2-COOH (1.1eq), N-methyl morpholine (3 eq) and 2-chloro-4,6-dimethoxy-1,3,5-triazine (1.5eq) dissolved in dry 1,4-dioxane (20 ml/mmol) were stirred at 25° C. for 0.5 hours, then intermediates 12-17 (1eq.) dissolved in 1,4-dioxane were added. After 3 hours at 80° C. solvents were evaporated and residue was dissolved in EtOAc, washed with HCl 0.1N, NaOH 1N and brine. The crude was purified by silica gel column chromatography (DCM to DCM/MeOH=9/1)

Coupling General Procedure 4

Ar2-COOH (1.5eq), HBTU (1.4 eq). HOBT (1.5eq) dissolved in DMF (20 ml/mmol) were stirred at 25° C. for 0.5 hours, then intermediates 12-17 (1eq.) and DIPEA (3 eq.) dissolved in DMF (10 ml/mmol) were added. After 18 hours solvents were evaporated; residue poured in an aqueous saturated solution of NaHCO3 and extracted with dichloromethane. The crude was purified by silica gel column chromatography (DCM/AcOEt=9/1 to AcOEt 100%)

According to general procedure 1, 2, 3 or 4 the following compounds 1-49 were prepared:

| Compound | Name | Yield |
|---|---|---|
| 1 | (RS)(2-(((5-chloropyridin-2-yl)amino)methyl)-4,4-difluoropiperidin-1-yl)(2-methyl-5-phenylthiazol-4-yl)methanone | 90 |
| 2 | (2-(((5-chloropyridin-2-yl)amino)methyl)-4,4-difluoropiperidin-1-yl)(2-methyl-5-phenylthiazol-4-yl)methanone (isomer A) | 42* |
| 3 | (2-(((5-chloropyridin-2-yl)amino)methyl)-4,4-difluoropiperidin-1-yl)(5-methyl-2-(2H-1,2,3-triazol-2-yl)phenyl)methanone (isomer A) | 18* |
| 4 | (2-(((4,6-dimethylpyrimidin-2-yl)amino)methyl)-4,4-difluoropiperidin-1-yl)(5-methyl-2-(2H-1,2,3-triazol-2-yl)phenyl)methanone (isomer A) | 41 |
| 5 | (RS)(4,4-difluoro-2-(((5-(trifluoromethyl)pyridin-2-yl)amino)methyl)piperidin-1-yl)(5-methyl-2-(2H-1,2,3-triazol-2-yl)phenyl)methanone | 85 |
| 6 | (RS)(2-(((5-chloropyridin-2-yl)amino)methyl)-4,4-difluoropiperidin-1-yl)(5-methyl-2-(pyrimidin-2-yl)phenyl)methanone | 50 |
| 7 | (2-(((5-chloropyridin-2-yl)amino)methyl)-4,4-difluoropiperidin-1-yl)(5-methyl-2-(pyrimidin-2-yl)phenyl)methanone (isomer A) | 24* |
| 8 | (2-(((5-chloropyridin-2-yl)amino)methyl)-4,4-difluoropiperidin-1-yl)(6-methyl-3-(2H-1,2,3-triazol-2-yl)pyridin-2-yl)methanone (isomer A) | 35* |
| 9 | (2-(((5-chloropyridin-2-yl)amino)methyl)-4,4-difluoropiperidin-1-yl)(6-methyl-3-(2H-1,2,3-triazol-2-yl)pyridin-2-yl)methanone (isomer B) | 50* |
| 10 | (RS)(2-(((5-chloropyridin-2-yl)amino)methyl)-4,4-difluoropiperidin-1-yl)(2-ethoxyphenyl)methanone | 56 |
| 11 | (RS)(2-(((5-chloropyridin-2-yl)amino)methyl)-4,4-difluoropiperidin-1-yl)(2,5-dimethoxyphenyl)methanone | 66 |
| 12 | (RS)(2-(((5-chloropyridin-2-yl)amino)methyl)-4,4-difluoropiperidin-1-yl)(2-(cyclopropylmethoxy)phenyl)methanone | 60 |
| 13 | (RS)(2-(((5-chloropyridin-2-yl)amino)methyl)-4,4-difluoropiperidin-1-yl)(2-(cyclopentyloxy)phenyl)methanone | 70 |
| 14 | (RS)(2-(((5-chloropyridin-2-yl)amino)methyl)-4,4-difluoropiperidin-1-yl)(6-methyl-3-(pyrimidin-2-yl)pyridin-2-yl)methanone | 45 |
| 15 | (RS)(2-(((5-chloropyridin-2-yl)amino)methyl)-4,4-difluoropiperidin-1-yl)(5-methyl-2-(pyrimidin-2-yl)pyridin-3-yl)methanone | 7 |
| 16 | (2-(((5-chloropyridin-2-yl)amino)methyl)-4,4-difluoropiperidin-1-yl)(6-methyl-3-(pyrimidin-2-yl)pyridin-2-yl)methanone (isomer A) | 47* |
| 17 | (2-(((5-chloropyridin-2-yl)amino)methyl)-4,4-difluoropiperidin-1-yl)(6-methyl-3-(pyrimidin-2-yl)pyridin-2-yl)methanone (isomer B) | 49* |
| 18 | (RS)(2-(((5-chloropyridin-2-yl)amino)methyl)-4,4-difluoropiperidin-1-yl)(4-(dimethylamino)-[1,1'-biphenyl]-2-yl)methanone | 14 |
| 19 | (RS)(5-chloro-2-(pyrimidin-2-yl)phenyl)(2-(((5-chloropyridin-2-yl)amino)methyl)-4,4-difluoropiperidin-1-yl)methanone | 80 |
| 20 | (4,4-difluoro-2-(((5-(trifluoromethyl)pyridin-2-yl)amino)methyl)piperidin-1-yl)(6-methyl-3-(pyrimidin-2-yl)pyridin-2-yl)methanone (isomer A) | 42* |
| 21 | (RS)(2-(benzyloxy)phenyl)(2-(((5-chloropyridin-2-yl)amino)methyl)-4,4-difluoropiperidin-1-yl)methanone | 70 |
| 22 | (RS)(2-(((5-chloropyridin-2-yl)amino)methyl)-4,4-difluoropiperidin-1-yl)(isoquinolin-1-yl)methanone | 80 |
| 23 | (2-(((5-chloropyridin-2-yl)amino)methyl)-4,4-difluoropiperidin-1-yl)(isoquinolin-1-yl)methanone (isomer A) | 30* |
| 24 | (2-(((5-chloropyridin-2-yl)amino)methyl)-4,4-difluoropiperidin-1-yl)(isoquinolin-1-yl)methanone (isomer B) | 30* |
| 25 | (RS)(2-(((5-chloropyridin-2-yl)amino)methyl)-4,4-difluoropiperidin-1-yl)(quinolin-8-yl)methanone | 76 |
| 26 | (2-(((5-chloropyridin-2-yl)amino)methyl)-4,4-difluoropiperidin-1-yl)(quinolin-8-yl)methanone (isomer A) | 30* |
| 27 | (RS)3-(2-(((5-chloropyridin-2-yl)amino)methyl)-4,4-difluoropiperidin-1-carbonyl)-4-(pyrimidin-2-yl)benzonitrile | 10 |

-continued

| Compound | Name | Yield |
|---|---|---|
| 28 | (RS)(2-(((5-chloropyridin-2-yl)amino)methyl)-4,4-difluoropiperidin-1-yl)(3-(pyrimidin-2-yl)pyridin-4-yl)methanone | 14 |
| 29 | (RS)6-(((4,4-difluoro-1-(6-methyl-3-(pyrimidin-2-yl)picolinoyl)piperidin-2-yl)methyl)amino)nicotionitrile | 40 |
| 30 | (RS)(4,4-difluoro-2-(((5-(trifluoromethyl)pyridin-2-yl)amino)methyl)piperidin-1-yl)(5-fluoro-2-(2-methylpyrimidin-5-yl)phenyl)methanone | 7 |
| 31 | (RS)(4,4-difluoro-2-(((3-fluoro-5-(trifluoromethyl)pyridin-2-yl)amino)methyl)piperidin-1-yl)(6-methyl-3-(pyrimidin-2-yl)pyridin-2-yl)methanone | 95 |
| 32 | (4,4-difluoro-2-(((3-fluoro-5-(trifluoromethyl)pyridin-2-yl)amino)methyl)piperidin-1-yl)(6-methyl-3-(pyrimidin-2-yl)pyridin-2-yl)methanone (isomer A) | 40 |
| 33 | (RS)(4,4-difluoro-2-(((3-fluoro-5-(trifluoromethyl)pyridin-2-yl)amino)methyl)piperidin-1-yl)(isoquinolin-1-yl)methanone | 92 |
| 34 | (RS)(4,4-difluoro-2-(((5-(trifluoromethyl)pyridin-2-yl)amino)methyl)piperidin-1-yl)(isoquinolin-1-yl)methanone | 95 |
| 35 | (RS)(4,4-difluoro-2-(((5-(trifluoromethyl)pyridin-2-yl)amino)methyl)piperidin-1-yl)quinolin-4-yl)methanone | 80 |
| 36 | (RS)(4,4-difluoro-2-(((5-(trifluoromethyl)pyridin-2-yl)amino)methyl)piperidin-1-yl)(6-methyl-3-phenylpyridin-2-yl)methanone | 78 |
| 37 | (4,4-difluoro-2-(((5-(trifluoromethyl)pyridin-2-yl)amino)methyl)piperidin-1-yl)(6-methyl-3-phenylpyridin-2-yl)methanone (isomer A) | 35 |
| 38 | (4,4-difluoro-2-(((5-(trifluoromethyl)pyridin-2-yl)amino)methyl)piperidin-1-yl)(6-methyl-3-phenylpyridin-2-yl)methanone (isomer B) | 32 |
| 39 | (RS)(4,4-difluoro-2-(((5-(trifluoromethyl)pyridin-2-yl)amino)methyl)piperidin-1-yl)(3-(pyrimidin-2-yl)-6-(trifluoromethyl)pyridin-2-yl)methanone | 63 |
| 40 | (4,4-difluoro-2-(((5-(trifluoromethyl)pyridin-2-yl)amino)methyl)piperidin-1-yl)(3-(pyrimidin-2-yl)-6-(trifluoromethyl)pyridin-2-yl)methanone (isomer A) | 37 |
| 41 | (4,4-difluoro-2-(((5-(trifluoromethyl)pyridin-2-yl)amino)methyl)piperidin-1-yl)(isoquinolin-1-yl)methanone (isomer A) | 40 |
| 42 | (RS)(4,4-difluoro-2-(((5-(trifluoromethyl)pyridin-2-yl)amino)methyl)piperidin-1-yl)(6-methyl-3-(pyrimidin-2-yl)pyridin-2-yl)methanone | 70 |
| 43 | (RS)(4,4-difluoro-2-(((5-(trifluoromethyl)pyridin-2-yl)amino)methyl)piperidin-1-yl)(6-methyl-3-(pyrimidin-2-yl)pyridin-2-yl)methanone | 52 |
| 44 | (RS)(4,4-difluoro-2-(((3-fluoro-5-(trifluoromethyl)pyridin-2-yl)amino)methyl)piperidin-1-yl)(6-methyl-3-phenylpyridin-2-yl)methanone | 51 |
| 45 | (RS)(3-(cyclopropylmethoxy)-6-methylpyridin-2-yl)(4,4-difluoro-2-(((5-(trifluoromethyl)pyridin-2-yl)amino)methyl)piperidin-1-yl)methanone | 76 |
| 46 | (S)(3-(cyclopropylmethoxy)-6-methylpyridin-2-yl)(4,4-difluoro-2-(((5-(trifluoromethyl)pyridin-2-yl)amino)methyl)piperidin-1-yl)methanone | 30 |
| 47 | (RS)(3-(benzyloxy)-6-methylpyridin-2-yl)(4,4-difluoro-2-(((5-(trifluoromethyl)pyridin-2-yl)amino)methyl)piperidin-1-yl)methanone | 36 |
| 48 | (RS)(4,4-difluoro-2-(((5-(trifluoromethyl)pyridin-2-yl)amino)methyl)piperidin-1-yl)(6-methyl-3-(pyrimidin-2-yl)pyridin-2-yl)methanone | 71 |
| 49 | (RS)(4,4-difluoro-2-(((5-(trifluoromethyl)pyridin-2-yl)amino)methyl)piperidin-1-yl)(6-methyl-3-(pyrimidin-2-yl)pyridin-2-yl)methanone | 53 |

*= Yield after separation of enantiomers on chiral preparative HPLC.

Compounds 1-45 Characterization:

| Comp. | P | R | Proc. | $^1$H-NMR | MS | ee % |
|---|---|---|---|---|---|---|
| 1 | 5-chloropyridin-2-yl | 2-methyl-5-phenylthiazol-4-yl | 1 | $^1$HNMR (CDCl$_3$) δ ppm 7.86-8.03 (m, 1H), 7.30-744 (m, 6H), 6.26-6.48 (m, 1H), 5.32 (m, 1H), 4.88-5.02 (m, 1H), 3.85-4.34 (m, 1H), 2.95-3.55 (m, 3H), 2.74-2.99 (m, 3H), 1.60-2.15 (m, 4H) | ESI m/z 463 [M + H]$^+$. | racemate |

| Comp. | P | R | Proc. | ¹H-NMR | MS | ee % |
|---|---|---|---|---|---|---|
| 2 | 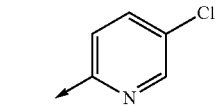 | 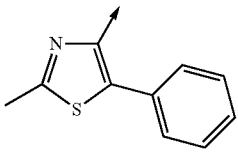 | 1 | — | ESI m/z 463 [M + H]⁺. | 96* Method A RT 27 min |
| 3 | 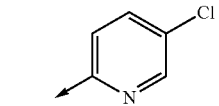 | 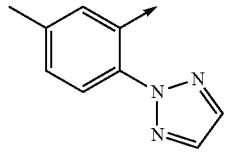 | 2 | ¹HNMR (CDCl₃) δ ppm 7.97-8.05 (m, 1H), 7.70-7.90 (m, 3H), 7.25-7.47 (m, 2H), 7.0-7.25 (m, 1H), 6.20-6.48 (m, 1H), 5.31-5.54 (m, 1H), 4.66-4.90 (m, 1H), 4.20-4.42 (m, 1H), 3.05-3.69 (m, 4H), 2.16-2.45 (m, 3H), 1.75-2.15 (m, 2H), 1.22-1.55 (m, 1H) | ESI m/z 447 [M + H]⁺. | 98* Method B RT 20 min |
| 4 | 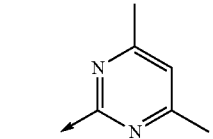 | 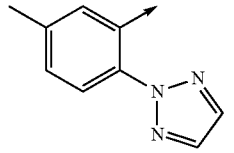 | 3 | ¹HNMR (CDCl₃) δ ppm 7.75-8.0 (m, 3H), 7.07-7.45 (m, 2H), 6.31-6.39 (m, 1H), 4.87-5.41 (m, 1H), 4.19-4.25 (m, 1H), 3.82-3.89 (m, 1H), 3.20-3.31 (m, 3H), 1.70-2.45 (m, 3H) | ESI m/z 442 [M + H]⁺. | racemate |
| 5 | 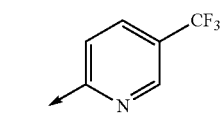 | 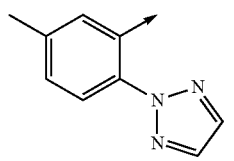 | 2 | ¹HNMR (CDCl₃) δ ppm 7.98-8.40 (m, 1H), 7.70-7.90 (m, 4H), 7.54-7.64 (m, 1H), 7.01-7.54 (m, 1H), 6.29-6.55 (m, 1H), 5.36-5.92 (m, 1H), 4.90-5.17 (m, 1H), 4.24-4.55 (m, 1H), 3.40-3.79 (m, 2H), 3.07-3.27 (m, 1H), 1.82-2.46 (m, 6H) | ESI m/z 481 [M + H]⁺. | racemate |
| 6 | 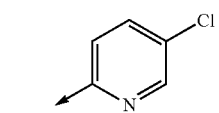 | 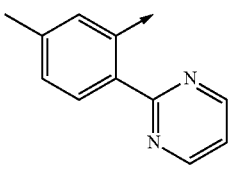 | 3 | ¹HNMR (CDCl₃) δ ppm 8.62-8.75 (m, 1H), 7.81-8.39 (m, 2H), 7.05-7.30 (m, 4H), 6.19-6.48 (m, 2H), 5.20-5.60 (m, 1H), 4.25-5.02 (m, 2H), 3.09-3.87 (m, 4H), 2.15-2.46 (m, 4H), 1.75-2.01 (m, 2H) | ESI m/z 458 [M + H]⁺. | racemate |
| 7 | 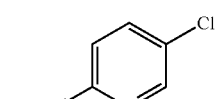 | 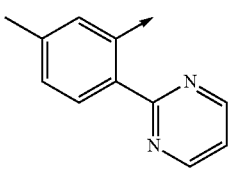 | 3 | ¹HNMR (CDCl₃) δ ppm 8.62-8.75 (m, 1H), 7.81-8.39 (m, 2H), 7.05-7.20 (m, 4H), 6.17-6.49 (m, 2H), 5.30-5.63 (m, 1H), 4.30-5.05 (m, 2H), 3.12-3.65 (m, 4H), 2.10-2.46 (m, 4H), 1.80-1.98 (m, 2H) | ESI m/z 458 [M + H]⁺. | 98* Method C RT 11.5 min |
| 8 | 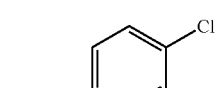 | 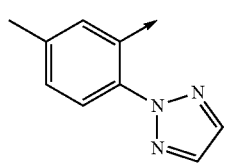 | 3 | ¹HNMR (CDCl₃) δ ppm 8.23-8.29 (m, 1H), 7.94-8.08 (m, 1H), 7.83-7.87 (m, 2H), 7.30-7.38 (m, 2H), 6.14-6.42 (m, 2H), 4.82-5.35 (m, 1H), 3.85-4.36 (m, 2H), 3.12-3.65 (m, 2H), 2.64-2.66 (m, 3H), 2.05-2.35 (m, 4H) | ESI m/z 448 [M + H]⁺ | 98* Method D RT 15.8 min |
| 9 | 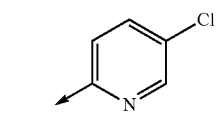 | 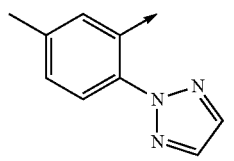 | 3 | — | ESI m/z 448 [M + H]⁺ | 98* Method D RT 20.6 min |
| 10 | 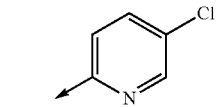 | 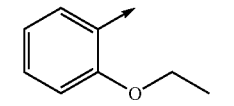 | 2 | ¹HNMR (CDCl₃) δ ppm 7.68-8.04 (m, 1H), 7.20-7.45 (m, 2H), 6.65-7.10 (m, 3H), 6.10-6.55 (m, 1H), 5.10-5.40 (m, 1H), 4.60-4.95 (m, 1H), 3.95-4.30 (m, 2H), 3.05-3.65 (m, 3H), 2.0-2.45 (m, 4H), 1.25-1.45 (m, 4H) | ESI m/z 410 [M + H]⁺. | racemate |

-continued

| Comp. | P | R | Proc. | ¹H-NMR | MS | ee % |
|---|---|---|---|---|---|---|
| 11 | 5-chloropyridin-2-yl | 2,5-dimethoxyphenyl | 2 | ¹HNMR (CDCl₃) δ ppm 7.20-8.05 (m, 2H), 7.0-7.70 (m, 2H), 6.15-6.54 (m, 2H), 5.25-5.35 (m, 1H), 4.65-4.95 (m, 1H), 3.90-4.29 (m, 1H), 3.65-3.82 (m, 6H), 3.20-3.60 (m, 2H), 1.80-2.30 (m, 5H) | ESI m/z 426 [M + H]⁺. | racemate |
| 12 | 5-chloropyridin-2-yl | 2-(cyclopropylmethoxy)phenyl | 2 | ¹HNMR (CDCl₃) δ ppm 7.68-8.01 (m, 1H), 7.20-7.50 (m, 3H), 6.55-7.05 (m, 3H), 4.95-5.38 (m, 1H), 4.11-4.17 (m, 1H), 3.78-3.94 (m, 2H), 3.37-3.55 (m, 3H), 2.0-2.44 (m, 5H), 1.19-1.25 (m, 1H), 0.63 (m, 2H), 0.33 (m, 2H) | ESI m/z 436 [M + H]⁺. | racemate |
| 13 | 5-chloropyridin-2-yl | 2-(cyclopentyloxy)phenyl | 2 | ¹HNMR (CDCl₃) δ ppm 7.69-8.04 (m, 1H), 7.20-7.45 (m, 2H), 6.65-7.04 (m, 3H), 6.11-6.53 (m, 1H), 5.30-5.37 (m, 1H), 4.80-4.95 (m, 2H), 3.05-3.64 (m, 4H), 1.62-2.40 (m, 12H) | ESI m/z 450 [M + H]⁺. | racemate |
| 14 | 5-chloropyridin-2-yl | 6-methyl-3-(pyrimidin-2-yl)pyridin-2-yl | 3 | — | ESI m/z 459 [M + H]⁺. | |
| 15 | 5-chloropyridin-2-yl | 5-methyl-3-(pyrimidin-2-yl)pyridin-2-yl | 3 | ¹HNMR (CDCl₃) δ ppm 8.61-8.87 (m, 3H), 7.78-8.05 (m, 1H), 7.25-7.53 (m, 2H), 6.85-7.20 (m, 1H), 6.27-6.55 (m, 1H), 5.22-5.40 (m, 1H), 4.73-4.92 (m, 1H), 4.31-4.37 (m, 1H), 3.10-3.85 (m, 4H), 1.68-2.50 (m, 5H) | ESI m/z 459 [M + H]⁺. | racemate |
| 16 | 5-chloropyridin-2-yl | 6-methyl-3-(pyrimidin-2-yl)pyridin-2-yl | 3 | ¹HNMR (CDCl₃) δ ppm 8.74-8.81 (m, 2H), 8.50-8.62 (m, 1H), 8.01-8.08 (m, 1H), 7.29-7.37 (m, 3H), 6.40-6.55 (m, 1H), 4.85-5.45 (m, 1H), 4.37-4.82 (m, 1H), 3.65-4.02 (m, 1H), 3.10-3.66 (m, 2H), 2.65-2.69 (m, 3H), 2.49-2.60 (m, 1H), 2.04-2.40 (m, 4H) | ESI m/z 459 [M + H]⁺ | 96* Method C RT 13.6 min |
| 17 | 5-chloropyridin-2-yl | 6-methyl-3-(pyrimidin-2-yl)pyridin-2-yl | 3 | — | ESI m/z 459 [M + H]⁺ | 98* Method C RT 15.7 min |
| 18 | 5-chloropyridin-2-yl | 4-(dimethylamino)-2-phenyl-phenyl | 3 | ¹HNMR (CDCl₃) δ ppm 7.75-8.0 (m, 1H), 7.17-7.47 (m, 8H), 6.49-6.80 (m, 1H), 5.47-6.28 (m, 1H), 4.97-5.21 (m, 1H), 4.46-4.86 (m, 1H), 4.07-4.16 (m, 1H), 3.40 (m, 1H), 3.04-3.20 (m, 3H), 2.95 (s, 6H), 1.91-2.07 (m, 1H), 1.28-1.60 (m, 2H) | ESI m/z 485 [M + H]⁺ | racemate |
| 19 | 5-chloropyridin-2-yl | 4-chloro-2-(pyrimidin-2-yl)phenyl | 3 | ¹HNMR (CDCl₃) δ ppm 8.64-8.75 (m, 1H), 8.21-8.45 (m, 1H), 7.85-8.09 (m, 1H), 7.14-7.54 (m, 5H), 6.28-6.54 (m, 1H), 5.26-5.55 (m, 1H), 4.57-4.92 (m, 1H), 4.31-4.40 (m, 1H), 3.60-3.85 (m, 1H), 3.39-3.53 (m, 2H), 3.15-3.28 (m, 1H), 1.87-2.43 (m, 3H) | ESI m/z 478 [M + H]⁺ | racemate |

| Comp. | P | R | Proc. | ¹H-NMR | MS | ee % |
|---|---|---|---|---|---|---|
| 20 | 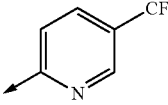 | 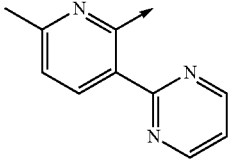 | 3 | ¹HNMR (CDCl₃) δ ppm 8.72-8.81 (m, 2H), 8.53-8.63 (m, 1H), 8.33-8.40 (m, 1H), 7.30-7.56 (m, 3H), 7.05-7.17 (m, 1H), 6.44-6.52 (m, 1H), 5.40-5.85 (m, 1H), 4.41-4.87 (m, 1H), 3.90-4.15 (m, 1H), 3.10-3.74 (m, 2H), 2.51-2.70 (m, 4H), 2.05-2.40 (m, 3H) | ESI m/z 493 [M + H]⁺ | 98* Method E RT 14.9 min |
| 21 | 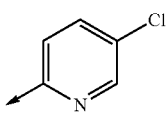 | 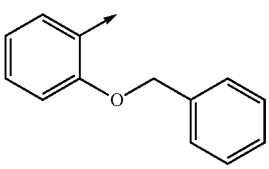 | 4 | ¹HNMR (CDCl₃) δ ppm 7.98-8.22 (m, 1H), 7.50-7.67 (m, 1H), 7.15-7.45 (m, 6H), 6.69-7.10 (m, 3H), 6.05-6.52 (m, 1H), 5.20-5.25 (m, 1H), 4.70-5.08 (m, 1H), 4.05-4.25 (m, 1H), 3.25-3.65 (m, 3H), 1.75-2.30 (m, 4H) | ESI m/z 472 [M + H]⁺ | racemate |
| 22 | 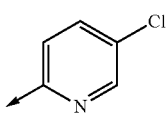 | 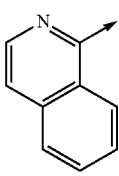 | 4 | ¹HNMR (CDCl3)) δ ppm 8.44-8.52 (m, 1H), 7.49-8.07 (m, 6H), 6.74-7.17 (m, 1H), 6.21-6.57 (m, 1H), 5.04-5.45 (m, 1H), 4.13-4.41 (m, 1H), 3.56-3.89 (m, 1H), 3.33-3.55 (m, 1H), 3.17-3.32 (m, 1H), 2.27-2.44 (m, 1H), 2.09-2.24 (m, 2H), 1.96-2.08 (m, 1H) | ESI m/z 417 [M + H]⁺ | racemate |
| 23 | 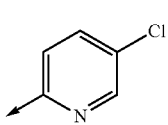 | 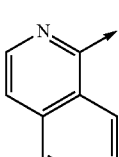 | 4 | — | ESI m/z 417 [M + H]⁺ | 98* Method F RT 19.2 min |
| 24 | 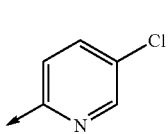 | 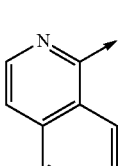 | 4 | ¹HNMR (DMSO) δ ppm 8.32-8.50 (m, 1H), 7.70-8.04 (m, 4H), 7.45-7.60 (m, 2H), 7.10-7.19 (m, 1H), 6.80-6.90 (m, 1H), 5.93-6.68 (m, 1H), 4.81-5.33 (m, 1H), 4.01-4.43 (m, 1H), 3.25-3.50 (m, 2H), 3.10-3.20 (m, 1H), 1.95-2.34 (m, 4H). | ESI m/z 417 [M + H]⁺ | 98* Method F RT 22.3 min |
| 25 | 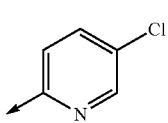 | 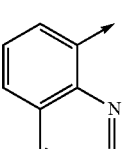 | 4 | ¹HNMR (MeOD) δ ppm 8.91 (m, 1H), 8.25-8.45 (m, 1H) 7.90-8.10 (m, 1H), 7.80-7.83 (m, 1H), 7.45-7.75 (m, 2H), 7.26-7.40 (m, 2H), 7.05-7.15 (m, 1H), 6.44-6.60 (m, 1H), 5.01 (m, 1H), 3.90-4.18 (m, 1H), 3.50-3.70 (m, 1H), 3.20-3.40 (m, 1H), 3.02-3.08 (m, 1H), 2.20-2.45 (m, 3H), 1.85-2.05 (m, 1H) | ESI m/z 417 [M + H]⁺ | racemate |
| 26 | 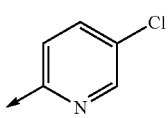 | 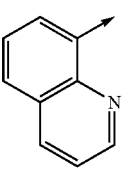 | 4 | ¹HNMR (MeOD) δ ppm 8.79-9.03 (m, 1H), 8.26-8.47 (m, 1H), 7.92-8.10 (m, 1H), 7.80-7.84 (m, 1H), 7.45-7.74 (m, 2H), 7.26-7.38 (m, 2H), 7.07-7.13 (m, 1H), 6.44-6.62 (m, 1H), 5.0-5.56 (m, 1H), 3.91-3.97 (m, 1H), 3.50-3.72 (m, 1H), 3.20-3.42 (m, 1H), 3.02-3.07 (m, 1H), 2.22-2.43 (m, 3H), 1.89-2.0 (m, 1H). | ESI m/z 417 [M + H]⁺ | 98* Method D RT 12.2 min |
| 27 | 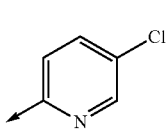 | 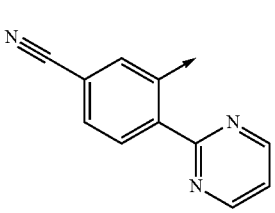 | 3 | ¹HNMR (CDCl₃) δ ppm 8.80-8.90 (m, 2H), 8.48-8.70 (m, 1H), 7.75-7.95 (m, 3H), 7.40-7.66 (m, 2H), 7.05-7.36 (m, 1H), 5.36 (m, 1H), 4.91 (m, 1H), 3.35-3.95 (m, 4H), 1.80-2.58 (m, 3H) | ESI m/z 470 [M + H]⁺ | racemate |

| Comp. | P | R | Proc. | ¹H-NMR | MS | ee % |
|---|---|---|---|---|---|---|
| 28 | 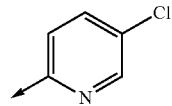 | 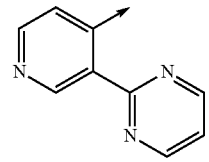 | 3 | ¹HNMR (CDCl₃) δ ppm 9.53-9.72 (m, 1H), 8.60-8.80 (m, 3H), 8.05-8.44 (m, 1H), 8.08-7.77 (m, 4H), 6.28-6.61 (m, 1H), 5.25-5.66 (m, 1H), 4.74-5.10 (m, 1H), 3.80-4.35 (m, 1H), 3.10-3.75 (m, 2H), 1.85-2.50 (m, 3H), 1.25-1.67 (m, 1H). | ESI m/z 445 [M + H]⁺ | racemate |
| 29 | 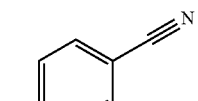 | 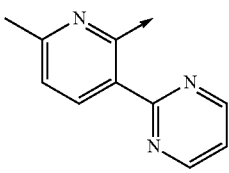 | 3 | ¹HNMR (CDCl₃) δ ppm 8.71-8.81 (m, 2H), 8.55-8.57 (m, 1H), 8.38-8.42 (m, 1H), 8.53-8.56 (m, 1H), 7.38-7.45 (m, 2H), 7.29-7.32 (m, 1H), 6 50-6.53 (m, 1H), 4.83-4.87 (m, 1H), 4.40-4.43 (m, 1H), 3.85-4.07 (m, 1H), 2.94-3.32 (m, 1H), 2.55-2.70 (m, 4H), 2.04-2.28 (m, 4H) | ESI m/z 450 [M + H]⁺ | racemate |
| 30 | 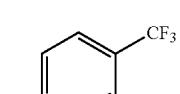 | 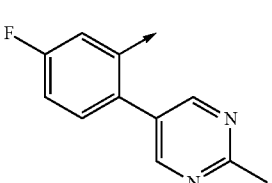 | 3 | ¹HNMR (MeOD) δ ppm 8.70-8.80 (m, 2H), 7.59-8.26 (m, 1H), 7.40-7.51 (m, 3H), 6.80-7.11 (m, 1H), 6.51-6.64 (m, 1H), 4.56-4.79 (m, 1H), 3.92-4.02 (m, 1H), 3.12-3.50 (m, 2H), 2.75 (s, 3H), 1.82-2.40 (m, 2H), 1.14-1.45 (m, 3H), 0.88-0.94 (m, 1H). | ESI m/z 510 [M + H]⁺ | racemate |
| 31 | 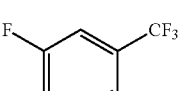 | 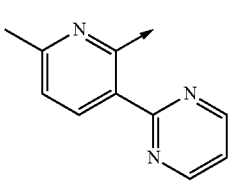 | 3 | ¹HNMR (CD₃COCD₃) δ ppm 8.83-8.90 (m, 2H), 8.49-8.53 (m, 1H), 8.11-8.25 (m, 1H), 7.54-7.57 (m, 1H), 7.40-7.50 (m, 2H), 7.32-7.38 (m, 1H), 4.73-5.38 (m, 1H), 4.20-4.65 (m, 1H), 3.42-3.67 (m, 1H), 3.12-3.20 (m, 1H), 2.48-2.59 (m, 4H), 2.10-2.30 (m, 3H) | ESI m/z 511 [M + H]⁺ | racemate |
| 32 | 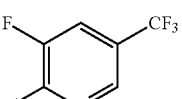 | 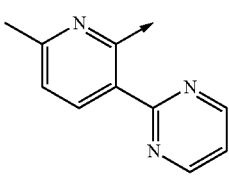 | 3 | — | ESI m/z 511 [M + H]⁺ | 96* Method E RT 13.3 min |
| 33 | 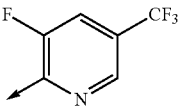 | 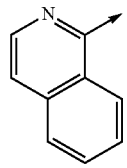 | 4 | ¹HNMR (CD₃COCD₃) δ ppm 8.34-8.47 (m, 1H), 7.99-8.02 (d, 1H), 7.77-7.85 (m, 1H), 7.67-7.74 (m, 2H), 7.50-7.60 (m, 2H), 7.07-7.10 (m, 1H), 4.97-5.63 (m, 1H), 4.39-4.75 (m, 1H), 3.71-3.98 (m, 1H), 3.31-3.42 (m, 2H), 2.13-2.46 (m, 4H) | ESI m/z 469 [M + H]⁺ | racemate |
| 34 | 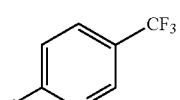 | 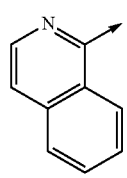 | 4 | ¹HNMR (CD₃COCD₃) δ ppm 8.37-8.49 (m, 1H), 7.98-8.05 (m, 1H), 7.83-7.85 (m, 1H), 7.67-7.78 (m, 2H), 7.46-7.61 (m, 1H), 7.84-7.20 (m, 1H), 6.75-7.15 (m, 1H), 5.53-6.17 (m, 1H), 4.97-5.01 (m, 1H), 4.35-4.63 (m, 1H), 3.77-3.85 (m, 1H), 3.56-3.68 (m, 1H), 3.26-3.39 (m, 2H), 2.10-2.43 (m, 3H). | ESI m/z 451 [M + H]⁺ | racemate |
| 35 | 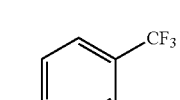 | 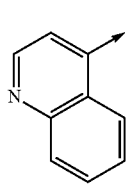 | 4 | ¹HNMR (CD₃COCD₃) δ ppm 8.78-8.94 (m, 1H), 8.30-8.55 (m, 1H), 8.05-8.09 (m, 1H), 7.93-7.98 (m, 1H), 7.68-7.82 (m, 2H), 7.48-7.55 (m, 1H), 7.14-7.30 (m, 1H), 6.83-6.89 (m ,1H), 6.52-6.77 (m, 1H), 5.55-6.10 (m, 1H), 4.93-5.04 (m, 1H), 4.37-4.59 (m, 1H), 3.63-3.98 (m, 1H), 3.47-3.54 (m, 1H), 3.31-3.38 (m, 1H), 2.14-2.54 (m, 3H) | ESI m/z 451 [M + H]⁺ | racemate |

-continued

| Comp. | P | R | Proc. | ¹H-NMR | MS | ee % |
|---|---|---|---|---|---|---|
| 36 | 5-CF₃-pyridin-2-yl | 6-methyl-3-phenyl-pyridin-2-yl | 3 | ¹HNMR (CD₃COCD₃) δ ppm 8.07-8.32 (m, 1H), 7.72-7.81 (m, 1H), 7.59-7.67 (m, 1H), 7.23-7.56 (m, 5H), 6.62-6.73 (m, 1H), 6.35-6.60 (m, 1H), 4.71-5.24 (m, 1H), 3.81-4.13 (m, 1H), 3.48-3.75 (m, 1H), 3.25-3.40 (m, 1H), 2.96-3.24 (m, 1H), 2.42-2.54 (m, 3H), 2.03-2.29 (m, 1H), 1.75-1.90 (m, 1H), 1.38-1.57 (m, 1H), 0.71-0.90 (m, 1H) | ESI m/z 491 [M + H]⁺ | racemate |
| 37 | 5-CF₃-pyridin-2-yl | 6-methyl-3-phenyl-pyridin-2-yl | 3 | — | ESI m/z 491 [M + H]⁺ | 96* Method I RT 17.0 min |
| 38 | 5-CF₃-pyridin-2-yl | 6-methyl-3-phenyl-pyridin-2-yl | 3 | — | ESI m/z 491 [M + H]⁺ | 96* Method I RT 19.8 min |
| 39 | 5-CF₃-pyridin-2-yl | 6-CF₃-3-(pyrimidin-2-yl)-pyridin-2-yl | 3 | ¹HNMR (CD₃COCD₃) δ ppm 8.98-9.01 (m, 2H), 8.90-8.95 (m, 1H), 8.11-8.37 (m, 1H), 8.06-8.10 (m, 1H), 7.59-7.67 (m, 1H), 7.53-7.57 (m, 1H), 6.51-6.72 (m, 1H), 4.57-5.31 (m, 1H), 4.02-4.16 (m, 1H), 3.62-3.80 (m, 1H), 3.42-3.50 (m, 1H), 3.18-3.27 (m, 1H), 2.10-2.51 (m, 4H) | ESI m/z 548 [M + H]⁺ | racemate |
| 40 | 5-CF₃-pyridin-2-yl | 6-CF₃-3-(pyrimidin-2-yl)-pyridin-2-yl | 3 | — | ESI m/z 548 [M + H]⁺ | 98* Method H RT 13.8 min |
| 41 | 5-CF₃-pyridin-2-yl | isoquinolin-1-yl | 4 | — | ESI m/z 451 [M + H]⁺ | 98* Method L RT 18.2 min |
| 42 | 5-CF₃-pyrazin-2-yl | 6-methyl-3-(pyrimidin-2-yl)-pyridin-2-yl | 3 | ¹HNMR (CD₃COCD₃) δ ppm 8.98-9.01 (m, 2H), 8.90-8.95 (m, 1H), 8.11-8.37 (m, 1H), 8.06-8.10 (m, 1H), 7.59-7.67 (m, 1H), 7.53-7.57 (m, 1H), 6.51-6.72 (m, 1H), 4.57-5.31 (m, 1H), 4.02-4.16 (m, 1H), 3.62-3.80 (m, 1H), 3.42-3.50 (m, 1H), 3.18-3.27 (m, 1H), 2.10-2.51 (m, 4H) | ESI m/z 494 [M + H]⁺ | racemate |
| 43 | 5-CF₃-pyrazin-2-yl | 6-methyl-3-phenyl-pyridin-2-yl | 3 | ¹HNMR (CD₃COCD₃) δ ppm 8.08-8.33 (m, 1H), 7.98 (s, 1H), 7.69-7.79 (m, 1H), 7.38-7.56 (m, 5H), 6.90-7.25 (m, 2H), 4.73-5.28 (m, 1H), 3.47-3.78 (m, 1H), 2.99-3.4 (m, 2H), 2.36-2.50 (m, 3H), 1.98-2.29 (m, 1H, under the solvent peak), 1.70-1.87 (m, 1H), 1.81-1.56 (m, 1H). | ESI m/z 492 [M + H]⁺ | racemate |

-continued

| Comp. | P | R | Proc. | ¹H-NMR | MS | ee % |
|---|---|---|---|---|---|---|
| 44 | F, CF₃ pyridine | methylpyridine-phenyl | 3 | ¹HNMR (CD₃COCD₃) δ ppm 7.93-8.18 (m, 1H), 7.68-7.79 (m, 1H), 7.37-7.57 (m, 6H), 7.16-7.18 (d, 1H), 6.52-6.94 (m, 1H), 4.72-5.32 (m, 1H), 4.10-4.17 (m, 1H), 3.55-3.91 (m, 1H), 3.02-3.61 (m, 2H), 2.36-2.50 (m, 3H), 1.99-2.23 (m, 1H, under the solvent peak), 1.71-1.84 (m, 1H), 1.40-1.58 (m, 1H). | ESI m/z 509 [M + H]⁺ | racemate |
| 45 | CF₃ pyridine | methylpyridine-OCH₂cyclopropyl | 3 | ¹HNMR (CD₃COCD₃) δ ppm 8.03-8.34 (m, 1H), 7.57-7.66 (m, 1H), 7.27-7.40 (m, 1H), 7.07-7.23 (m, 1H), 6.75-6.43 (m, 2H), 4.80-5.38 (m, 1H), 4.29-4.33 (m, 1H), 3.67-3.98 (m, 2H), 3.08-3.55 (m, 2H), 2.08-2.44 (m, 6H, under the solvent peak), 1.89-2.04 (m, 1H), 1.18-1.27 (m, 1H), 0.56-0.61 (m, 2H), 0.32-0.37 (m, 2H). | ESI m/z 485 [M + H]⁺ | racemate |
| 46 | CF₃ pyridine | methylpyridine-OCH₂cyclopropyl | 3 | — | ESI m/z 485 [M + H]⁺ | 98* Method M RT 18.9 min |
| 47 | CF₃ pyridine | methylpyridine-OBn | 3 | ¹HNMR (CD₃COCD₃) δ ppm 8.03-8.32 (m, 1H), 7.31-7.88 (m, 7H), 7.10-7.24 (m, 1H), 6.28-6.79 (m, 2H), 5.14-5.36 (m, 2H), 4.79-5.12 (m, 1H), 4.36 (m, 1H), 3.74-3.95 (m, 1H), 3.45-3.70 (m, 1H), 3.35-3.41 (m, 1H), 3.05-3.13 (m, 1H), 2.33-2.41 (m, 3H), 1.74-2.23 (m, 4H, under the sovent peak). | ESI m/z 521 [M + H]⁺ | racemate |

*= Eantiomeric eccess (ee) after separation of enantiomers on chiral preparative HPLC.

Example 91

Preparation of Compound 48: (±)(4,4-difluoro-2-(((5-(trifluoromethyl)pyridine-2-yl)oxy)methyl)piperidin-1-yl)(6-methyl-3-(pyrimidin-2-yl)pyridin-2-yl)methanone

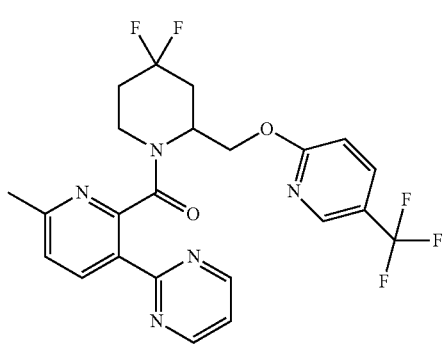 [SMILES: Cc1ccc(-c2ncccn2)c(C(=O)N2CCC(F)(F)CC2COc2ccc(C(F)(F)F)cn2)n1]

6-methyl-3-(pyrimidin-2-yl)picolinic acid (33 mg; 0.12 mmol), N-methyl morpholine (35 μl; 0.3 mmol) and 2-chloro-4,6-dimethoxy-1,3,5-triazine (27 mg; 0.15 mmol) dissolved in dry 1,4-dioxane (1 ml) were stirred at 25° C. for 0.5 hours, then intermediate 18 (30 mg; 0.1 mmol.) dissolved in 1,4-dioxane was added. After 3 hours at 80° C. solvents were evaporated and residue was dissolved in EtOAc, washed with HCl 0.1N, NaOH 1N and brine. The crude was purified by silica gel column chromatography (DCM to DCM/AcOEt=80/20) to obtain 20 mg of the title compound as light yellow solid.

MS (ESI) m/z: 494 [M+H]+.

1HNMR (CDCl3) δ ppm=8.76-8.89 (m, 2H), 8.57-8.66 (m, 1H), 8.21-8.50 (m, 1H), 7.72-7.83 (m, 1H), 7.25-7.39 (m, 2H), 6.75-6.92 (m, 1H), 4.99-5.48 (m, 1H), 4.80-4.87 (m, 1H), 4.48-4.64 (m, 1H), 3.54-4.39 (m, 1H), 3.22-3.52 (m, 1H), 2.56-2.68 (m, 4H), 1.90-2.40 (m, 3H)

Example 92

Compound 49 (±)(4,4-difluoro-2-(((5-(trifluoromethyl)pyridin-2-yl)oxy)methyl)piperidin-1-yl)(6-methyl-3-(pyrimidin-2-yl)pyridin-2-yl)methanone (Isomer A)

The enantiomeric mixture of (±)(4,4-difluoro-2-(((5-(trifluoromethyl)pyridin-2-yl)oxy)methyl)piperidin-1-yl)(6-methyl-3-(pyrimidin-2-yl)pyridin-2-yl)methanone (Compound 35, 20 mg) was separated by chiral preparative HPLC (preparative chromatographic conditions: Method G) to give the title compound (7 mg) as white solid.

HPLC retention time: 17.6 min

Example 93

Preparation of Compound 50: (RS) (4,4-difluoro-2-(((5-(trifluoromethyl)pyridin-2-yl)amino)methyl)piperidin-1-yl)(3-iodo-6-methylpyridin-2-yl)methanone

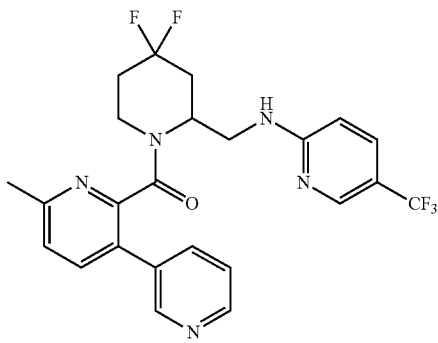 [SMILES: Cc1ccc(-c2cccnc2)c(C(=O)N2CCC(F)(F)CC2CNc2ccc(C(F)(F)F)cn2)n1]

To a suspension of intermediate 35 (25 mg, 46.3 μmol), 3-Pyridinylboronic Acid (5.7 mg, 46.3 μmol), and Pd Tetrakistriphenylphospine (5.3 mg, 4.6 μmol), in Toluene (0.5 ml) was added the K2CO3 1M aq solution (46 μl). The mixture was sonicated for 5 min and subsequently heated at 130° C. for 15 h. To promote the reaction were added further 3-Pyridinylboronic Acid (1.5 eq; 8.6 mg), Pd Tetrakistriphenylphospine (0.2 eq; 10.6 mg) and K2CO3 1M aq solution (2 eq; 92 μl).

The reaction mixture was diluted with AcOEt (5 ml) and water (5 ml). The organic layer was separated, washed with brine, dried with Na2SO4 and filtrated. Then the solvent was evaporated under reduced pressure. The crude was purified by silica gel column chromatography (DCM to Cyclohexane/AcOEt); yield 5.35 mg, white solid.

MS (ESI) m/z: 492 [M+H]+.

1HNMR (CD3COCD3) δ ppm=8.59-8.94 (m, 2H), 8.09-8.32 (m, 1H), 7.82-7.94 (m, 2H), 7.58-7.65 (m, 1H), 7.45-7.54 (m, 1H), 7.35-7.42 (m, 1H), 6.64-6.90 (m, 1H), 6.33-6.62 (m, 1H), 4.70-5.26 (m, 1H), 3.78-4.30 (m, 2H), 3.27-3.60 (m, 2H), 3.02-3.09 (m, 1H), 2.50-2.57 (m, 3H), 2.09-2.34 (m, 1H), 1.90-2.02 (m, 1H), 1.49-1.71 (m, 1H).

Example 94

Preparation of Compound 51: (RS)(4,4-difluoro-2-((5-(trifluoromethylpyridin-2-yl)amino)methyl)piperidin-1-yl)(3-phenylpyridin-2-yl)methanone

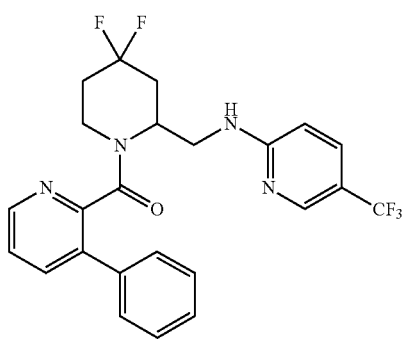 [SMILES: O=C(c1ncccc1-c1ccccc1)N1CCC(F)(F)CC1CNc1ccc(C(F)(F)F)cn1]

To a suspension of intermediate 36 (25 mg, 52.2 μmol), 3-phenylboronic acid (9.5 mg, 78.2 μmol), and Pd Tetrakistriphenylphospine (6 mg, 5.2 μmol), in Toluene (0.5 ml) was added the K2CO3 1M aq solution (52 μl). The mixture was sonicated for 5 min and subsequently subjected to microwaves: 1 cycle at 120° C. for 30 min. The reaction mixture was diluted with AcOEt (5 ml) and water (5 ml). The organic layer was separated, washed with brine, dried with Na2SO4 and filtrated. Then the solvent was evaporated under reduced pressure. The crude was purified by silica gel column chromatography (DCM to Cyclohexane/AcOEt); yield 18.4 mg, white solid.

MS (ESI) m/z: 477 [M+H]+.

1HNMR (CD3COCD3) δ ppm=8.32-8.60 (m, 1H), 8.00-8.25 (m, 1H), 7.83-7.94 (m, 1H), 7.32-7.66 (m, 7H), 6.61-6.71 (m, 1H), 6.36-6.61 (m, 1H), 4.71-5.26 (m, 1H), 4.04-4.10 (m, 1H), 3.60-3.82 (m, 1H), 3.38-3.56 (m, 1H), 3.28-3.34 (m, 1H), 2.97-3.04 (m, 1H), 1.98-2.27 (m, 1H, under the solvent peak), 1.75-1.89 (m, 1H), 1.37-1.55 (m, 1H).

Example 95

Preparation of Compound 52: (RS) (4,4-difluoro-2-(((5-(trifluoromethyl)pyridin-2-yl)amino)methyl)piperidin-1-yl)(6-methyl-[3,4'-bipyridin]-2-yl)methanone

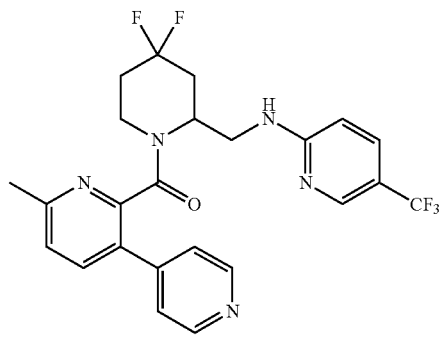 [SMILES: Cc1ccc(-c2ccncc2)c(C(=O)N2CCC(F)(F)CC2CNc2ccc(C(F)(F)F)cn2)n1]

To a suspension of intermediate 35 (25 mg, 46.3 μmol), 4-pyridinylboronic acid (9.6 mg, 69.5 μmol), and Pd Tetrakistriphenylphospine (5.3 mg, 4.6 μmol), in Toluene (0.5 ml) was added the K2CO3 1M aq solution (46 μl). The mixture was sonicated for 5 min and subsequently subjected to microwaves: 1 cycle at 120° C. for 30 min. To promote the reaction were added further 4-Pyridinylboronic Acid (1 eq; 9.6 mg), Pd Tetrakistriphenylphospine (0.1 eq; 5.3 mg) and K2CO3 1M aq solution (1 eq; 46 μl): the mixture was heated (microwave) at 120° C. (3×30 min). The reaction mixture was diluted with AcOEt (5 ml) and water (5 ml). The organic layer was separated, washed with brine, dried with Na2SO4 and filtrated. Then the solvent was evaporated under reduced pressure. The crude was purified by silica gel column chromatography (Cyclohexane/AcOEt=9/1 to 1/9); yield 4.9 mg, white solid.

MS (ESI) m/z: 492 [M+H]+.

1HNMR (CD3COCD3) δ ppm=8.57-8.75 (m, 2H), 8.08-8.33-(m, 1H), 7.76-(m, 1H), 7.76-7.89 (m, 1H), 7.58-7.67 (m, 1H), 7.52-7.53 (m, 1H), 7.36-7.48 (m, 1H), 6.42-6.91 (m, 2H), 4.71-5.27 (m, 1H), 4.22-4.35 (m, 1H), 3.94-4.00 (m, 1H), 3.80-3.89 (m, 1H), 3.51-3.57 (m, 1H), 3.28-3.24 (m, 1H), 3.05-3.12 (m, 1H), 2.51-2.57 (m, 1H), 1.87-2.34 (m, 3H, under the solvent peaks), 1.57-1.75 (m, 1H).

Example 96

Preparation of Compound 53: (RS)(4,4-difluoro-2-(((5-(trifluoromethyl)pyridin-2-yl)amino)methyl) piperidin-1-yl)(6'-methyl-[2,3'-bipyridin]-2'-yl) methanone

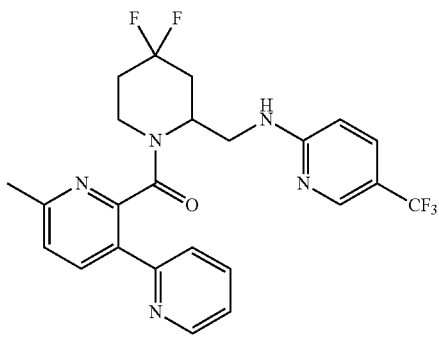 [SMILES: Cc1ccc(-c2ccccn2)c(C(=O)N2CCC(F)(F)CC2CNc2ccc(C(F)(F)F)cn2)n1]

To a suspension of intermediate 35 in dry DMF (0.5 ml) and under a N2 atmosphere, 2-(Tributylstannyl)pyridine (25.5 mg; 6.94 μm) Pd Tetrakistriphenylphospine (5.3 mg; 0.46 μm), CsF (14.1 mg; 92.6 μm), and CuI (1.8 mg; 0.92 μm), were added and the mixture was subjected to microwaves: 1 cycle at 130° C. for 10 min.

The reaction mixture was diluted with DCM (5 ml) and water (5 ml). The organic layer was separated with a Phase Separator Column, dried with Na2SO4 and filtrated. Then the solvent was evaporated under reduced pressure.

Purification onto SPE_SCX (2 g), eluting with MeOH then Ammonia (2M in MeOH), lead to the crude which was purified by C18 column chromatography (Gradient H2O to H2O/AcCN, containing 0.1% of AcOH); the fractions containing the product were collected, AcCN was evaporated off and sat NaHCO3. Subsequently the aqueous phase was extracted with AcOEt, the organic layers were dried over anhydrous Na2SO4 and concentrated; yield 6.17 mg, white solid.

MS (ESI) m/z: 492 [M+H]+.

1HNMR (CD3COCD3) δ ppm=8.59-8.63 (m, 1H), 8.25-8.35 (m, 1H), 8.09-8.11 (m, 1H), 7.86-7.97 (m, 1H), 7.74-7.81 (m, 1H), 7.61-7.68 (m, 1H), 7.33-7.45 (m, 1H), 6.63-6.66 (m, 1H), 4.88-5.25 (m, 1H), 4.48-4.51 (m, 1H), 4.01-4.06 (m, 1H), 3.52-3.73 (m, 1H), 3.36-3.42 (m, 1H), 3.51-3.57 (m, 1H), 3.07-3.14 (m, 1H), 2.53-2.63 (m, 3H), 1.91-2.51 (m, 3H), 1.90-2.04 (m, 1H).

Example 97

Preparation of Compound 54: (RS) (4,4-difluoro-2-(((5-(trifluoromethyl)pyridin-2-yl)amino)methyl) piperidin-1-yl)(3-(pyrimidin-2-yl)pyridin-2-yl) methanone

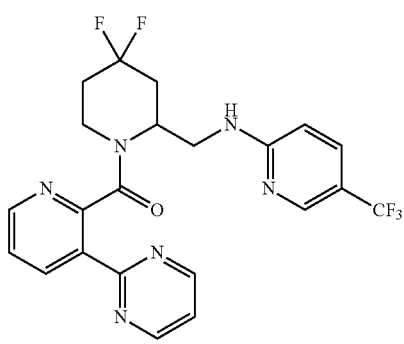 [SMILES: O=C(c1ncccc1-c1ncccn1)N1CCC(F)(F)CC1CNc1ccc(C(F)(F)F)cn1]

To a suspension of intermediate 36 in dry DMF (0.5 ml) and under a N2 atmosphere, (Tributylstannyl)pyrimidine (28.9 mg, 78.2 μm) Pd Tetrakistriphenylphospine (5.3 mg; 5.2 μm), CsF (15.9 mg; 104.4 μm) and CuI (2.0 mg; 10.4 μm) were added and the mixture was subjected to microwaves: 6 cycle at 130° C. for 10 min; to promote the reaction 1 more equivalent of (Tributylstannyl)pyrimidine (28.9 mg, 78.2 μm) was added and the mixture heated at 120° C. for 2 hours.

The reaction mixture was diluted with DCM (5 ml) and water (5 ml). The organic layer was separated with a Phase Separator Column, dried with Na2SO4 and filtrated. Then the solvent was evaporated under reduced pressure.

Purification onto SPE_SCX (2 g), eluting with MeOH then Ammonia (2M in MeOH), lead to the crude which was purified by C18 column chromatography (Gradient H2O to H2O/AcCN, containing 0.1% of AcOH); the fractions containing the product were collected; AcCN was evaporated off and sat. NaHCO3 was added. Subsequently the aqueous phase was extracted with AcOEt, the organic layers were dried over anhydrous Na2SO4 and concentrated; yield 4.16 mg, white solid.

MS (ESI) m/z: 479 [M+H]+.

1HNMR (CD3COCD3) δ ppm=8.60-8.95 (m, 3H), 8.18-8.36 (m, 1H), 7.46-7.67 (m, 3H), 6.53-7.19 (m, 2H), 4.75-5.31 (m, 1H), 4.46-4.48 (m, 1H), 3.98-4.08 (m, 1H), 3.45-366 (m, 2H), 3.04-322 (m, 1H), 2.09-2.62 (m, 4H).

Biological Section:

In a typical experiment, the antagonistic activity against human OX1 and OX2 receptors is determined by using CHO e HEK-293 cells transfected with human recombinant OX1 and OX2 receptors respectively, seeded at density of 2 and $3 \times 10^4$ cells/well respectively in a 96 fluorimetry well plate. Thus the plate was loaded with the calcium dye (Fluo-4NW/ probenecid in HBSS, Hepes 20 mM, pH 7.4; Invitrogen) at 37° C. for 60 min. Afterward the temperature was equilibrated at 22° C. for 15 min and the [Ca2+]i measured directly on the plate by using a fluorescent plate reader (CeliLux Perkin Elmer).

Invention compounds were dissolved in DMSO, diluted in HBSS (DMSO, 0.3% final) and added to the wells. After 5 min CHO cells were activated with orexin-A, 3 nM while HEK-293 cells were activated with orexin-B, 10 nM. The compounds, dissolved in DMSO and diluted in the medium (DMSO, 0.3% final), have been analysed in the 1 nM-1 μM concentration range (every concentration in duplicate). The antagonistic activity has been expressed as pKb (co-logarithm of the apparent dissociation constant calculated by using the modified Cheng Prusoff equation). The results are expressed as percent of control specific antagonist response ((measured specific response/control specific agonist response)×100) obtained in the presence of the test compounds.

The $IC_{50}$ values (concentration causing a half-maximal inhibition of the control specific agonist response) were determinated by non-linear regression analysis of the concentration curves generated with mean replicate values using hill equation curve fitting. The $IC_{50}$ values are obtained by the arithmetical mean of at least two experiments. Compounds of the following example tested according to this example gave pKbs as follows

| Compound | PKb OX1 | PKb OX2 |
| --- | --- | --- |
| 1 | 8.0 | 4.0 |
| 2 | 8.7 | 4.0 |

-continued

| Compound | PKb OX1 | PKb OX2 |
|---|---|---|
| 3 | 9.3 | 4.0 |
| 4 | 8.6 | 6.7 |
| 5 | 8.3 | 4.0 |
| 6 | 8.3 | 4.0 |
| 7 | 8.6 | 4.0 |
| 8 | 8.8 | 4.0 |
| 9 | 7.8 | 4.0 |
| 10 | 8.1 | 4.0 |
| 11 | 8.1 | 5.0 |
| 12 | 8.7 | 4.0 |
| 13 | 7.0 | 4.0 |
| 14 | 8.6 | 4.0 |
| 15 | 6.9 | 4.0 |
| 16 | 9.2 | 5.0 |
| 17 | 7.0 | 4.0 |
| 18 | 7.5 | 6.0 |
| 19 | 8.3 | 4.0 |
| 20 | 9.1 | 6.5 |
| 21 | 8.3 | 4.0 |
| 22 | 9.2 | 4.0 |
| 23 | 7.1 | 4.0 |
| 24 | 9.0 | 5.0 |
| 25 | 9.1 | 5.0 |
| 26 | 8.8 | 5.0 |
| 27 | 8.8 | 5.0 |
| 28 | 7.8 | 4.0 |
| 29 | 7.8 | 4.0 |
| 30 | 7.6 | 4.0 |
| 31 | 8.4 | 5.0 |
| 32 | 8.6 | 5.0 |
| 33 | 8.7 | 4.0 |
| 34 | 8.6 | 4.0 |
| 35 | 7.5 | 4.0 |
| 36 | 8.5 | 5.0 |
| 37 | 6.7 | 4.0 |
| 38 | 8.5 | 6.9 |
| 39 | 7.5 | 5.0 |
| 40 | 7.2 | 4.0 |
| 41 | 8.8 | 5.0 |
| 42 | 8.2 | 4.0 |
| 43 | 8.5 | 5.0 |
| 44 | 8.4 | 6.7 |
| 45 | 8.4 | 5.0 |
| 46 | 7.8 | 5.0 |
| 47 | 7.9 | 5.0 |
| 48 | 8.1 | 4.0 |
| 49 | 8.3 | 4.0 |
| 50 | 8.3 | 4.0 |
| 51 | 8.2 | 5.0 |
| 52 | 7.4 | 4.0 |
| 53 | 7.8 | 5.0 |
| 54 | 8.5 | 4.0 |

What is claimed is:

1. A compound of formula (I)

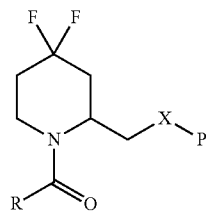

(I)

or a pharmaceutically acceptable salt thereof, wherein R is
a 6-membered aromatic ring,
a 5- or 6-membered heteroaromatic ring comprising 1 to 3 heteroatoms selected from S, O and N, or
a 6-membered benzocondensed heteroaromatic ring containing N as a heteroatom,
optionally each said ring of R being substituted with one of
a) one or two substituents selected from the group consisting of: $(C_1-C_3)$alkyl, $(C_3-C_5)$cycloalkyloxy, $(C_1-C_3)$alkylcarbonyl, cyano, trifluoromethyl, dimethylamino, and a phenyl optionally substituted with one or more halogen atoms, or
b) a 5- or 6-membered heterocycle containing from one to three nitrogen atoms;
X is O or N; and
P is pyridyl, pyrimidyl, pyrazyl, or pyridazyl, wherein P is optionally substituted with one or more substituents selected from the group consisting of $(C_1-C_3)$alkyl, halogen, trifluoromethyl, and cyano.

2. The compound of formula (I) according to claim 1 wherein R is selected from the group consisting of phenyl, 1,3 thiazole, pyrimidine, pyridine, isoquinoline and quinoline, wherein each ring is optionally substituted with one of
a) one or two substituents selected from the group consisting of $(C_1-C_3)$alkyl, $(C_3-C_5)$cycloalkyloxy, $(C_1-C_3)$ alkylcarbonyl, cyano, trifluoromethyl, dimethylamino, and a phenyl optionally substituted with one or more halogen atoms, or
b) a 5- or 6-membered heterocycle containing from one to three nitrogen atoms.

3. The compound of formula (I) according to claim 1 wherein the 6-membered aromatic ring or the 5- or 6-membered heteroaromatic ring comprising 1 to 3 heteroatoms selected from S, O and N are substituted with one of
a) one or two substituents selected from the group consisting of $(C_1-C_3)$alkyl, $(C_3-C_5)$cycloalkyloxy, $(C_1-C_3)$ alkylcarbonyl, cyano, trifluoromethyl, dimethylamino, and a phenyl optionally substituted with one or more halogen atoms, or
b) a 5- or 6-membered heterocycle containing from one to three nitrogen atoms.

4. The compound of formula (I) according to claim 1 wherein P is pyridyl, pyrimidyl, pyrazyl, or pyridazyl, wherein each ring of P is optionally substituted with one or more substituents selected from the group consisting of $(C_1-C_3)$alkyl, halogen, trifluoromethyl, and cyano.

5. The compound according to claim 1 wherein X is N and is of formula (Ia)

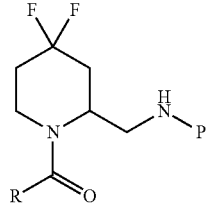

Ia wherein R is i) a 6-membered aromatic ring, or ii) a 5- or 6-membered heteroaromatic ring comprising 1 to 3 heteroatoms selected from S, O and N, or iii) a 6-membered benzocondensed heteroaromatic ring containing N as heteroatom, wherein each of said rings i), ii) and iii) is optionally substituted with one of
a) one or two substituents selected from the group consisting of $(C_1-C_3)$alkyl, $(C_3-C_5)$cycloalkyloxy, (C1-C3)alkylcarbonyl, cyano, trifluoromethyl, dimetylamino, and phenyl optionally substituted with one or more halogen atoms, or
   b) a 5- or 6-membered heterocycle comprising from one to three nitrogen atoms; and
P is pyridyl, pyrimidyl, pyrazyl, or pyridazyl, wherein each ring of P is optionally substituted with one or more substituents selected from the group consisting of ($C_1$-$C_3$)alkyl, halogen, trifluoromethyl, and cyano.

6. The compound according to claim 5 wherein R is phenyl optionally substituted with a substituent selected from the group consisting of cyclopropyl($C_1$-$C_3$)alkyloxy, triazolyl, pyrimidyl, and phenyl.

7. The compound according to claim 6 wherein the phenyl is substituted in position 2.

8. The compound according to claim 5 wherein R is a 5-membered heteroaromatic ring, containing 1 to 3 heteroatoms selected from S and/or N substituted with either
   a) one or two substituents selected from the group consisting of ($C_1$-$C_3$)alkyl, ($C_3$-$C_5$)cycloalkyloxy, ($C_1$-$C_3$) alkylcarbonyl, cyano, trifluoromethyl, dimetylamino, and phenyl optionally substituted with one or more halogen atoms, or
   b) a 5- or 6-membered heterocycle comprising from one to three nitrogen atoms.

9. The compound according to claim 8 wherein the 5-membered heteroaromatic ring is thiazole substituted with at least one substituent selected from the group consisting of methyl, phenyl, and phenyl substituted with one or more halogen atoms.

10. The compound according to claim 5 wherein R is a 6-membered heteroaromatic ring containing N as heteroatom optionally substituted with one of
   a) one or two substituents selected from the group consisting of (C1-C3)alkyl, (C3-C5)cycloalkyloxy, (C1-C3)alkylcarbonyl, cyano, trifluoromethyl, dimetylamino, and phenyl optionally substituted with one or more halogen atoms, or
   b) a 5- or 6-membered heterocycle comprising from one to three nitrogen atoms.

11. The compound according to claim 10 wherein the 6-membered heteroaromatic ring containing N as heteroatom is pyridyl or pyrimidyl optionally substituted with a group selected from the group consisting of ($C_1$-$C_3$)alkyloxy, trifluoromethyl, halogen, triazolyl, pyrimidyl, and phenyl.

12. The compound according to claim 1 wherein P is a pyridyl ring optionally substituted.

13. The compound according to claim 12 wherein the pyridyl ring is substituted with one or more substituents selected from the group consisting of trifluoromethyl, methyl and halogen.

14. The compound according to claim 5 selected from the group consisting of:
   (RS)(2-(((5-chloropyridin-2-yl)amino)methyl)-4,4-difluoropiperidin-1-yl)(2-methyl-5-phenylthiazol-4-yl)methanone,
   (2-(((5-chloropyridin-2-yl)amino)methyl)-4,4-difluoropiperidin-1-yl)(2-methyl-5-phenylthiazol-4-yl)methanone (enantiomer A),
   (2-(((5-chloropyridin-2-yl)amino)methyl)-4,4-difluoropiperidin-1-yl)(5-methyl-2-(2H-1,2,3-triazol-2-yl)phenyl)methanone (enantiomer A),
   (2-(((4,6-dimethylpyrimidin-2-yl)amino)methyl)-4,4-difluoropiperidin-1-yl)(5-methyl-2-(2H-1,2,3-triazol-2-yl)phenyl)methanone (enantiomer A),
   (RS)(4,4-difluoro-2-(((5-(trifluoromethyl)pyridin-2-yl)amino)methyl)piperidin-1-yl)(5-methyl-2-(2H-1,2,3-triazol-2-yl)phenyl)methanone,
   (RS)(2-(((5-chloropyridin-2-yl)amino)methyl)-4,4-difluoropiperidin-1-yl)(5-methyl-2-(pyrimidin-2-yl)phenyl)methanone,
   (2-(((5-chloropyridin-2-yl)amino)methyl)-4,4-difluoropiperidin-1-yl)(5-methyl-2-(pyrimidin-2-yl)phenyl) methanone (enantiomer A),
   (2-(((5-chloropyridin-2-yl)amino)methyl)-4,4-difluoropiperidin-1-yl)(6-methyl-3-(2H-1,2,3-triazol-2-yl)pyridin-2-yl)methanone (enantiomer A),
   (2-(((5-chloropyridin-2-yl)amino)methyl)-4,4-difluoropiperidin-1-yl)(6-methyl-3-(2H-1,2,3-triazol-2-yl)pyridin-2-yl)methanone (enantiomer B),
   (RS)(2-(((5-chloropyridin-2-yl)amino)methyl)-4,4-difluoropiperidin-1-yl)(2-ethoxyphenyl)methanone,
   (RS)(2-(((5-chloropyridin-2-yl)amino)methyl)-4,4-difluoropiperidin-1-yl)(2,5-dimethoxyphenyl)methanone,
   (RS)(2-(((5-chloropyridin-2-yl)amino)methyl)-4,4-difluoropiperidin-1-yl)(2-(cyclopropylmethoxy)phenyl)methanone,
   (RS)(2-(((5-chloropyridin-2-yl)amino)methyl)-4,4-difluoropiperidin-1-yl)(2-(cyclopentyloxy)phenyl)methanone,
   (RS)(2-(((5-chloropyridin-2-yl)amino)methyl)-4,4-difluoropiperidin-1-yl)(6-methyl-3-(pyrimidin-2-yl)pyridin-2-yl)methanone,
   (RS)(2-(((5-chloropyridin-2-yl)amino)methyl)-4,4-difluoropiperidin-1-yl)(5-methyl-2-(pyrimidin-2-yl)pyridin-3-yl)methanone,
   (2-(((5-chloropyridin-2-yl)amino)methyl)-4,4-difluoropiperidin-1-yl)(6-methyl-3-(pyrimidin-2-yl)pyridin-2-yl) methanone (enantiomer A),
   (2-(((5-chloropyridin-2-yl)amino)methyl)-4,4-difluoropiperidin-1-yl)(6-methyl-3-(pyrimidin-2-yl)pyridin-2-yl)methanone (enantiomer B),
   (RS)(2-(((5-chloropyridin-2-yl)amino)methyl)-4,4-difluoropiperidin-1-yl)(4-(dimethylamino)-[1,1'-biphenyl]-2-yl)methanone,
   (RS)(5-chloro-2-(pyrimidin-2-yl)phenyl)(2-(((5-chloropyridin-2-yl)amino)methyl)-4,4-difluoropiperidin-1-yl)methanone,
   (4,4-difluoro-2-(((5-(trifluoromethyl)pyridin-2-yl)amino)methyl)piperidin-1-yl)(6-methyl-3-(pyrimidin-2-yl)pyridin-2-yl)methanone (enantiomer A),
   (RS)(2-(benzyloxy)phenyl)(2-(((5-chloropyridin-2-yl)amino)methyl)-4,4-difluoropiperidin-1-yl)methanone,
   (RS)(2-(((5-chloropyridin-2-yl)amino)methyl)-4,4-difluoropiperidin-1-yl)(isoquinolin-1-yl)methanone,
   (2-(((5-chloropyridin-2-yl)amino)methyl)-4,4-difluoropiperidin-1-yl)(isoquinolin-1-yl)methanone (enantiomer A),
   (2-(((5-chloropyridin-2-yl)amino)methyl)-4,4-difluoropiperidin-1-yl)(isoquinolin-1-yl)methanone (enantiomer B),
   (RS)(2-(((5-chloropyridin-2-yl)amino)methyl)-4,4-difluoropiperidin-1-yl)(quinolin-8-yl)methanone,
   (2-(((5-chloropyridin-2-yl)amino)methyl)-4,4-difluoropiperidin-1-yl)(quinolin-8-yl)methanone (enantiomer A),
   (RS)3-(2-(((5-chloropyridin-2-yl)amino)methyl)-4,4-difluoropiperidine-1-carbonyl)-4-(pyrimidin-2-yl)benzonitrile,
   (RS)(2-(((5-chloropyridin-2-yl)amino)methyl)-4,4-difluoropiperidin-1-yl)(3-(pyrimidin-2-yl)pyridin-4-yl)methanone, (RS)6-(((4,4-difluoro-1-(6-methyl-3-(pyrimidin-2-yl)picolinoyl)piperidin-2-yl)methyl)amino)nicotinonitrile,
(RS)(4,4-difluoro-2-(((5-(trifluoromethyl)pyridin-2-yl)amino)methyl)piperidin-1-yl)(5-fluoro-2-(2-methylpyrimidin-5-yl)phenyl)methanone,
(RS)(4,4-difluoro-2-(((3-fluoro-5-(trifluoromethyl)pyridin-2-yl)amino)methyl)piperidin-1-yl)(6-methyl-3-(pyrimidin-2-yl)pyridin-2-yl)methanone,
(RS)(4,4-difluoro-2-(((3-fluoro-5-(trifluoromethyl)pyridin-2-yl)amino)methyl)piperidin-1-yl)(isoquinolin-1-yl)methanone,
(RS)(4,4-difluoro-2-(((5-(trifluoromethyl)pyridin-2-yl)amino)methyl)piperidin-1-yl)(isoquinolin-1-yl)methanone,
(RS)(4,4-difluoro-2-(((5-(trifluoromethyl)pyridin-2-yl)amino)methyl)piperidin-1-yl)(quinolin-4-yl)methanone,
(RS)(4,4-difluoro-2-(((5-(trifluoromethyl)pyridin-2-yl)amino)methyl)piperidin-1-yl)(6-methyl-3-phenylpyridin-2-yl)methanone,
(RS)(4,4-difluoro-2-(((5-(trifluoromethyl)pyridin-2-yl)amino)methyl)piperidin-1-yl)(3-(pyrimidin-2-yl)-6-(trifluoromethyl)pyridin-2-yl)methanone,
(4,4-difluoro-2-(((5-(trifluoromethyl)pyridin-2-yl)amino)methyl)piperidin-1-yl)(isoquinolin-1-yl)methanone (enantiomer A),
(RS)(4,4-difluoro-2-(((5-(trifluoromethyl)pyrazin-2-yl)amino)methyl)piperidin-1-yl)(6-methyl-3-(pyrimidin-2-yl)pyridin-2-yl)methanone,
(RS)(4,4-difluoro-2-(((5-(trifluoromethyl)pyrazin-2-yl)amino)methyl)piperidin-1-yl)(6-methyl-3-phenylpyridin-2-yl)methanone,
(RS)(4,4-difluoro-2-(((3-fluoro-5-(trifluoromethyl)pyridin-2-yl)amino)methyl)piperidin-1-yl)(6-methyl-3-phenylpyridin-2-yl)methanone, and
(RS)(4,4-difluoro-2-(((5-(trifluoromethyl)pyridin-2-yl)amino)methyl)piperidin-1-yl)(3-phenylpyridin-2-yl)methanone.

15. The compound according to claim 1 wherein X is O having the formula (Ib)

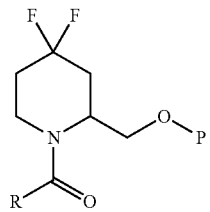

wherein R is i) a 6-membered aromatic ring, or ii) a 5- or 6-membered heteroaromatic ring comprising 1 to 3 heteroatoms selected from S, O and N, or iii) a 6-membered benzocondensed heteroaromatic ring containing N as heteroatom, wherein each of said rings i), ii) and iii) is optionally substituted with one of
a) one or two substituents selected from the group consisting of (C1-C3)alkyl, (C3-C5)cycloalkyloxy, (C1-C3)alkylcarbonyl, cyano, trifluoromethyl, dimetylamino, and phenyl optionally substituted with one or more halogen atoms, or
b) a 5- or 6-membered heterocycle comprising from one to three nitrogen atoms; and
P is pyridyl, pyrimidyl, pyrazyl, or pyridazyl, wherein each ring of P is optionally substituted with one or more substituents selected from the group consisting of (C1-C3)alkyl, halogen, trifluoromethyl, and cyano.

16. The compound according to claim 15 wherein R is a phenyl optionally substituted with a substituent selected from the group consisting of cyclopropyl, $(C_1-C_3)$alkyloxy, triazolyl, pyrimidyl, and phenyl.

17. The compound according to claim 15 wherein R is a 5-membered heteroaromatic ring containing S and/or N as heteroatoms, substituted with one of
a) one or two substituents selected from the group consisting of (C1-C3)alkyl, (C3-C5)cycloalkyloxy, (C1-C3)alkylcarbonyl, cyano, trifluoromethyl, dimetylamino, and phenyl optionally substituted with one or more halogen atoms, or
b) a 5- or 6-membered heterocycle comprising from one to three nitrogen atoms.

18. The compound according to claim 15 wherein R is a thiazole ring optionally substituted with at least one substituent selected from the group consisting of methyl, phenyl, and phenyl substituted with one or more halogen atoms.

19. The compound according to claim 15 wherein R is 6-membered heteroaromatic ring containing N as a heteroatom substituted with one of
a) one or two substituents selected from the group consisting of (C1-C3)alkyl, (C3-C5)cycloalkyloxy, (C1-C3)alkylcarbonyl, cyano, trifluoromethyl, dimetylamino, and phenyl optionally substituted with one or more halogen atoms, or
b) a 5- or 6-membered heterocycle comprising from one to three nitrogen atoms.

20. The compound according to claim 19 wherein R is pyrimidine or pyridyl, each being optionally substituted with at least one substituent selected from the group consisting of $(C_1-C_3)$alkyloxy, trifluoromethyl, halogen, triazolyl, pyrimidyl, and phenyl.

21. The compound according to claim 15 wherein P is a pyridyl ring, optionally substituted with one or more substituents selected from the group consisting of trifluoromethyl, methyl, and halogen.

22. The compound according to claim 15, wherein said formula (Ib) is selected from the group consisting of:
(RS)(4,4-difluoro-2-(((5-(trifluoromethyl)pyridin-2-yl)oxy)methyl)piperidin-1-yl)(6-methyl-3-(pyrimidin-2-yl)pyridin-2-yl)methanone, and
(4,4-difluoro-2-(((5-(trifluoromethyl)pyridin-2-yl)oxy)methyl)piperidin-1-yl)(6-methyl-3-(pyrimidin-2-yl)pyridin-2-yl)methanone (enantiomer A).

23. A pharmaceutical composition comprising a compound of formula (I) according to claim 1 or a pharmaceutically acceptable salt thereof and a pharmaceutically acceptable carrier and/or excipient.

24. A method of treatment of a disease selected from the group consisting of: sleep disorders, anxiety, compulsive disorders, and drugs and alcohol dependencies, said method comprising administering an effective amount of the compound of formula (I) according to claim 1 to a subject in need of said treatment.

* * * * *